US011527311B2

(12) United States Patent
Ansari et al.

(10) Patent No.: US 11,527,311 B2
(45) Date of Patent: *Dec. 13, 2022

(54) MULTI-SERVICES APPLICATION GATEWAY AND SYSTEM EMPLOYING THE SAME

(71) Applicant: KIP PROD P1 LP, New York, NY (US)

(72) Inventors: Amir Ansari, Plano, TX (US); George A. Cowgill, Farmersville, TX (US); Ramprakash Masina, Plano, TX (US); Jude P. Ramayya, Richardson, TX (US); Alvin R. McQuarters, Euless, TX (US); Atousa Raissyan, Potomac, MD (US); Leon E. Nicholls, Santa Clara, CA (US)

(73) Assignee: KIP PROD P1 LP, New York, NY (US)

( * ) Notice: Subject to any disclaimer, the term of this patent is extended or adjusted under 35 U.S.C. 154(b) by 171 days.

This patent is subject to a terminal disclaimer.

(21) Appl. No.: 16/876,946

(22) Filed: May 18, 2020

(65) Prior Publication Data

US 2020/0279626 A1    Sep. 3, 2020

Related U.S. Application Data

(63) Continuation of application No. 16/514,803, filed on Jul. 17, 2019, now Pat. No. 10,672,508, which is a
(Continued)

(51) Int. Cl.
*H04L 9/40* (2022.01)
*G16H 10/60* (2018.01)
(Continued)

(52) U.S. Cl.
CPC ............ *G16H 10/60* (2018.01); *G16Z 99/00* (2019.02); *H04L 9/30* (2013.01); *H04L 63/08* (2013.01);
(Continued)

(58) Field of Classification Search
CPC ..... H04L 63/08; H04L 63/0861; H04L 63/10; H04L 63/101; H04L 63/102; H04L 9/30;
(Continued)

(56) References Cited

U.S. PATENT DOCUMENTS 2,273,733 A    2/1942 Paddock
2,316,993 A    4/1943 Sherwood
(Continued)

FOREIGN PATENT DOCUMENTS

CN    102500747 A    11/2011
DE      3002904 A1    8/1980
(Continued)

OTHER PUBLICATIONS

"Apple moves to link TV to the computer," TVTechnology, Sep. 18, 2006, 2 pages.
(Continued)

*Primary Examiner* — Hosuk Song
(74) *Attorney, Agent, or Firm* — Perkins Coie LLP

(57) ABSTRACT

An intelligent gateway device provided at a premise (home or business) for providing and managing application services associated with use and support of a plurality of digital endpoint devices associated with the premises. The device includes a communications and processing infrastructure integrated with a peer and presence messaging based communications protocol for enabling communications between the device and an external support network and between the device and connected digital endpoint devices. A services framework at the gateway device implements the communications and processing infrastructure for enabling service management, service configuration, and authentication of user of services at the intelligent gateway. The framework provides a storage and execution environment for supporting and executing received service logic modules relating to use,
(Continued)

management, and support of the digital endpoint devices. Thus, the gateway device provides a network-based services point of presence for a plurality of digital endpoint devices at the premises.

33 Claims, 25 Drawing Sheets

Related U.S. Application Data continuation of application No. 15/214,416, filed on Jul. 19, 2016, now Pat. No. 10,403,394, which is a continuation of application No. 14/294,957, filed on Jun. 3, 2014, now Pat. No. 9,569,587, which is a continuation of application No. 14/024,362, filed on Sep. 11, 2013, now abandoned, which is a continuation-in-part of application No. 12/521,757, filed as application No. PCT/US2007/089237 on Dec. 31, 2007, now Pat. No. 8,543,665.

(60) Provisional application No. 60/882,865, filed on Dec. 29, 2006, provisional application No. 60/882,862, filed on Dec. 29, 2006.

(51) Int. Cl.
  *G16Z 99/00* (2019.01)
  *H04L 9/30* (2006.01)

(52) U.S. Cl.
  CPC ........ *H04L 63/083* (2013.01); *H04L 63/0876* (2013.01)

(58) Field of Classification Search
  CPC ... H04L 63/083; H04L 63/0876; G06F 21/31; G06F 21/32; G16H 10/60; G16Z 99/00
  See application file for complete search history.

(56) References Cited

U.S. PATENT DOCUMENTS

| | | | |
|---|---|---|---|
| 4,297,607 A | 10/1981 | Lynnworth et al. |
| 4,467,586 A | 8/1984 | Long |
| 4,814,552 A | 3/1989 | Stefik et al. |
| 4,991,148 A | 2/1991 | Gilchrist |
| 5,339,259 A | 8/1994 | Puma |
| 5,372,138 A | 12/1994 | Crowley et al. |
| 5,421,338 A | 6/1995 | Crowley et al. |
| 5,515,853 A | 5/1996 | Smith et al. |
| 5,517,579 A | 5/1996 | Baron et al. |
| 5,524,630 A | 6/1996 | Crowley et al. |
| 5,588,432 A | 12/1996 | Crowley et al. |
| 5,673,252 A | 9/1997 | Johnson et al. |
| 5,715,825 A | 2/1998 | Crowley et al. |
| 5,750,941 A | 5/1998 | Ishikawa et al. |
| 5,840,031 A | 11/1998 | Crowley et al. |
| 5,862,299 A | 1/1999 | Lee |
| 5,867,146 A | 2/1999 | Kim et al. |
| 5,867,666 A | 2/1999 | Harvey |
| 5,878,223 A | 3/1999 | Becker et al. |
| 5,943,478 A | 8/1999 | Aggarwal et al. |
| 5,977,958 A | 11/1999 | Baron et al. |
| 5,991,739 A | 11/1999 | Cupps et al. |
| 5,995,272 A | 11/1999 | Werner |
| 6,004,269 A | 12/1999 | Crowley et al. |
| 6,016,520 A | 1/2000 | Facq et al. |
| 6,029,045 A | 2/2000 | Picco |
| 6,033,150 A | 3/2000 | Culen |
| 6,039,251 A | 3/2000 | Holowko |
| 6,055,569 A | 4/2000 | O'Brien et al. |
| 6,092,114 A | 7/2000 | Shaffer et al. |
| 6,118,205 A | 9/2000 | Wood et al. |
| 6,158,483 A | 12/2000 | Trpkovski |
| 6,228,290 B1 | 5/2001 | Reames et al. |
| 6,301,609 B1 | 10/2001 | Aravamudan et al. |
| 6,330,599 B1 | 12/2001 | Harvey |
| 6,377,571 B1 | 4/2002 | Tai |
| 6,426,955 B1 | 7/2002 | Dalton |
| 6,434,158 B1 | 8/2002 | Harris |
| 6,434,618 B1 | 8/2002 | Cohen |
| 6,449,344 B1 | 9/2002 | Goldfinger et al. |
| 6,456,597 B1 | 9/2002 | Bare |
| 6,457,294 B1 | 10/2002 | Virnelson et al. |
| 6,487,646 B1 | 11/2002 | Adams et al. |
| 6,493,128 B1 | 12/2002 | Agrawal et al. |
| 6,496,575 B1 | 12/2002 | Vasell |
| 6,526,581 B1 | 2/2003 | Edson |
| 6,542,506 B1 | 4/2003 | Lee |
| 6,549,937 B1 | 4/2003 | Auerbach et al. |
| 6,553,345 B1 | 4/2003 | Kuhn |
| 6,622,168 B1 | 9/2003 | Datta |
| 6,631,412 B1 | 10/2003 | Glasser et al. |
| 6,658,091 B1 | 12/2003 | Naidoo |
| 6,671,730 B1 | 12/2003 | Akatsu |
| 6,677,976 B2 | 1/2004 | Parker et al. |
| 6,681,232 B1 | 1/2004 | Sistanizadeh et al. |
| 6,694,007 B2 | 2/2004 | Lang et al. |
| 6,697,474 B1 | 2/2004 | Hanson et al. |
| 6,731,992 B1 | 5/2004 | Ziegler |
| 6,735,619 B1 | 5/2004 | Sawada |
| 6,745,632 B1 | 6/2004 | Dryer et al. |
| 6,771,006 B2 | 8/2004 | Zioter et al. |
| 6,798,403 B2 | 9/2004 | Kitada et al. |
| 6,820,204 B1 * | 11/2004 | Desai ............... G06F 16/256 726/6 |
| 6,850,252 B1 | 2/2005 | Hoffberg |
| 6,850,901 B1 | 2/2005 | Hunter et al. |
| 6,850,979 B1 | 2/2005 | Saulpaugh et al. |
| 6,851,054 B2 | 2/2005 | Wheeler |
| 6,865,150 B1 | 3/2005 | Perkins |
| 6,868,292 B2 | 3/2005 | Ficco |
| 6,871,193 B1 | 3/2005 | Campbell et al. |
| 6,889,321 B1 | 5/2005 | Kung |
| 6,891,838 B1 | 5/2005 | Petite et al. |
| 6,898,276 B1 | 5/2005 | Millet et al. |
| 6,910,074 B1 | 6/2005 | Amin |
| 6,928,576 B2 | 8/2005 | Sekiguchi |
| 6,930,598 B2 | 8/2005 | Weiss |
| 6,931,445 B2 | 8/2005 | Davis |
| 6,952,773 B2 | 10/2005 | Wheeler |
| 6,957,275 B1 | 10/2005 | Sekiguchi |
| 6,961,335 B1 | 11/2005 | Millet et al. |
| 6,961,857 B1 | 11/2005 | Floryanzia |
| 6,965,614 B1 | 11/2005 | Osterhout et al. |
| 6,981,025 B1 | 12/2005 | Frazier |
| 6,988,070 B2 | 1/2006 | Kawasaki |
| 6,988,075 B1 | 1/2006 | Hacker |
| 7,007,070 B1 | 2/2006 | Hickman |
| 7,035,270 B2 | 4/2006 | Moore, Jr. et al. |
| 7,054,376 B1 | 5/2006 | Rubinstain et al. |
| 7,058,036 B1 | 6/2006 | Yu et al. |
| 7,075,919 B1 | 7/2006 | Wendt et al. |
| 7,123,700 B1 | 10/2006 | Weaver, III et al. |
| 7,130,719 B2 | 10/2006 | Ehlers et al. |
| 7,139,811 B2 | 11/2006 | Lev Ran et al. |
| 7,167,920 B2 | 1/2007 | Traversal et al. |
| 7,174,512 B2 | 2/2007 | Martin |
| 7,203,477 B2 | 4/2007 | Coppinger et al. |
| 7,207,048 B2 | 4/2007 | McQuillan et al. |
| 7,222,087 B1 | 5/2007 | Bezos et al. |
| 7,235,710 B2 | 6/2007 | Hatzfeld et al. |
| 7,266,589 B2 | 9/2007 | Brownhill |
| 7,269,162 B1 | 9/2007 | Turner |
| 7,277,384 B1 | 10/2007 | Chan |
| 7,305,550 B2 | 12/2007 | Oliver |
| 7,313,120 B2 | 12/2007 | Ekberg et al. |
| 7,313,251 B2 * | 12/2007 | Rhoads ............ G06K 19/06037 382/100 |
| 7,336,262 B2 | 2/2008 | Tsuji |
| 7,349,993 B2 | 3/2008 | Kawamoto et al. |
| 7,397,807 B2 | 7/2008 | Chen et al. |
| 7,403,838 B2 | 7/2008 | Deen et al. |

(56) References Cited

U.S. PATENT DOCUMENTS

| | | |
|---|---|---|
| 7,421,483 B1 | 9/2008 | Kalra |
| 7,433,836 B1 | 10/2008 | August |
| 7,444,401 B1 | 10/2008 | Keyghobad |
| 7,454,462 B2 * | 11/2008 | Belfiore .................. G06F 9/54 709/203 |
| 7,461,122 B2 | 12/2008 | Kawana |
| 7,480,724 B2 | 1/2009 | Zimler et al. |
| 7,526,539 B1 | 4/2009 | Hsu |
| 7,551,071 B2 | 6/2009 | Bennett et al. |
| 7,574,660 B2 | 8/2009 | Campbell et al. |
| 7,584,263 B1 | 9/2009 | Hicks |
| 7,596,692 B2 | 9/2009 | Fox et al. |
| 7,627,679 B1 | 12/2009 | Bowen et al. |
| 7,650,361 B1 | 1/2010 | Wong |
| 7,673,001 B1 | 3/2010 | Battle et al. |
| 7,685,629 B1 | 3/2010 | White |
| 7,706,928 B1 | 4/2010 | Howell |
| 7,707,606 B2 | 4/2010 | Hofrichter et al. |
| 7,761,527 B2 | 7/2010 | Ferreira et al. |
| 7,765,294 B2 | 7/2010 | Edwards et al. |
| 7,780,080 B2 * | 8/2010 | Owen ................ G06Q 20/4014 235/382 |
| 7,809,605 B2 | 10/2010 | Tonse et al. |
| 7,818,444 B2 | 10/2010 | Brueck |
| 7,831,748 B2 | 11/2010 | Dernis et al. |
| 7,836,044 B2 | 11/2010 | Kamvar et al. |
| 7,865,735 B2 | 1/2011 | Yiachos |
| 7,895,633 B2 | 2/2011 | Van Hoff et al. |
| 7,913,278 B2 | 3/2011 | Ellis et al. |
| 7,933,970 B2 | 4/2011 | Zimler et al. |
| 7,948,992 B1 | 5/2011 | Holmgren et al. |
| 7,961,712 B2 | 6/2011 | Rabenko et al. |
| 7,970,863 B1 | 6/2011 | Fontaine |
| 7,970,914 B2 | 6/2011 | Bowen et al. |
| 7,987,490 B2 | 7/2011 | Ansari et al. |
| 8,005,915 B2 | 8/2011 | Jeon |
| 8,020,174 B2 | 9/2011 | Sedogbo |
| 8,027,335 B2 | 9/2011 | Ansari et al. |
| 8,031,726 B2 | 10/2011 | Ansari et al. |
| 8,032,409 B1 | 10/2011 | Mikurak |
| 8,060,589 B1 | 11/2011 | Kao |
| 8,078,688 B2 | 12/2011 | Ansari et al. |
| 8,086,495 B2 | 12/2011 | Ansari et al. |
| 8,090,856 B1 | 1/2012 | Bonefas |
| 8,107,217 B2 | 1/2012 | Watanabe |
| 8,189,608 B2 | 5/2012 | Duo et al. |
| 8,205,240 B2 | 6/2012 | Ansari et al. |
| 8,280,978 B2 | 10/2012 | Ansari et al. |
| 8,281,010 B2 | 10/2012 | Ansari et al. |
| 8,315,266 B1 | 11/2012 | Lam et al. |
| 8,369,326 B2 | 2/2013 | Ansari et al. |
| 8,374,586 B2 | 2/2013 | Bentkovski |
| 8,375,657 B2 | 2/2013 | Buchwald et al. |
| 8,386,465 B2 | 2/2013 | Ansari et al. |
| 8,391,299 B2 | 3/2013 | Schliserman et al. |
| 8,397,264 B2 | 3/2013 | Ansari et al. |
| 8,422,397 B2 | 4/2013 | Ansari et al. |
| 8,459,119 B2 | 6/2013 | Miyamoto et al. |
| 8,461,413 B2 | 6/2013 | Frankard |
| 8,508,340 B2 | 8/2013 | Sanchez |
| 8,510,133 B2 | 8/2013 | Peak |
| 8,516,118 B2 | 8/2013 | Saint Clair |
| 8,543,665 B2 | 9/2013 | Ansari et al. |
| 8,577,739 B2 | 11/2013 | Ansari et al. |
| 8,583,055 B2 | 11/2013 | Park |
| 8,600,776 B2 | 12/2013 | Raduchel |
| 8,621,588 B2 | 12/2013 | Yoshida |
| 8,649,386 B2 | 2/2014 | Ansari et al. |
| 8,654,936 B1 | 2/2014 | Eslambolchi |
| 8,665,885 B2 | 3/2014 | Pastorino et al. |
| 8,683,566 B1 * | 3/2014 | Gailloux ............. H04L 63/0876 726/7 |
| 8,694,523 B2 | 4/2014 | Lim et al. |
| 8,701,166 B2 | 4/2014 | Courtney |
| 8,738,921 B2 | 5/2014 | Gephart |
| 8,856,289 B2 | 10/2014 | Ansari et al. |
| 8,893,293 B1 | 11/2014 | Schmoyer |
| 8,910,299 B2 | 12/2014 | Michalske |
| 8,971,341 B2 | 3/2015 | Ansari et al. |
| 8,973,056 B2 | 3/2015 | Ellis et al. |
| 9,028,405 B2 | 5/2015 | Tran |
| 9,071,606 B2 | 6/2015 | Braun et al. |
| 9,083,798 B2 | 7/2015 | Cross et al. |
| 9,167,176 B2 | 10/2015 | Winter |
| 9,202,084 B2 | 12/2015 | Moore |
| 9,203,912 B2 | 12/2015 | Krishnaswarmy et al. |
| 9,253,150 B2 | 2/2016 | Ansari et al. |
| 9,270,492 B2 | 2/2016 | Ansari et al. |
| 9,325,540 B2 | 4/2016 | Zhang |
| 9,407,624 B1 | 8/2016 | Myers |
| 9,414,776 B2 | 8/2016 | Sillay |
| 9,426,151 B2 | 8/2016 | Richards et al. |
| 9,569,587 B2 | 2/2017 | Ansari et al. |
| 9,602,880 B2 | 3/2017 | Ansari et al. |
| 9,736,028 B2 | 8/2017 | Ansari et al. |
| 9,924,235 B2 | 3/2018 | Ansari et al. |
| 10,057,269 B1 | 8/2018 | Ellingson |
| 10,069,643 B2 | 9/2018 | Ansari et al. |
| 10,071,395 B2 | 9/2018 | Ansari et al. |
| 10,097,367 B2 | 10/2018 | Ansari et al. |
| 10,225,096 B2 | 3/2019 | Ansari et al. |
| 10,263,803 B2 | 4/2019 | Ansari et al. |
| 10,361,877 B2 | 7/2019 | Ansari et al. |
| 10,374,821 B2 | 8/2019 | Ansari et al. |
| 10,403,394 B2 | 9/2019 | Ansari et al. |
| 10,530,598 B2 | 1/2020 | Ansari et al. |
| 10,630,501 B2 | 4/2020 | Ansari et al. |
| 10,646,897 B2 | 5/2020 | Ansari et al. |
| 10,672,508 B2 | 6/2020 | Ansari et al. |
| 10,673,645 B2 | 6/2020 | Ansari et al. |
| 10,728,051 B2 | 7/2020 | Ansari et al. |
| 10,764,254 B2 | 9/2020 | Ford |
| 11,164,644 B2 | 11/2021 | Hong |
| 2001/0011284 A1 | 8/2001 | Humpleman |
| 2001/0025349 A1 | 9/2001 | Sharood |
| 2001/0041982 A1 | 11/2001 | Kawasaki |
| 2001/0048030 A1 | 12/2001 | Sharood |
| 2001/0049786 A1 | 12/2001 | Harrison et al. |
| 2001/0051996 A1 | 12/2001 | Cooper et al. |
| 2002/0021465 A1 | 2/2002 | Moore |
| 2002/0023131 A1 | 2/2002 | Wu et al. |
| 2002/0027504 A1 | 3/2002 | David |
| 2002/0033416 A1 | 3/2002 | Gerszberg |
| 2002/0035404 A1 | 3/2002 | Ficco |
| 2002/0046279 A1 | 4/2002 | Chung |
| 2002/0052915 A1 | 5/2002 | Amin-Salehi |
| 2002/0059425 A1 | 5/2002 | Belfiore |
| 2002/0059586 A1 | 5/2002 | Carney et al. |
| 2002/0060994 A1 | 5/2002 | Kovacs et al. |
| 2002/0065894 A1 | 5/2002 | Dalal et al. |
| 2002/0067376 A1 | 6/2002 | Martin |
| 2002/0069243 A1 | 6/2002 | Raverdy |
| 2002/0071440 A1 | 6/2002 | Cerami et al. |
| 2002/0078150 A1 | 6/2002 | Thompson |
| 2002/0103877 A1 | 8/2002 | Gagnon |
| 2002/0112047 A1 | 8/2002 | Kushwaha et al. |
| 2002/0120686 A1 | 8/2002 | Schell |
| 2002/0122410 A1 | 9/2002 | Kulikov et al. |
| 2002/0124257 A1 | 9/2002 | Ismagilov |
| 2002/0128930 A1 | 9/2002 | Nakamoto et al. |
| 2002/0133613 A1 | 9/2002 | Teng |
| 2002/0136226 A1 | 9/2002 | Christoffel et al. |
| 2002/0156688 A1 | 10/2002 | Horn |
| 2002/0169858 A1 | 11/2002 | Bellinger |
| 2002/0176404 A1 | 11/2002 | Girard |
| 2002/0184358 A1 | 12/2002 | Traversal et al. |
| 2002/0184620 A1 | 12/2002 | Davies et al. |
| 2003/0005112 A1 | 1/2003 | Kraitkremer |
| 2003/0012155 A1 | 1/2003 | Sayeedi |
| 2003/0023131 A1 | 1/2003 | Wu et al. |
| 2003/0023730 A1 | 1/2003 | Wengrovitz |
| 2003/0083961 A1 | 5/2003 | Bezos et al. |
| 2003/0095569 A1 | 5/2003 | Wengrovitz |
| 2003/0112755 A1 | 6/2003 | McDysan |

(56) References Cited

U.S. PATENT DOCUMENTS

| | | |
|---|---|---|
| 2003/0118726 A1 | 6/2003 | Nakayama |
| 2003/0104010 A1 | 7/2003 | Szeto et al. |
| 2003/0126207 A1 | 7/2003 | Creamer et al. |
| 2003/0135823 A1 | 7/2003 | Marejka |
| 2003/0140103 A1 | 7/2003 | Szeto et al. |
| 2003/0151621 A1 | 8/2003 | McEvilly |
| 2003/0169752 A1 | 9/2003 | Chen et al. |
| 2003/0171996 A1 | 9/2003 | Chen et al. |
| 2003/0185360 A1 | 10/2003 | Moore |
| 2003/0210770 A1 | 11/2003 | Krejcarek |
| 2003/0217110 A1 | 11/2003 | Weiss |
| 2003/0229900 A1 | 12/2003 | Reisman |
| 2003/0231641 A1 | 12/2003 | Ryoo |
| 2003/0237004 A1 | 12/2003 | Okamura |
| 2004/0001480 A1 | 1/2004 | Tanigawa et al. |
| 2004/0003070 A1 | 1/2004 | Fernald et al. |
| 2004/0005859 A1 | 1/2004 | Ghercioiu et al. |
| 2004/0006477 A1 | 1/2004 | Craner |
| 2004/0006769 A1 | 1/2004 | Ansari et al. |
| 2004/0010327 A1 | 1/2004 | Terashima |
| 2004/0019489 A1 | 1/2004 | Funk et al. |
| 2004/0030750 A1 | 2/2004 | Moore et al. |
| 2004/0031058 A1 | 2/2004 | Reisman |
| 2004/0032399 A1 | 2/2004 | Sekiguchi et al. |
| 2004/0047310 A1 | 3/2004 | Chen et al. |
| 2004/0047358 A1 | 3/2004 | Chen et al. |
| 2004/0052076 A1 | 3/2004 | Mueller |
| 2004/0060079 A1 | 3/2004 | Tanaka et al. |
| 2004/0062230 A1 | 4/2004 | Taylor et al. |
| 2004/0073867 A1 | 4/2004 | Kausik et al. |
| 2004/0078573 A1 | 4/2004 | Matsuyama |
| 2004/0114608 A1 | 6/2004 | Rao et al. |
| 2004/0114610 A1 | 6/2004 | Featherson |
| 2004/0128310 A1 | 7/2004 | Zmudzinski et al. |
| 2004/0133657 A1 | 7/2004 | Smith et al. |
| 2004/0136373 A1 | 7/2004 | Bareis |
| 2004/0140989 A1 | 7/2004 | Papageorge |
| 2004/0160969 A1 | 8/2004 | Moon et al. |
| 2004/0174858 A1 | 9/2004 | Caspi et al. |
| 2004/0174863 A1 | 9/2004 | Caspi et al. |
| 2004/0177376 A1 | 9/2004 | Caspi et al. |
| 2004/0203942 A1 | 10/2004 | Dehlin |
| 2004/0213273 A1 | 10/2004 | Ma |
| 2004/0215750 A1 | 10/2004 | Stilp |
| 2004/0218609 A1 | 11/2004 | Foster et al. |
| 2004/0228324 A1 | 11/2004 | Alexiou |
| 2004/0230695 A1 | 11/2004 | Anschutz et al. |
| 2004/0240389 A1 | 12/2004 | Bessis |
| 2004/0255048 A1 | 12/2004 | Lev Ran et al. |
| 2004/0255326 A1 | 12/2004 | Hicks, III et al. |
| 2004/0260427 A1 | 12/2004 | Wimsatt |
| 2005/0018612 A1 | 1/2005 | Fitzgerald |
| 2005/0025887 A1 | 2/2005 | Xin |
| 2005/0027887 A1 | 2/2005 | Zimler et al. |
| 2005/0038526 A1 | 2/2005 | Choi |
| 2005/0038875 A1 | 2/2005 | Park |
| 2005/0065855 A1 | 3/2005 | Geller |
| 2005/0066063 A1 | 3/2005 | Grigorovitch |
| 2005/0068938 A1 | 3/2005 | Wang |
| 2005/0071663 A1 | 3/2005 | Medvinsky |
| 2005/0076198 A1 | 4/2005 | Skomra et al. |
| 2005/0086479 A1 | 4/2005 | Ondet |
| 2005/0089052 A1 | 4/2005 | Chen et al. |
| 2005/0094621 A1 | 5/2005 | Acharya |
| 2005/0096753 A1 | 5/2005 | Arling |
| 2005/0107086 A1 | 5/2005 | Tell |
| 2005/0108091 A1 | 5/2005 | Sotak et al. |
| 2005/0141492 A1 | 6/2005 | Chan |
| 2005/0144616 A1 | 6/2005 | Hammond |
| 2005/0149922 A1 | 7/2005 | Vincent |
| 2005/0150697 A1 | 7/2005 | Altman et al. |
| 2005/0174950 A1 | 8/2005 | Ayyagari |
| 2005/0180396 A1 | 8/2005 | Lim |
| 2005/0190744 A1 | 9/2005 | Sun et al. |
| 2005/0190898 A1 | 9/2005 | Priest |
| 2005/0195752 A1 | 9/2005 | Amin-Salehi |
| 2005/0195802 A1 | 9/2005 | Klein |
| 2005/0198040 A1 | 9/2005 | Cohen |
| 2005/0208948 A1 | 9/2005 | Hori |
| 2005/0210064 A1 | 9/2005 | Caldini |
| 2005/0216302 A1 | 9/2005 | Raji |
| 2005/0216580 A1 | 9/2005 | Raji |
| 2005/0216949 A1 | 9/2005 | Candelora et al. |
| 2005/0220081 A1 | 10/2005 | Urquizo |
| 2005/0222933 A1 | 10/2005 | Wesby |
| 2005/0226158 A1 | 10/2005 | Takahashi |
| 2005/0232284 A1 | 10/2005 | Karaoguz et al. |
| 2005/0240680 A1 | 10/2005 | Costa-Requena et al. |
| 2005/0240943 A1 | 10/2005 | Smith et al. |
| 2005/0257039 A1 | 11/2005 | Marshall |
| 2005/0260996 A1 | 11/2005 | Groenendaal |
| 2005/0262257 A1 | 11/2005 | Major |
| 2005/0273790 A1 | 12/2005 | Kearney, III et al. |
| 2005/0286466 A1 | 12/2005 | Tagg |
| 2006/0020589 A1 | 1/2006 | Wu |
| 2006/0025132 A1 | 2/2006 | Karoguz et al. |
| 2006/0029007 A1 | 2/2006 | Ayyagari |
| 2006/0029064 A1 | 2/2006 | Rao et al. |
| 2006/0031406 A1 | 2/2006 | Watson et al. |
| 2006/0031476 A1 | 2/2006 | Mathes et al. |
| 2006/0040667 A9 | 2/2006 | Coppinger et al. |
| 2006/0041926 A1 | 2/2006 | Istvan |
| 2006/0041936 A1 | 2/2006 | Anderson |
| 2006/0067344 A1 | 3/2006 | Sakurai |
| 2006/0075108 A1 | 4/2006 | Sylvain |
| 2006/0075276 A1 | 4/2006 | Kataria |
| 2006/0075429 A1 | 4/2006 | Istvan |
| 2006/0080352 A1 | 4/2006 | Boubez et al. |
| 2006/0104432 A1 | 5/2006 | Evslin |
| 2006/0122976 A1 | 6/2006 | Baluja et al. |
| 2006/0136246 A1 | 6/2006 | Tu |
| 2006/0142968 A1 | 6/2006 | Han |
| 2006/0146784 A1 | 7/2006 | Karpov et al. |
| 2006/0153214 A1 | 7/2006 | Moore et al. |
| 2006/0154642 A1 | 7/2006 | Scannell |
| 2006/0159116 A1 | 7/2006 | Gerszberg |
| 2006/0164205 A1 | 7/2006 | Buckingham |
| 2006/0167985 A1 | 7/2006 | Albanese |
| 2006/0174289 A1 | 8/2006 | Theberge |
| 2006/0178943 A1 | 8/2006 | Rollinson et al. |
| 2006/0206565 A1 | 9/2006 | Ganesan |
| 2006/0209857 A1 | 9/2006 | Hicks, III et al. |
| 2006/0220830 A1 | 10/2006 | Bennett |
| 2006/0227724 A1 | 10/2006 | Thubert et al. |
| 2006/0229746 A1 | 10/2006 | Ollis |
| 2006/0239425 A1 | 10/2006 | Hurst |
| 2006/0253894 A1 | 11/2006 | Bookman |
| 2006/0256759 A1 | 11/2006 | Sayeedi |
| 2006/0258396 A1 | 11/2006 | Matsuoka |
| 2006/0259584 A1 | 11/2006 | Watson et al. |
| 2006/0271695 A1 | 11/2006 | Lavian |
| 2006/0288112 A1 | 12/2006 | Soelberg |
| 2006/0291506 A1 | 12/2006 | Cain |
| 2006/0293965 A1 | 12/2006 | Burton |
| 2007/0005766 A1 | 1/2007 | Singhal et al. |
| 2007/0021867 A1 | 1/2007 | Woo |
| 2007/0036303 A1 | 2/2007 | Lee et al. |
| 2007/0038637 A1 | 2/2007 | Taneja |
| 2007/0043476 A1 | 2/2007 | Richards et al. |
| 2007/0043478 A1 | 2/2007 | Ehlers et al. |
| 2007/0049342 A1 | 3/2007 | Mayer et al. |
| 2007/0050351 A1 | 3/2007 | Kasperski et al. |
| 2007/0055759 A1 | 3/2007 | McCoy |
| 2007/0058608 A1 | 3/2007 | Lin |
| 2007/0058644 A1 | 3/2007 | Brahmbhatt et al. |
| 2007/0061149 A1 | 3/2007 | Chang |
| 2007/0066490 A1 | 3/2007 | Gemelos |
| 2007/0100981 A1 | 5/2007 | Adamczyk et al. |
| 2007/0106570 A1 | 5/2007 | Hartman et al. |
| 2007/0109976 A1 | 5/2007 | Samanta et al. |
| 2007/0115922 A1 | 5/2007 | Schneider et al. |
| 2007/0133763 A1 | 6/2007 | D'angelo |
| 2007/0143262 A1 | 6/2007 | Kasperski |
| 2007/0143831 A1 | 6/2007 | Pearson |

(56) References Cited

U.S. PATENT DOCUMENTS

| | | |
|---|---|---|
| 2007/0147420 A1 | 6/2007 | Dean |
| 2007/0150286 A1 | 6/2007 | Miller |
| 2007/0150345 A1 | 6/2007 | Tonse et al. |
| 2007/0216764 A1 | 6/2007 | Kwak |
| 2007/0156265 A1 | 7/2007 | McCoy |
| 2007/0157285 A1 | 7/2007 | Frank |
| 2007/0165629 A1 | 7/2007 | Chaturvedi et al. |
| 2007/0169144 A1 | 7/2007 | Chen |
| 2007/0171091 A1 | 7/2007 | Nisenboim |
| 2007/0171895 A1 | 7/2007 | Oberle et al. |
| 2007/0192477 A1 | 8/2007 | Hicks et al. |
| 2007/0192486 A1 | 8/2007 | Wilson |
| 2007/0192735 A1 | 8/2007 | Lehto |
| 2007/0198437 A1 | 8/2007 | Eisner et al. |
| 2007/0199022 A1 | 8/2007 | Moshiri |
| 2007/0220165 A1 | 9/2007 | Moorer |
| 2007/0241879 A1 | 10/2007 | Jobe |
| 2007/0250592 A1 | 10/2007 | Reckamp |
| 2007/0253443 A1 | 11/2007 | Dean, Jr. et al. |
| 2007/0273539 A1 | 11/2007 | Gananathan |
| 2007/0286159 A1 | 12/2007 | Preiss et al. |
| 2007/0291650 A1 | 12/2007 | Ormazabal |
| 2007/0294721 A1 | 12/2007 | Haeuser |
| 2007/0297454 A1 | 12/2007 | Brothers |
| 2008/0005306 A1 | 1/2008 | Kushalnagar |
| 2008/0005565 A1 | 1/2008 | Shiga |
| 2008/0022391 A1 | 1/2008 | Sax |
| 2008/0043719 A1 | 2/2008 | Pok |
| 2008/0052393 A1 | 2/2008 | McNaughton et al. |
| 2008/0062965 A1 | 3/2008 | Silva |
| 2008/0066126 A1 | 3/2008 | Walter |
| 2008/0069121 A1 | 3/2008 | Adamson et al. |
| 2008/0084789 A1 | 4/2008 | Altman et al. |
| 2008/0084888 A1 | 4/2008 | Yadav et al. |
| 2008/0098212 A1 | 4/2008 | Helms |
| 2008/0101320 A1 | 5/2008 | Krahn et al. |
| 2008/0115162 A1 | 5/2008 | Yu et al. |
| 2008/0123683 A1 | 5/2008 | Cheng et al. |
| 2008/0127063 A1 | 5/2008 | Silva |
| 2008/0130666 A1 | 6/2008 | Kawamoto et al. |
| 2008/0134258 A1 | 6/2008 | Goose |
| 2008/0141315 A1 | 6/2008 | Ogilvie |
| 2008/0144642 A1 | 6/2008 | Song |
| 2008/0147205 A1 | 6/2008 | Ollis |
| 2008/0151778 A1 | 6/2008 | Venkitaraman et al. |
| 2008/0155613 A1 | 6/2008 | Benya |
| 2008/0163059 A1 | 7/2008 | Craner |
| 2008/0166048 A1 | 7/2008 | Raif et al. |
| 2008/0177856 A1 | 7/2008 | Howard |
| 2008/0178236 A1 | 7/2008 | Hoshall |
| 2008/0221715 A1 | 9/2008 | Krzyzanowski |
| 2008/0239957 A1 | 10/2008 | Tokura |
| 2008/0240125 A1 | 10/2008 | Purvis et al. |
| 2008/0272934 A1 | 11/2008 | Wang |
| 2008/0304500 A1 | 12/2008 | Schliserman et al. |
| 2009/0034419 A1 | 2/2009 | Flammer et al. |
| 2009/0077207 A1 | 3/2009 | Karaoguz et al. |
| 2009/0100460 A1 | 4/2009 | Hicks |
| 2009/0178079 A1 | 7/2009 | Berger |
| 2009/0180422 A1 | 7/2009 | Brundridge et al. |
| 2009/0189774 A1 | 7/2009 | Brundridge et al. |
| 2009/0216847 A1 | 8/2009 | Krishnaswamy et al. |
| 2010/0014444 A1 | 1/2010 | Ghanadan et al. |
| 2010/0030734 A1 | 2/2010 | Chunilal |
| 2010/0061309 A1 | 3/2010 | Buddhikot et al. |
| 2010/0071053 A1 | 3/2010 | Ansari et al. |
| 2010/0142692 A1 | 6/2010 | Gotta |
| 2010/0153730 A1 | 6/2010 | Goria |
| 2010/0205152 A1 | 8/2010 | Ansari et al. |
| 2010/0211636 A1 | 8/2010 | Starkenburg |
| 2010/0238810 A1 | 9/2010 | Ormazabal |
| 2010/0241711 A1 | 9/2010 | Ansari et al. |
| 2010/0291940 A1 | 11/2010 | Koo |
| 2011/0019135 A1 | 1/2011 | Koganezawa |
| 2011/0092232 A1 | 4/2011 | Lee |
| 2011/0182205 A1 | 7/2011 | Gerdes et al. |
| 2012/0060181 A1 | 3/2012 | Craner |
| 2012/0101881 A1 | 4/2012 | Taylor et al. |
| 2012/0110490 A1 | 5/2012 | Keller |
| 2012/0157043 A1 | 6/2012 | LaJoie |
| 2012/0311665 A1 | 12/2012 | Lim |
| 2013/0191871 A1 | 7/2013 | Gilboy |
| 2013/0329745 A1 | 12/2013 | Phillips et al. |
| 2014/0362253 A1 | 12/2014 | Kim |
| 2015/0074259 A1 | 3/2015 | Ansari et al. |
| 2015/0208363 A1 | 7/2015 | Funk et al. |
| 2016/0226823 A1 | 8/2016 | Ansari et al. |
| 2016/0226920 A1 | 8/2016 | Ansari et al. |
| 2016/0344745 A1 | 11/2016 | Johnson et al. |
| 2017/0078154 A1 | 3/2017 | Ansari et al. |
| 2017/0344703 A1 | 11/2017 | Ansari et al. |
| 2018/0123819 A1 | 5/2018 | Ansari et al. |
| 2018/0131571 A1 | 5/2018 | Ansari et al. |
| 2018/0131572 A1 | 5/2018 | Ansari et al. |
| 2018/0152310 A1 | 5/2018 | Ansari et al. |
| 2018/0198692 A1 | 7/2018 | Ansari et al. |
| 2018/0227140 A1 | 8/2018 | Ansari et al. |
| 2018/0361426 A1 | 12/2018 | Ansari et al. |
| 2019/0312745 A1 | 10/2019 | Ansari et al. |
| 2019/0358669 A1 | 11/2019 | Ansari et al. |
| 2019/0363903 A1 | 11/2019 | Ansari et al. |
| 2019/0372797 A1 | 12/2019 | Ansari et al. |
| 2020/0009612 A1 | 1/2020 | Ansari et al. |
| 2020/0059377 A1 | 2/2020 | Ansari et al. |
| 2020/0076638 A1 | 3/2020 | Ansari et al. |
| 2020/0176095 A1 | 6/2020 | Ansari et al. |
| 2020/0228363 A1 | 7/2020 | Ansari et al. |
| 2020/0228364 A1 | 7/2020 | Ansari et al. |
| 2021/0194715 A1 | 6/2021 | Ansari et al. |
| 2021/0211320 A1 | 7/2021 | Ansari et al. |
| 2021/0218571 A1 | 7/2021 | Ansari et al. |
| 2021/0344521 A1 | 11/2021 | Ansari et al. |
| 2021/0409239 A1 | 12/2021 | Ansari et al. |
| 2022/0021552 A1 | 1/2022 | Ansari et al. |
| 2022/0103393 A1 | 3/2022 | Ansari et al. |

FOREIGN PATENT DOCUMENTS

| | | |
|---|---|---|
| DE | 3818631 A1 | 12/1989 |
| DE | 9116206 U1 | 4/1992 |
| DE | 19723596 C1 | 10/1998 |
| DE | 10024525 A1 | 11/2001 |
| DE | 20304806 U1 | 8/2003 |
| EP | 0805254 A2 | 11/1997 |
| EP | 0921260 A2 | 6/1999 |
| EP | 1113659 A2 | 7/2001 |
| EP | 1195497 A2 | 4/2002 |
| EP | 1377005 A1 | 1/2004 |
| EP | 1394986 A1 | 3/2004 |
| EP | 1657396 A2 | 5/2006 |
| JP | 07104063 A | 4/1995 |
| JP | 03269387 B2 | 3/2002 |
| JP | 2002139565 A | 5/2002 |
| WO | WO0193533 A2 | 12/2001 |
| WO | WO2005111653 A2 | 11/2005 |
| WO | WO2007004921 A1 | 1/2007 |
| WO | WO2008021665 A2 | 2/2008 |
| WO | WO2008082346 A1 | 7/2008 |
| WO | WO2008082441 A1 | 7/2008 |
| WO | WO2008083384 A2 | 7/2008 |
| WO | WO2008083385 A1 | 7/2008 |
| WO | WO2008083387 A2 | 7/2008 |
| WO | WO2008083391 A2 | 7/2008 |
| WO | WO2008085201 A2 | 7/2008 |
| WO | WO2008085202 A1 | 7/2008 |
| WO | WO2008085203 A2 | 7/2008 |
| WO | WO2008085204 A2 | 7/2008 |
| WO | WO2008085205 A2 | 7/2008 |
| WO | WO2008085206 A2 | 7/2008 |
| WO | WO2008085207 A2 | 7/2008 |
| WO | WO2008085205 A3 | 9/2008 |
| WO | WO2008085204 A3 | 10/2008 |
| WO | WO2008085207 A3 | 10/2008 |
| WO | WO2008085203 A3 | 11/2008 |

(56) References Cited

FOREIGN PATENT DOCUMENTS

| WO | WO2008085206 A3 | 11/2008 |
|---|---|---|
| WO | WO2009036088 A1 | 3/2009 |
| WO | WO2009036185 A1 | 3/2009 |
| WO | WO2009086134 A1 | 7/2009 |

OTHER PUBLICATIONS

"Apple Releases QuickTime 5 and QuickTime Streaming Server 3 Public Previews," Apple Press Release, Oct. 10, 2000, 3 pages.
"Microsoft Introduces New Interactive Program Guide Solution to Improve Digital Cable TV Experience," Microsoft, May 6, 2002, 4 pages.
"Microsoft WebTV Networks Announces Pricing for UltimateTV Service," PressPass, Microsoft, Oct. 26, 2000, 2 pages.
"QuickTime 4.0 Plays MP3," Wired, Apr. 14, 1999, 3 pages.
"QuickTime 6.4 User's Guide," Apple Computer, Inc.,2003, 50 pages.
"QuickTime 7 User's Guide," Apple Computer, Inc., 2005, 62 pages.
"RealNetworks Releases RealPlayer 10, the best Media Player Ever," E-Channel News, Jan. 7, 2004, 4 pages.
"Vulnerability in Windows Media Services Could Allow a Denial of Service," Microsoft Security Bulletin, MS04-008, Mar. 9, 2004, 12 pages.
"Windows Media Services 4.1," Microsoft, 2000, 3 pages.
Akst, D., "The Cutting Edge: Computing/Technology/Innovation: The Hear and Now of Making Sound on the Internet," Los Angeles Times, Jun. 28, 1995, 8 pages.
Apple TV Setup Guide, 2008, 37 pages.
Lane, S., "Disney chief talks up Apple's iTV media hub," AppleInsider, 13 pages.
Mattson, W., "QuickTime 4 ready for prime time," ZDNet, Jun. 9, 1999, 5 pages.
Perez, C., "Microsoft TV (IPTV) is here," Academy Florida, Jan. 9, 2006, 10 pages.
Sheesley, J., "Add Streaming Media Capability to Your Windows NT Server," TechRepublic, May 13, 2002, 11 pages.
Transcription of Apple Showtime Event 2006—The iTV Introduction (Pt. 1) <https://www.youtube.com/watch?v=X_oz3DdLkG4>, including screenshots of Apple devices, GUI's, and menus from video (2006), 13 pages.
U.S. Appl. No. 17/000,067 for Ansari et al., filed Aug. 21, 2020.
U.S. Appl. No. 17/019,930 for Ansari et al., filed Sep. 14, 2020.
DLNA enables streaming of premium video in connected homes across Europe. (New Products) IPTV Newsletter, v 5, n 10, p. 4 Oct. 2011.
Dueans, J.C., "An End-to-End Service Provisioning Scenario for the Residential Environment," IEEE Communications Magazine, Sep. 2005, pp. 94-100.
Ganguly, A., et al., "IP over P2P: enabling self-configuring virtual IP networks for grid computing," in Parallel and Distributed Processing symposium, 20060 IPDPS 2006, April 25-29, retrieved on Jan. 20, 2010, retrieved from the internet http://aarxiv.org/PS_cache/cs/pdf/0603/0603087v1.pdf.
Haerick W. et al., "Success in Home Service Deployment: Zero-Touch or Chaos?", British Telecommunications, Jul. 1, 2007, pp. 36-43, vol. 5, No. 3, London, GB.
Il-Woo Lee, et al., "A Proposed Platform & Performance Estimation of Digital-Home Service Delivery/Management Systems," Apr. 10, 2006, pp. 713-719, Information Technology: New Generations, 2006.
Intel, "Delivering on the Promise of Triple Play Digital Media," Technology Backgrounder, Consumer Electronics, 2004, pp. 1-4.
International Application No. PCT/US2008/087724, filed Dec. 19, 2008, 7 Pages, 1211 Geneva 20, Switzerland.
International Search Report and the Written Opinion of the International Searching Authority issued in International Application No. PCT/US2008/087724 dated Feb. 17, 2009.
International Search Report and the Written Opinion of the International Searching Authority issued in International Patent Application No. PCT/US08/75889 dated Nov. 24, 2008.
International Search Report and Written Opinion in International Application No. PCT/US05/15860, dated Jul. 17, 2006, 8 pages.
International Search Report and Written Opinion in International Application No. PCT/US08/76036, dated Nov. 14, 2008.
International Search Report in International Application No. PCT/JP2008/051225, dated Feb. 19, 2008.
International Search Report dated Apr. 25, 2008, International Application No. PCT/US2007/019531, filed Sep. 7, 2007, 1 page.
International Search Report dated Aug. 21, 2008, International Application No. PCT/US2007/019534, filed Sep. 7, 2007, 1 page.
International Search Report dated Aug. 25, 2008, International Application No. PCT/US2007/019545, filed Sep. 7, 2007, 1 page.
International Search Report dated August 27, 2008, International Application No. PCT/US2007/089237, filed Dec. 31, 2007, 6 pages.
International Search Report dated Jul. 14, 2008, International Application No. PCT/US2007/019546, filed Sep. 7, 2007, 1 page.
International Search Report dated July 17, 2008, International Application No. PCT/US2007/019543, filed Sep. 7, 2001, 1 page.
International Search Report dated Jul. 2, 2008, International Application No. PCT/US2007/019544, filed Sep. 7, 2007, 1 page.
International Search Report dated Mar. 14, 2008, International Application No. PCT/US2007/019533, filed Sep. 7, 2007, 1 page.
Machine Translation of JP11290082-A, Oct. 1999.
Notification of Transmittal of the International Search Report and the Written Opinion of the International Searching Authority, or the Declaration dated August 27, 2008, 24 pages, Application No. PCT/US2007/089232.
Notification of Transmittal of the International Search Report and the Written Opinion of the International Searching Authority, or the Declaration dated Aug. 8, 2008, 22 pages, Application No. PCT/US2007/089227.
Notification of Transmittal of the International Search Report and the Written Opinion of the International Searching Authority, or the Declaration dated Oct. 22, 2008, 12 pages, Application No. PCT/US2007/089232.
Notification of Transmittal of the International Search Report and the Written Opinion of the International Searching Authority, or the Declaration, dated Feb. 26, 2008, 11 pages, Application No. PCT/US07/19483.
Notification of Transmittal of the International Search Report and the Written Opinion of the International Searching Authority, or the Declaration, dated Mar. 14, 2008, 12 pages, Application No. PCT/US07/19533.
PCT Invitation to Pay Additional Fees and, where Applicable, Protest Fee (PCT/ISA/206) and Communication Relating to the Results of the Partial International Search (Annex to PCT/ISA/206) dated May 19, 2008 for PCT Application No. PCT/US2007/089237, 7 pages.
PCT Invitation to Pay Additional Fees and, where Applicable, Protest Fee (PCT/ISA/206) and Communication Relating to the Results of the Partial International Search (Annex to PCT/ISA/206) dated May 21, 2008 for PCT Application No. PCT/US2007/089227, 7 pages.
Technology and challenges of virtual communities. International Journal of Business Research, v 7, n 4, p. 69 Jul. 2007.
Wen-Shyang Hwang et al., "A QoS-aware Residential Gateway with Bandwidth Management," Aug. 2005.
Written Opinion of the International Searching Authority dated Apr. 25, 2008, International Application No. PCT/US2007/019531, filed Sep. 7, 2007, 7 pages.
Written Opinion of the International Searching Authority dated Aug. 21, 2008, International Application No. PCT/US2007/019534, filed Sep. 7, 2007, 5 pages.
Written Opinion of the International Searching Authority dated Aug. 25, 2008, International Application No. PCT/US2007/019545, filed Sep. 7, 2007, 5 pages.
Written Opinion of the International Searching Authority dated Jul. 14, 2008, International Application No. PCT/US2007/019546, filed Sep. 7, 2007, 5 pages.

(56) References Cited

OTHER PUBLICATIONS

Written Opinion of the International Searching Authority dated Jul. 17, 2008, International Application No. PCT/US2007/019543, filed Sep. 7, 2007, 5 pages.
Written Opinion of the International Searching Authority dated Jul. 2, 2008, International Application No. PCT/US2007/019544, filed Sep. 7, 2007, 5 pages.
Written Opinion of the International Searching Authority dated Mar. 14, 2008, International Application No. PCT/US2007/19533, filed Sep. 7, 2007, 7 pages.
Written Opinion of the International Searching Authority dated Aug. 27, 2008, International Application No. PCT/US2007/089237, filed Dec. 31, 2007, 15 pages.
Yeon-Joo, O. et al., "Design of a SIP-based Real-time Visitor Conversation and Door Control Architecture using a Home Gateway," Consumer Electronics, 2006, ICCE '06, 2006 Digest of Technical Papers, International Conference, Las Vegas, NV, USA, IEEE, Jan. 7, 2006, pp. 187-188.
Young-Gab Kim et al., A Service Bundle Authentication Mechanism in the OSGI Service Platform, Advanced Information Networking and Applications, 2004, AINA 2004. 18th International Conference on Fukuoka, Japan, Mar. 29-31, 2004, Piscataway, NJ, USA, IEEE, vol. 1, Mar. 29, 2004, pp. 420-425.
U.S. Appl. No. 16/842,518 for Ansari et al., filed Apr. 7, 2020.
U.S. Appl. No. 16/889,347 for Ansari et al., filed Jun. 1, 2020.
U.S. Appl. No. 16/900,487 for Ansari et al., filed Jun. 12, 2020.
U.S. Appl. No. 17/491,440 for Ansari et al., filed Sep. 30, 2021.
U.S. Appl. No. 17/498,731 for Ansari et al., filed Oct. 11, 2021.
U.S. Appl. No. 17/506,451 for Ansari et al., filed Oct. 20, 2021.
U.S. Appl. No. 17/516,352 for Ansari et al., filed Nov. 1, 2021.
U.S. Appl. No. 17/706,105 for Ansari et al., filed Mar. 28, 2022.
U.S. Appl. No. 17/701,943 for Ansari et al., filed Mar. 23, 2022.

\* cited by examiner

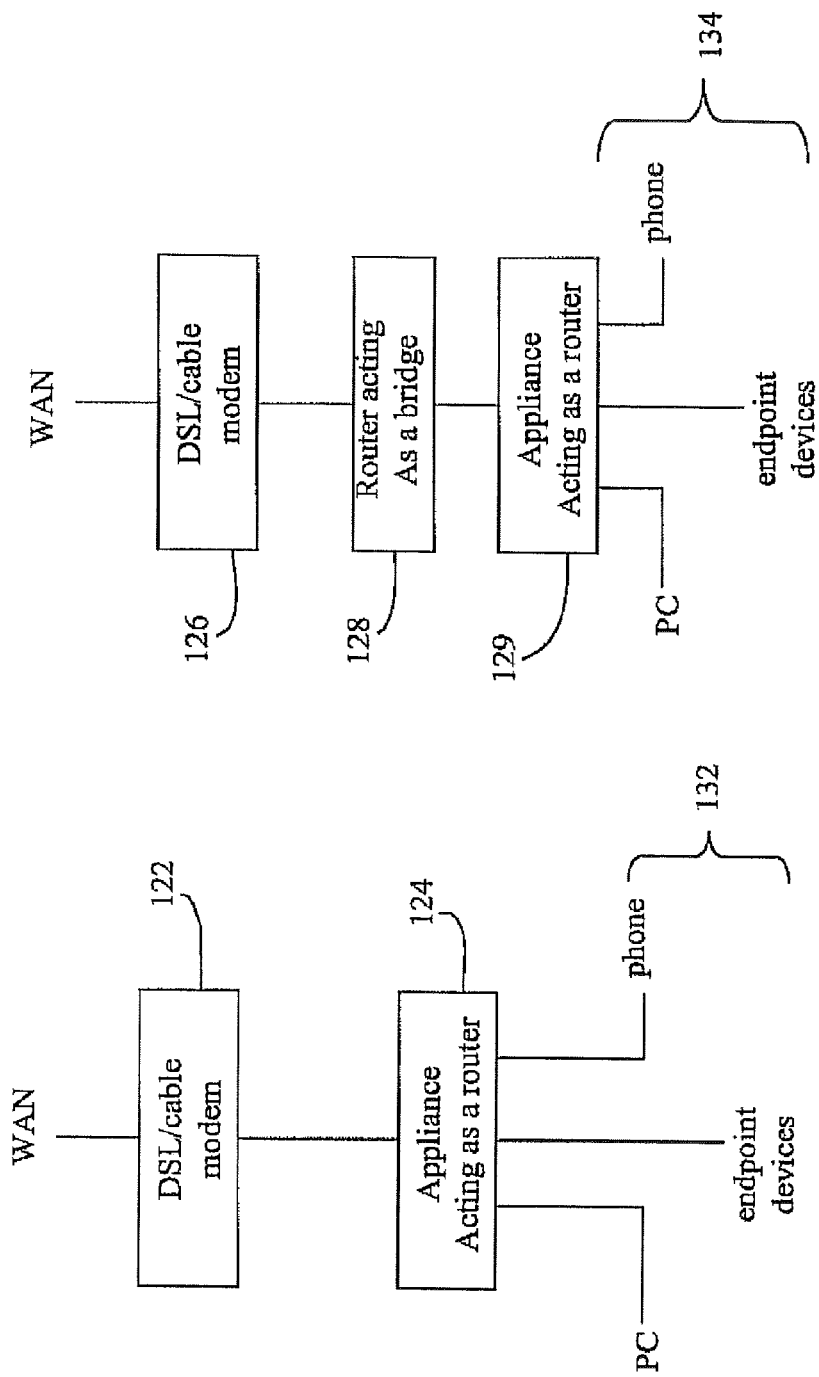

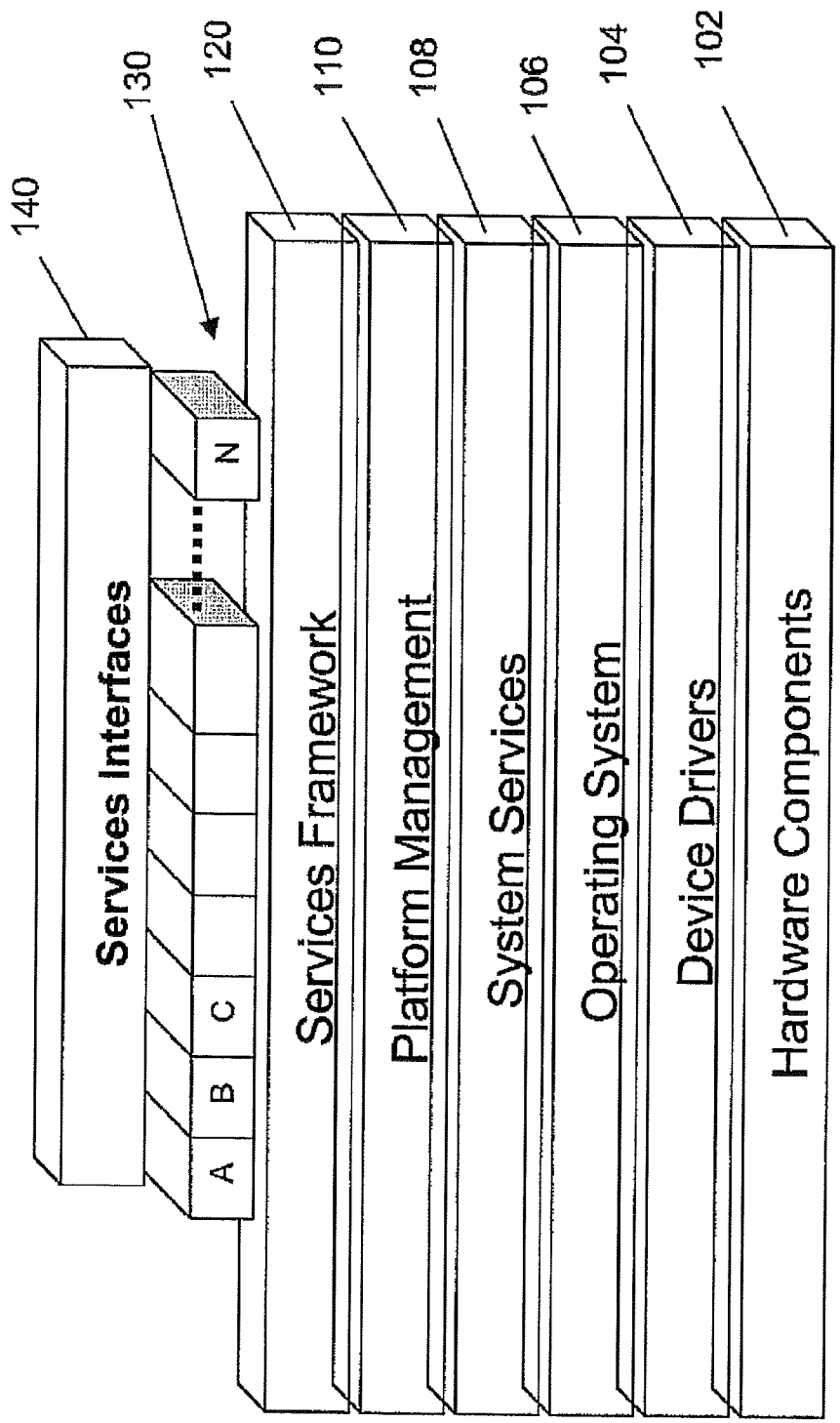

MULTI-SERVICES APPLICATION GATEWAY AND SYSTEM EMPLOYING THE SAME

CROSS-REFERENCE TO RELATED APPLICATIONS

This application is a continuation application of U.S. patent application Ser. No. 16/514,803, filed Jul. 17, 2019, which is a continuation of U.S. patent application Ser. No. 15/214,416, filed Jul. 19, 2016, now U.S. Pat. No. 10,403,394, which is a continuation application of U.S. patent application Ser. No. 14/294,957, filed Jun. 3, 2014, now U.S. Pat. No. 9,569,587, which is a continuation application of U.S. patent application Ser. No. 14/024,362, filed Sep. 11, 2013, which is a continuation-in-part application of U.S. patent application Ser. No. 12/521,757, filed Apr. 28, 2010, now U.S. Pat. No. 8,543,665, which is a U.S. National Phase Application under 35 C.F.R 371 of International Application No. PCT/US2007/089237, filed Dec. 31, 2007, which claims the benefit of U.S. Provisional Application No. 60/882,862, filed Dec. 29, 2006 and U.S. Provisional Application No. 60/882,865, filed Dec. 29, 2006, the disclosures of which are all incorporated by reference herein in their entireties for their teaching including any references cited therein.

FIELD OF THE INVENTION

The present invention relates generally to manage services for supporting and managing the emerging digital home, and more particularly, to a gateway appliance for providing managed services to the home.

BACKGROUND

The digital home is now becoming more complex with the myriad of new and emerging digital devices intended to address many user and consumer needs such as communication, entertainment, privacy, and security, etc. However, given the complexity of the emerging digital home and digital environments generally, users who are technologically challenged may find it a daunting and intimidating task to manage their home networks and interconnected digital devices. Moreover, new paradigms are emerging oriented to delivering media content to and the consuming of media content at the home. The protection of received Internet-sourced media content in additional to user-generated media content is additionally an important aspect that may be inadequately addressed by the technologically challenged user. Furthermore, with respect to Internet based data while most of the content delivery solutions are provided to the digital home networks through availability of the "two-foot" interface (i.e., the PC), it is relatively cumbersome to bring this content to the "ten-foot" interface (e.g., the television).

In addition to hardware limitations, there is a lack of meaningful direction and "coaching" leveraging new information technology that are now becoming available for use in the home or small enterprise, thereby limiting the ability of the user to improve their lives, make the "right" decisions, or meet domain-specific objectives such as smarter nutrition, meeting exercise targets, medication regimen conformance, disciplined financial actions, etc., with the explosion of connected devices, personal and home sensors, and access to user and family data provides improved self-visibility of behavior and performance to the user. Existing solutions and services (home automation, energy management, media services, exercise, e-health solutions, financial management program, presence programs, etc.) are "siloed", not integrated, with other aspects of the user's life, don't fully leverage the influence of social media friends, don't enable users to develop personalized objectives, and don't provide expert-level coaching. At the same time, users are exposed to advertising and offers/incentives that may or may not be relevant to the moment, and may not be complementary to the users' overarching objectives, and may compromise a users' private and confidential information.

What is needed are solutions for providing managed services for supporting and managing the emerging digital home including providing a gateway appliance that can offer managed services to its users to include incorporation of a causation and correlation engine abilities that enable broader services for users.

SUMMARY

In accordance with features of the present invention, solutions are provided for providing managed services for supporting and managing the emerging digital home including providing a gateway appliance that can offer managed services to its users to include incorporation of a causation and correlation engine abilities that enable broader services for users. Examples of areas where useful objectives may be established include: Financial Objectives, Health/Medical Objectives, Exercise Objectives, Nutrition Objectives, Advertising Objectives, Home Security Objectives, Purchasing Objectives, Energy Conservation Objectives, etc.

In accordance with features of the present invention, a media manager residing at a user can include a video retrieval module operable to retrieve and capture video activity of at least one media display device as a video activity stream, and a media management module coupled to the video retrieval module and the at least one media display device is operable to receive the video activity stream. The media management module can be further operable to receive a user command to view the video activity stream at a selected other media display device coupled to the media management module, and direct the video activity stream to the selected other media display device.

In accordance with features of the present invention, a gateway device residing at a user premises can include an application service module having at least one application, the application service module residing on a user premises side of a network service provider demarcation, a user module having a user interface that can be associated with the at least one application, wherein the user module enables bi-directional communications with at least one media player device, a network module having the connection that enables bi-directional communications with a remote service manager, a video retrieval module operable to retrieve and capture video activity of at least one media display device as a video activity stream, and a media management module coupled to the video retrieval module and the at least one media display device, and being operable to receive the video activity stream. The media management module can be further operable to receive a user command to view the video activity stream at a selected other media display device coupled to the media management module, and direct the video activity stream to the selected other media display device. The gateway device may have router functionality integrated within the gateway or the router functionality may be provided by a separate physical device within the premise.

In accordance with features of the present invention, a media manager can include a tuner coupled to at least one media source operable to selectively receive at least one media stream of at least one type of media content, a media processor coupled to the tuner and operable to receive the at least one media stream and convert the media stream to a predetermined data format, the at least one media stream comprising metadata, a media management module coupled to the media processor and operable to receive the at least one media stream in the predetermined data format, and direct the media stream to a first predetermined media player device coupled to the media processor. The media management module is operable to receive a selection of a media content by a first user from a first predetermined media player device to determine whether the metadata of the selected media content comprises user control parameters associated therewith, to send a notification to a second predetermined media player device to obtain permission, and to stream the selected media content to the first predetermined media player device only in response to receiving permission from a second user with authority over the user control parameters.

In accordance with features of the present invention, a method of monitoring activity on a first media display device at a user premises can include receiving, at a gateway device, a stream of media content in response to a first user's request input at a first media display device, the media content comprising metadata, sending to a second media display device a notification with predetermined elements of the metadata seeking authorization to stream the media content to the first media display device, and streaming the requested media content to the first media display device only in response to an authorization notification being received by the gateway device. The gateway device comprises a LAN connection by which the gateway can be coupled to media display devices and a media storage device, and an application service module enabling the gateway device to receive and stream media to selected media display devices associated with the gateway device and to send and receive digital notification to and from the media display devices.

In accordance with features of the present invention, a gateway device for operation at a user premise can have at least one endpoint device associated with the gateway device, the gateway device being in communication with a remote service manager, the gateway device can include an application service module having at least one application, the application service module being remotely managed by a remote service manager via a connection, a user module having a user interface that can be associated with the at least one application, wherein the user module enables bi-directional communications with the at least one endpoint device, a network module having the connection that enables bi-directional communications with the remote service manager, and a processor coupled to the user module, application service module, and network module, wherein the processor comprises an accessibility testing module operable to verify network signaling accessibility to the gateway device by at least one remote endpoint device.

In accordance with features of the present invention, a method of verifying network signaling accessibility to a first gateway device by at least one remote device can be provided, where the method can include sending a message regarding access details to the at least one remote device coupled via a WAN to the first gateway device, testing accessibility using a publicly available communication protocol, sending the results of the accessibility test information to the first gateway device, and if the test is successful, updating data on a storage device coupled to the first gateway device.

In accordance with features of the present invention, a system having at least one remote service manager coupled to a network can be provided. The system can further have at least one gateway device disposed at a user premises and in communication with the at least one remote service manager through a network module coupled to the network. The at least one gateway device having at least one application performing traditional central office functions for voice services and logically positioned on the user premises side of the network service provider demarcation. The system can also have at least one endpoint device disposed at the user premises and in communication through a user module with the at least one gateway device. The at least one endpoint device can be operable to generate, through the at least one gateway device, a message by executing the at least one application performing traditional central office functions for voice services. Furthermore, the system has a voice service manager disposed at the at least one remote service manager, the voice manager being configured to deliver the message from the network to a second network. The at least one gateway device can be operable to enable, under the control of the at least one remote service manager, the at least one endpoint device to generate, maintain, and terminate the message.

In accordance with features of the present invention, a method can be provided for enabling an endpoint device to communicate through at least one gateway device to conduct a telephone call wherein traditional central office based functions for voice services associated with the telephone call have been moved to the user premises. The method can involve configuring the at least one gateway device at a user premises by a remote service manager through a network module connected to a network with at least one application supporting traditional central office based functions for voice services. Furthermore, the method can include enabling the at least one gateway device to execute the at least one application supporting traditional central office based functions for voice services and disposed on the user premises side of a network service provider demarcation. Also, the method can include detecting and configuring a first endpoint device associated with the at least one gateway device capable of supporting voice services by the at least one gateway device, the first endpoint device executing the at least one application supporting traditional central office based functions for voice services. Additionally, the method can involve communicating through a user module by the first endpoint device with the at least one gateway device to access the at least one application supporting traditional central office based functions for voice services. The method can also include managing voice services through the remote service manager to enable the first endpoint device to communicate with a second endpoint device.

BRIEF DESCRIPTION OF THE FIGURES

Further features, aspects, and advantages of the structures and methods of the present invention will become better understood with regard to the following description, appended claims, and accompanying drawings where:

FIGS. 1B(1) and 1B(2) illustrate the gateway appliance connection to the in-premise devices in different embodiments;

FIGS. 2A-2C depict the software and hardware architectures of the multi-services applications gateway appliance 10 according to the present invention;

DETAILED DESCRIPTION

Figure 1A:
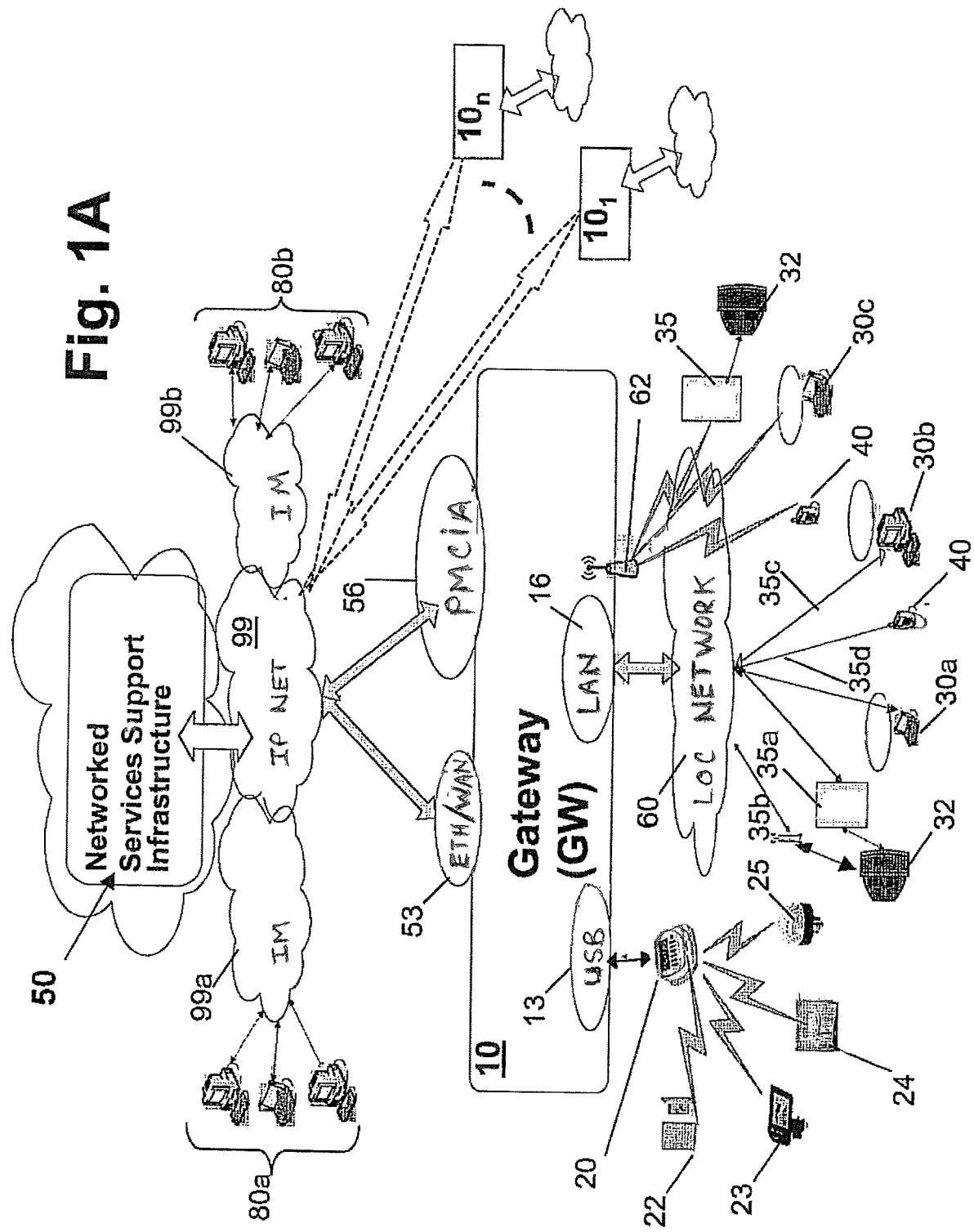
FIG. 1A depicts a multi-services applications gateway appliance 10 according to the present invention.

Applicant's issued U.S. Pat. No. 8,027,335 entitled MULTIMEDIA ACCESS DEVICE AND SYSTEM EMPLOYING THE SAME incorporated by reference herein, describes a media access device that facilitates communication between users employing disparate communication devices and messaging protocols associated with different service providers that is located within the customer premises and that allows for onsite or remote configuration. This solution is a highly specific implementation that provides advanced telephony particularly specific services associated with Voice over IP communications in an Instant Messaging infrastructure. While comprehensive, this system does not address the servicing and management of other digital endpoint devices in the home. Furthermore, this prior art solution requires manual intervention to initiate, configure, and maintain many of the call service, IM, and other service related features for users which can be burdensome for the technically challenged.

A significant demand exists for simplifying the management and back-up services of the digital home or even the small enterprise that takes away the complexity of the maintenance, upgrading, and operation of even the more basic needs addressed by these emerging digital endpoint devices and networks, e.g., access management (e.g., parental controls), etc.

Home "gateway" and like router/gateway appliances are currently available for the home and small business that allow several computers to communicate with one another and to share a broadband Internet connection. These devices function as routers by matching local network addresses and the hostnames of the local computers with the actual networking hardware detected. As gateways, these devices translate local network addresses to those used by the Internet for outgoing communications and do the opposite translation for incoming packets.

For example, U.S. Pat. No. 6,930,598 is representative of a home gateway server appliance enabling networked electronic devices to communicate with each other without the direct interaction with external networks and that provides a mechanism whereby a member of the household may be informed of certain network related events without having to use their home computer or other client devices.

It would be highly desirable to provide a multi-services application gateway device that provides not only IP-based communication and voice services, but services management capability associated with use of digital home devices, and obviates the need for users to attend to the provisioning, management, configuration, and maintenance of the emerging home/business digital networks including the myriad of interconnected digital endpoint devices connected thereto.

The present invention is directed to a novel gateway appliance that is programmed to simplify various aspects of managing the emerging home/business digital networks including the myriad of interconnected digital endpoint devices.

The novel gateway appliance is further programmed to simplify support services in the digital home including: media delivery, content management, access control and use tracking, file sharing, and protection and back-up services of both Internet/Web-generated digital media content and user generated digital media content.

The appliance of the present invention further operates in conjunction with a service delivery platform that provides IP-based connectivity to digital devices in the home, e.g., VoIP phones, the personal computer, personal music players, and the like, and emphasizes ease of use and management of these digital devices for the technically challenged.

The novel gateway appliance is further programmed to simplify home automation operations, e.g., lights, garage doors, and particularly, facilitating remote access to and management of home automation devices. More particularly, the home or business appliance of the present invention operates in conjunction with a novel network operations framework and network service center that supports the managed services and all of the manageable capabilities of the home/business. For instance, the appliance and supporting network service center architecture provides for distributing configuration and data information to residential home gateways; provides updates to residential home gateways; enables inbound services to in-home gateways; provides remote web access to residential home gateways (include login via control channel); provides off-premise voice extensions for a residential home gateway; provides remote diagnostics and home network management; collects billing records; alarms and statistical information from residential home gateways; updates and manages endpoints in the digital home; and enables remote control of "smart devices" in the home.

For the in-home services, the multi-services gateway appliance connects the various service delivery elements together for enabling the user to experience a connected digital home, where information from one source (for example, voicemail) can be viewed and acted on at another point (for example, the TV). The multi-services gateway appliance hosts the various in-home device interfaces and facilitates the moving of information from one point to another. Some of the in-home endpoint device processing duties performed by the appliance 10 include, but are not limited to: 1) detecting new devices and provide IP addresses dynamically or statically; 2) functioning as a (Network Address Translator) NAT, Router, and Firewall; 3) providing a centralized disk storage in the home; 4) obtaining configuration files from the network and configures all in-home devices; 5) acting as a registrar for SIP-based devices; 6) receiving calls from and deliver calls to voice devices; provide voicemail services; 7) decrypting and securely streaming DRM'd media; 8) distributing media to an appropriate in-home device; 9) compressing and encrypting files for network back-up; 10) backing-up files to the network directly from appliance; 11) handling home automation schedules and changes in status; 12) providing in-home personal web-based portals for each user, 13) providing Parental Control Services (e.g., URL filtering, etc.); 14) creating and transmitting billing records of in-home devices including, recording, and uploading multi-service billing event records; 15) distributing a PC client to PC's in the home used in support of the various services such as monitoring events or diagnostic agents; 16) storing and presenting games that users and buddies can play; 17) delivering context-sensitive advertising to the end point device; 18) delivering notifications to the endpoint device; and 19) enabling remote access through the web, IM client, etc. Other duties the gateway appliance 10 may perform include: service maintenance features such as setting and reporting of alarms and statistics for aggregation; perform accessibility testing; notify a registration server (and Location server) of the ports it is "listening" on; use IM or like peer and presence communications protocol information for call processing and file sharing services; receive provisioning information via the registration server; use a SIP directory server to make/receive calls via the SBC network element to/from the PSTN and other gateway appliance devices; and download DRM and non-DRM based content and facilitating the DRM key exchanges with media endpoints.

According to the present invention, with reference to FIG. 1A, the present invention is a next-generation multi-services residential gateway appliance 10, also referred to herein as "the appliance", that can be used at the home or business ("premises") that is programmed to simplify various aspects of managing the emerging home/business digital networks including the myriad of interconnected digital endpoint devices. With processing, storage, and network connectivity to a novel network operations support infrastructure 50, the gateway appliance is capable of extending the service provider's network demarcation point into the subscriber's home offering powerful capabilities at the customer's residence. By leveraging powerful processing and intelligence residing on the gateway appliance at the customer's premise, the solution for the premises provided by the gateway appliance addresses requirements such as shared Internet connection, remote diagnostics and installation help, integrated VoIP support, connected entertainment offerings, and bundled services via a single platform. Besides providing a secure platform for building and providing multiple services for digital clients at the premises, the appliance, in combination with a novel network operations support infrastructure 50, additionally provides a communications and instant messaging-type framework including presence and networking capability for enabling file-sharing capabilities amongst a community of peers, friends, or family. As part of the presence and networking capability offered, connectivity is required between the appliance 10 and a network operations support infrastructure or service center (SC) 50 described in further detail herein below and that is particularly enabled to support the next-generation multi-service applications gateway appliance provided at the premises that assumes many of the functions that are typically network-based.

As shown in FIG. 1A, secure connectivity to the service center 50 is provided, in one embodiment, via a wide area networks (WAN) interface such as Ethernet WAN 53 over a broadband connection via the public Internet 99, or, for example, via a wireless EvDO (Evolution Data Optimized) Internet data interface embodied as a PCMCIA (personal computer memory) wireless card 56. As will be described in greater detail hereinbelow, the service center 50 generally provides a secure IP-based communications and processing infrastructure for supporting the variety of services and applications and communications residing at multiple gateway devices $10_1, \ldots 10n$. This support architecture is designed for high availability, redundancy, and cost-effective scaling.

The secure platform for building and providing multiple services for digital clients at the premises assumes connectivity between the appliance 10 and each of a user's digital devices (referred interchangeably herein as "digital endpoints" or "digital endpoint devices"). This connectivity may be provided by implementation of one or more USB ports (interfaces) 13, a wired Local Area Network connection such as provided by an Ethernet local area network (LAN) interface 16, or a wireless network interface via a WiFi LAN access point 62 provided, for example, in accordance with the I.E.E.E. 802.11 b/g/n wireless or wireless network communications standard. These physical interfaces provide IP network interconnectivity to the endpoint devices connected to a local IP network 60 at the premises.

That is, the gateway appliance interfaces with digital endpoint devices including, but not limited to: a home automation networking device 20 (e.g., X10, Z-Wave or ZigBee) for wired or wireless home network automation and control of networked home devices such as a switch controller 22, sensor devices 23, automatically controlled window blinds 24, a controlled lighting or lamp unit 25, etc.; individual or a wired or wireless network of personal computing (PC) and laptop/mobile devices 30a, . . . , 30c that serve as file sources, control points, and hosts for various other client endpoints; one or more television display devices 32 including associated set top boxes (STB) 35a or digital media adapter (DMA) 35b; and one or more VoIP phone devices (e.g., SIP phones) 40, or other devices (not shown) that convert IP interfaces to PSTN FXO and FXS interfaces. Although not shown in FIG. 1A, other digital endpoint devices for which connectivity may be established with the appliance 10 include, but are not limited to: personal music or media players, hi-fi audio equipment with media streaming capability, game stations, Internet radio devices, Wi-Fi phones, wifi or other wirelessly enabled digital cameras, facsimile machines, electronic picture frames, health monitors (sensor and monitoring devices), etc. As will be described in greater detail herein, the gateway appliance includes both a hardware and software infrastructure that enables a bridging of the WAN and LAN networks, e.g., a proxy function, such that control of any digital endpoint device at the premises from the same or remote location is possible via the gateway appliance 10 using a secure peer and presence type messaging infrastructure or other communications protocols, e.g., HTTPS.

For example, via any IM-capable device or client 80a, 80b respectively connected with an Instant Messaging (IM) or XMPP (Extensible Messaging and Presence Protocol) network messaging infrastructure, e.g., IM networks 99a, 99b such as provided by Yahoo, Microsoft (MSN), Skype, America Online, ICQ, and the like, shown for purposes of illustration in FIG. 1A, a user may access any type of functionality at a subordinate digital end point device at the premises via the appliance 10 and service center 50 by simple use of peer and presence messaging protocols. In one exemplary embodiment, a peer and presence communications protocol may be used such as Jabber and/or XMPP. Particularly, Jabber is a set of streaming XML protocols and technologies that enable any two entities on the Internet to exchange messages, presence, and other structured information in close to real time. The Internet Engineering Task Force (IETF) has formalized the core XML streaming protocols as an approved instant messaging and presence technology under the name of XMPP (Extensible Messaging and Presence Protocol), the XMPP specifications of which are incorporated by reference herein as IETF RFC 3920 and RFC 3921. Thus, the gateway appliance of the present invention is provided with functionality for enabling a user to remotely tap into and initiate functionality of a digital endpoint device or application at the premises via the IM-based messaging framework. In addition, the appliance 10 and network connectivity to the novel service center 50, in accordance with the invention, provides a secure peer and presence messaging framework, enabling real-time communications among peers via other gateway appliances $10_1, \ldots, 10n$. For instance, the appliance provides the ability to construct communication paths between peers with formal communications exchanges available between, for example, one appliance at a first premises and a second appliance located at the remote premises. Thus, such an infrastructure provides for content addressing, enabling peers through remote gateway appliances $10_1, \ldots, 10n$ to supply and request content such as files, media content or other resources of interest to a community of interest.

Besides handling all aspects of the digital home communications, e.g., IP, voice, VoIP, phone connectivity, the gateway appliance 10, when operable with the service center 50, provides a service-oriented architecture that manages services for the digital home and facilitates the easy addition of new services or modification of existing services. Such services may include, for example, facility management (home automation), media content downloading and Digital Rights Management (DRM), device updates, data backups, file sharing, media downloading and transmission, etc., without the intermediary of a plurality of external service providers who may typically provide these individual services for every digital endpoint device in the home or premises. That is, the appliance is integrated with hardware and software modules and respective interfaces that handle all aspects of home automation and digital endpoint service and management for the home in a manner without having to rely on external service providers and in a manner that is essentially seamless to the user. This, advantageously is provided by the service center 50 which is enabled to access regions of the gateway device 10 that are not accessible to the user, e.g., for controlling the transport and storing of digital content and downloading and enabling service applications and upgrades and providing largely invisible support for many tasks performed by users. Thus, central to the invention, as will be described in greater detail herein below, is the provision of service logic located and stored at the appliance 10 providing soft-switch functionality for providing call-processing features at the premises (rather than the network) for voice communications and enabling management of other service features to be described. With the provision of central office type call services and other service features provided at the appliances $10_1, \ldots, 10n$, a distributed soft-switch architecture is built. While transactions occur with cooperation of the service center 50 to provide, for example, service subscription/registration, authentication/verification, key management, and billing aspects of service provision, etc., and with all of the service logic and intelligence residing at the appliance, a service provider can offer customers a broad spectrum of services including, but not limited to: media services, voice services, e.g., VoIP, automated file backup services, file sharing, digital photo management and sharing, gaming, parental controls, home networking, and other features and functions within the home or premises (e.g., home monitoring and control). Users can access their content and many of the solution's features remotely. Moreover, software updates for the in-home devices that require updating are handled in an automated fashion by the system infrastructure. The service center infrastructure additionally provides a web interface for third ($3^{rd}$) party service providers to round out the service solutions provided at the appliance for the premises.

Gateway Appliance Software and Hardware Architecture

Figure 2B:
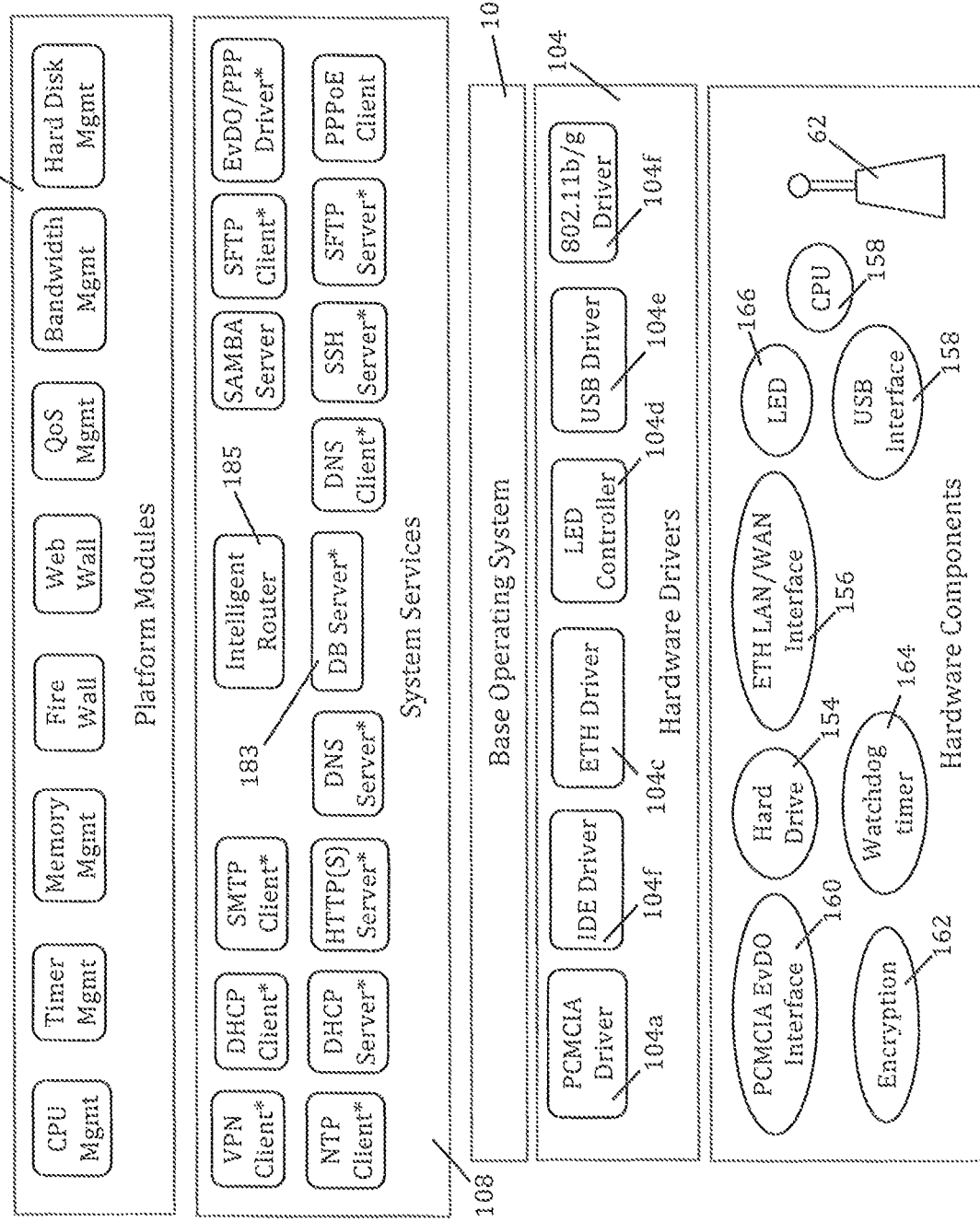

The composition of the premises gateway appliance 10 according to the present invention is now described in greater detail with reference to FIGS. 2A-2C. As shown in FIG. 2A, the gateway appliance 10 comprises a layered architecture 100 enabling the encapsulation of similar functionality; minimization of dependencies between functions in different layers; and facilitates reuse or sharing of logic across the layers to provide a managed service framework 120. The service management functionality provided by the framework enables deployment of new services as pluggable modules comprising computer readable instructions, data structures, program modules, objects, and other configuration data in a plug and play fashion. The layered service architecture 100 additionally provides the appliance with intra process communication and inter process communication amongst the many services and modules in the service framework layer that enables the provisioning, management, and execution of many applications and services 130 depicted, e.g., Services A, B, . . . , N at the gateway. Additionally, provided are the application service interfaces 140 that enables communication from user endpoint devices with service environments. FIG. 2A thus depicts a high level service framework upon which are built services, e.g., downloaded via the support network as packages that are developed and offered by a service entity for customers.

More particularly, as shown in FIG. 2B, a base support layer 102 comprises essential hardware components including a processor device 152, e.g., a system on chip central processing unit ("CPU") that includes processing elements, digital signal processor resources, and memory. The CPU 152 is also coupled to a random access memory ("RAM") and additionally, non-volatile hard drive/disk magnetic and/or optical disk memory storage 154. Generally, the above-identified computer readable media provide non-volatile storage of computer readable instructions, data structures, program modules, objects, and other data for use by the gateway device. As mentioned, the non-volatile hard drive/disk magnetic and/or optical disk memory storage 154 is preferably partitioned into a network side which is the repository for storing all of the service logic and data associated with executing services subscribed to by the user and is invisible to the user, and a user partition for storing user generated content and applications in which the user has visibility. Although not shown, the CPU 152 may be coupled to a microcontroller for controlling a display device. Additional hardware components include one or more Ethernet LAN/WAN interface cards 156 (e.g., 802.11, T1, T3, 56 kb, X.25, DSL or xDSL) which may include broadband connections (e.g., ISDN, Frame Relay, ATM, Gigabit Ethernet, Ethernet over SONET, etc.), wireless connections, or some combination of any or all of the above, one or more USB interfaces 158, and the PCMCIA EvDO interface card 160. A data encryption/decryption unit 162 is additionally provided as part of the architecture for providing data security features. A watchdog timer element or like timer reset element 164 is provided as is one or more LED devices 166 for indicating status and other usable information to users of the appliance. As further shown in FIG. 2B, the device drivers layer 104 comprises all of the device drivers for the various interfaces including a device driver for the USB interface, PCMCIA and Ethernet interface cards, a LED controller, and an integrated device electronics ("IDE") controller for the hard disk drive device provided. Additionally, as shown as part of the hardware and device driver components is the WiFi LAN access point 62 and corresponding 802.11 b/g/n wireless device driver.

As mentioned above, the gateway appliance provides an in-premises footprint enabling the service connectivity and local management to client(s). The implementation of functions and the related control such as a router (with quality of service (QoS)), firewall, VoIP gateway, voice services, and voice mail may be embodied and performed within the CPU 152.

Continuing, as shown in FIG. 2B, the device driver layer 104 comprises a multitude of driver interfaces including but not limited to: a PCMCIA driver 104a for enabling low level communication between the gateway and the PCMCIA network interface card wireless interface, an IDE driver 104b for enabling low level communication between the gateway and the local mass memory storage element, an Ethernet driver 104c for enabling low level communication between the gateway and the Ethernet network interface card, a LED driver/controller 104d, a USB driver 104e, and a wireless network driver 104f. The drivers provide the connectivity between the low level hardware devices and the operating system 106 which controls the execution of computer programs and provides scheduling, input-output control, file and data management, memory management, and communication control and related services for the appliance. With respect to the operating system, the appliance may comprise a computing device supporting any embedded operating system, any real-time operating system, any open source operating system, any proprietary operating system, or even any operating systems for mobile computing devices as long as the operational needs of the client discussed hereinbelow can be met. Exemplary operating systems that may be employed include Windows®, Macintosh, Linux or UNIX or even an embedded Linux operating system. For instance, the gateway appliance may be advantageously provided with an embedded operating system 106 that provides operating system functions such as multiple threads, first-in first-out or round robin scheduling, semaphores, mutexes, condition variables, message queues, etc.

Built upon the system operating system 106 is a system services support layer providing both client-like and server-like functions 108 that enable a wide range of functionality for the types of services capable of being managed by the gateway appliance. For instance, there is provided a Dynamic Host Configuration Protocol (DHCP) client and server software modules. The DHCP client particularly requests via a UDP/IP (User Datagram Protocol/Internet Protocol (e.g., Ipv4, Ipv6, etc.)) configured connection information such as the IP address that the gateway appliance has been dynamically assigned by a DHCP service (not shown), and/or any subnet mask information, the gateway appliance should be using. The DHCP server dynamically assigns or allocates network IP addresses to subordinate client endpoints on a leased, i.e., timed, basis; a Virtual Private Network (VPN) client which may communicate via a proxy server in the service control network according to a VPN protocol or some other tunneling or encapsulation protocol; a SMPT client for handling incoming/outgoing email over TCP in accordance with the Simple Mail Transfer protocol; a Network Time Protocol (NTP) (RFC 1305) for generating and correlating timestamps for network events and providing generally time synchronization and distribution for the Internet; a Domain Name Server (DNS) client and server combination which are used by the IP stack to resolve fully-qualified host or symbolic names, i.e., mapping host names to IP addresses; a HTTP(S) server handles for handling secure Hypertext Transfer Protocol (HTTP) (Secure Sockets Layer) communications for providing a set of rules for exchanges between a browser client and a server over TCP. It provides for the transfer of information such as hypertext and hypermedia and for the recognition of file types. HTTP provides stateless transactions between the client and server; a Secure File Transfer Protocol (SFTP) client and server combination which protocols govern the ability for file transfer over TCP; a SAMBA server which is an open source program providing Common Internet Files Services (CIFS) including, but not limited to, file and print services, authentication and authorization, name resolution, and service announcement (browsing); an EvDO/PPP driver including a Point-to-Point Protocol (PPP) daemon configuration; a PPPoE (Point-to-Point Protocol over Ethernet) client which combines the Point-to-Point Protocol (PPP), commonly used in dialup connections, with the Ethernet protocol, and which supports and provides authentication and management of multiple broadband subscribers in a local area network without any special support required from either the telephone company or an Internet service provider (ISP). This device is thus adapted for connecting multiple computer users on an Ethernet local area network to a remote site through the gateway and can be used to enable all users of an office or home share a common Digital Subscriber Line (DSL), cable modem, or wireless connection to the Internet; a Secure Shell or SSH server implemented with HTTP protocol that provides network protocol functionality adapted for establishing a secure channel between a local and a remote computer, and encrypt traffic between secure devices by using public-key cryptography to authenticate the remote computer and (optionally) to allow the remote computer to authenticate the user. Additionally, provided as part of the system services layer 108 is intelligent routing capability provided by an intelligent router device 185 that provides provides Quality of Service (QoS, guaranteed bandwidth) intelligent routing services, for example, by enforcing routing protocol rules and supporting unlimited multiple input sources and unlimited multiple destinations, particularly, for routing communications to networked digital endpoint devices subordinate to the gateway; and a central database server 183 for handling all of the database aspects of the system, particularly, for maintaining and updating registries and status of connected digital endpoint devices, maintaining and updating service configuration data, services specific data (e.g., indexes of backed-up files, other service specific indexes, metadata related to media services, etc.) and firmware configurations for the devices, and for storing billing and transaction detail records, performance diagnostics, and all other database storage needs as will be described in greater detail herein.

Referring back to FIGS. 2A and 2B, built on top of the system services layer 108 is the platform management layer 110 providing a software framework for operating system and communications level platform functionality such as CPU management; Timer management; memory management functions; a firewall; a web wall for providing seamless WWW access over visual displays via access technologies enumerated herein, e.g., HTTP, SMS (Short Messaging Service), and WAP (Wireless Access Protocol); QoS management features, Bandwidth management features, and hard disk drive management features.

Figure 2C:
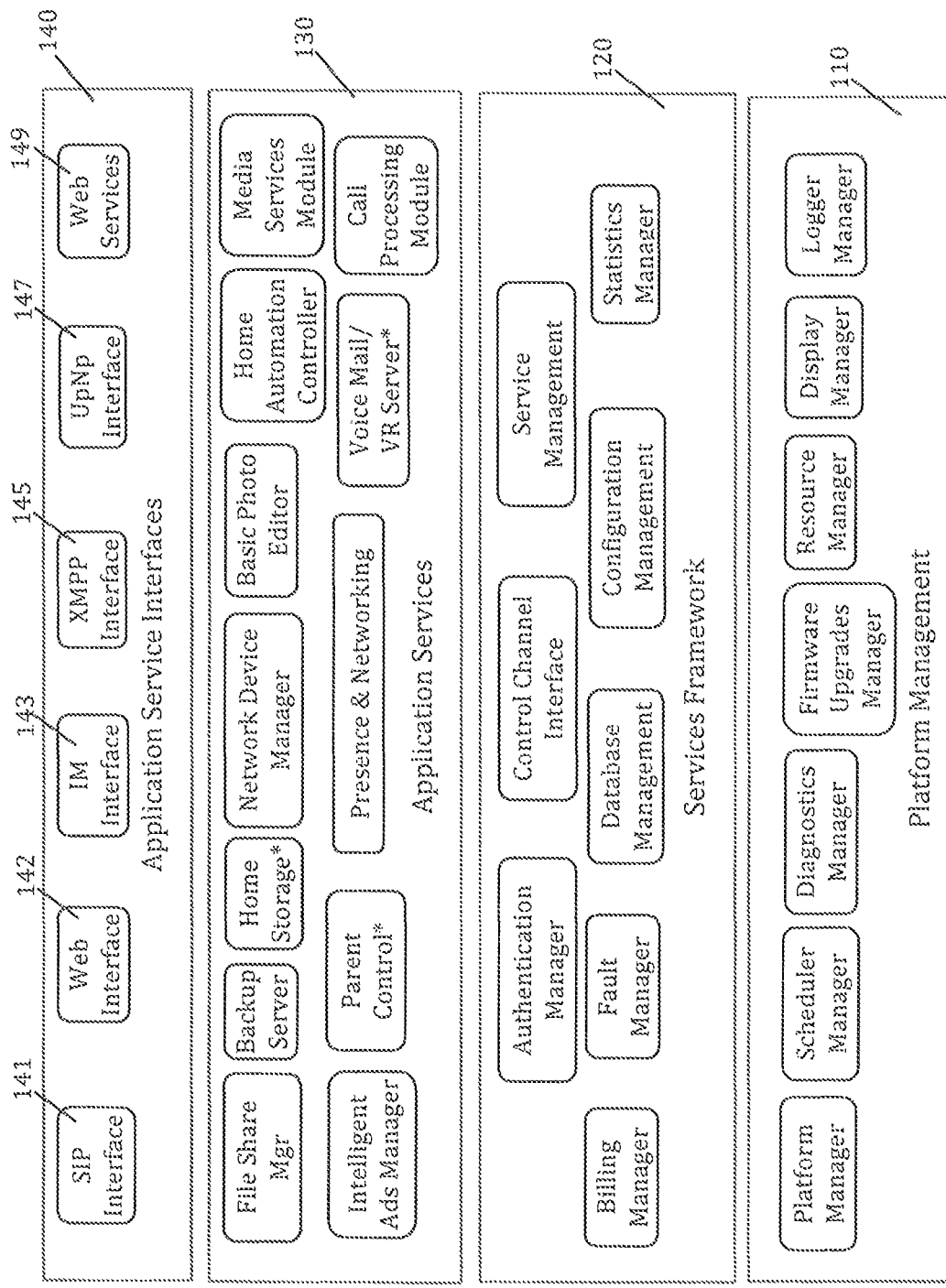

Further provided are platform management features 110 as shown in FIG. 2C that include a platform manager module which will implement unique rules based notification services on operational failure, i.e., when one of the components or services fails, the platform manager would detect this failure and take appropriate action such as implement a sequence of rules; a scheduler module for managing scheduled device maintenance, managing scheduled services, e.g., back-up services, etc.; a diagnostics module; a firmware upgrades management module for managing firmware upgrades; a resource management module for managing system resources and digital contention amongst the various resources, e.g., CPU/Bandwidth utilization, etc.; and a display management module and a logger management module for storing and tracking gateway log in activity of users and applications, e.g., voice call logs, at the premises. As will be explained in greater detail, the platform management layer in concert with resource and service management components enforces the separation of network side managed service control and user side delegations depending upon service subscriptions and configurations. For example, the platform and resource management encompass rules and guidelines provided according to subscribed services that act to enforce, manage and control input/output operations, and use of hard drives space, etc. A demarcation point is thus defined that provides a hard line between what is owned by the customer and what is owned by the service provider.

Referring back to FIGS. 2A and 2C, built on top of the platform management layer 110 is the Services Framework 120 providing a library of application support service processes that facilitate data collection and data distribution to and from the multimedia access devices including, but not limited to: authentication management for use in authenticating devices connected to the gateway; billing management for collecting and formatting service records and service usage by endpoint devices, e.g., calls, back-up services, etc.; fault management for detecting and managing determined system and/or service faults that are monitored and used for performance monitoring and diagnostics; database management; a control channel interface via which the gateway initiates secure communications with the operations support infrastructure; configuration management for tracking and maintaining device configuration; user management; service management for managing service configuration and firmware versions for subscribed services provided at the gateway appliance; and statistics management for collecting and formatting features associated with the gateway appliance. Statistics may relate to use of one or more services and associated time-stamped events that are tracked.

Referring back to FIGS. 2A and 2C, built on top of the Services Framework layer 120 is the Application Services Framework 130 providing library of user applications and services and application support threads including, but not limited to: file sharing functionality; backup services functionality; home storage functionality; network device management functionality; photo editing functionality; home automation functionality; media services functionality; call processing functionality; voice mail and interactive voice response functionality; presence and networking functionality; parental control functionality; and intelligent ads management functionality. The multi-services applications gateway 10 further provides application service interfaces 140 that are used to enable a variety of user applications and communications modalities. For instance, the SIP Interface 141 is an interface to the generic transactional model defined by the Session Initiation Protocol (SIP) that provides a standard for initiating, modifying or terminating interactive user sessions that involve one or more multimedia elements that can include voice, video, instant messaging, online games, etc., by providing access to dialog functionality from the transaction interface. For instance a SIP signaling interface enables connection to a SIP network that is served by a SIP directory server via a Session Border Controller element in the service center 50 (FIG. 1A). The Web Interface 142 enables HTTP interactions (requests and responses) between two applications. The IM Interface 144 is a client that enables the multi-services gateway appliance connection to one or more specific IM network(s). The XMPP interface 145 is provided to implement the protocol for streaming (XML) elements via the appliance in order to exchange messages and present information in close to real time, e.g., between two gateway devices. The core features of XMPP provide the building blocks for many types of near-real-time applications, which may be layered as an application service on top of the base TCP/IP transport protocol layers by sending application-specific data qualified by particular XML namespaces and more particularly, provide the basic functionality expected of an instant messaging (IM) and present an application that enable users to perform the following functions including, but not limited to: 1) Exchange messages with other users; 2) Exchange present information with other devices; 3) Manage subscriptions to and from other users; 4) Manage items in a contact list (in XMPP this is called a "roster"); and 5) Block communications to or from specific other users by assigning and enforcing privileges to communicate and send or share content amongst users (buddies) and other devices. As further shown in FIG. 2C, the UpNp (Universal Plug and Play) 147 interface enables connectivity to other stand-alone devices and PCs from many different vendors. The Web services interface 149 provides the access interface and manages authentication as multi-services gateway appliances access the service center 50 (FIG. 1A) via web services.

Gateway Device Boot Sequence and Initialization

Figure 2D:
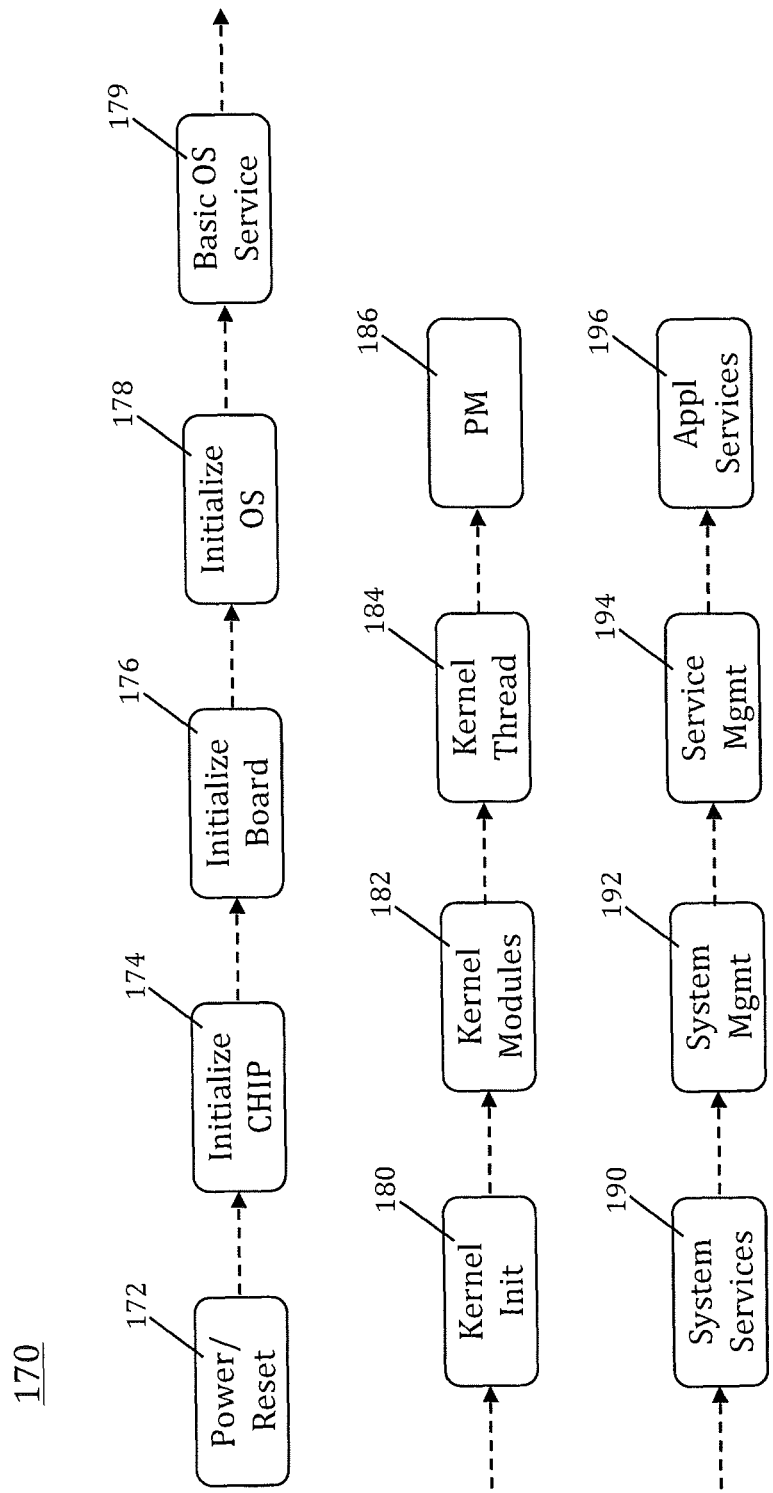
FIG. 2D depicts a boot sequence and initialization process for the multi-services applications gateway appliance 10 of FIG. 1A.

FIG. 2D depicts a boot sequence and initialization process 170 for the gateway appliance 10 of FIG. 1A. In response to turning on or resetting the appliance at step 172, the circuit board supporting the CPU chip element is initialized at step 174, and the board comprising the device drivers, serial console, Ethernet connection, WiFi connection, LED connection, USB connection, IDE hard drive connection, and the watchdog timer are all initialized at step 176. Then, the operating system (OS) layer is initialized including the base kernel, base OS modules, to provide basic services as indicated at step 178. Then, the basic OS services are initialized at step 179 including the Sshd, Ftpd, DNS, DHCP, and UpNp. Then, at step 180, customized kernel initialization is performed including the kernel modules such as Intelligent Routing, the QoS, the firewall, the web wall, encryption and watch dog timer control at step 182, and the kernel threads such as CPU management, memory management, hard disk drive management, and time management threads at step 184. Then, at step 186, the platform manager component of the appliance is initialized that starts system services and service managers for all services; the system services are then initialized at step 190, system management (e.g., Resource manager, Firmware Upgrade manager, Diagnostics manager and the Scheduler manager components, etc.) as shown at step 192, and service management (e.g., Service Manager, the network operations support center control channel client, the Billing manager, Stats manager, and Alarms manager components, etc.) as shown at step 194 that provide the services framework upon which the plurality of applications and services are built as shown in FIG. 2A. Finally, at step 196, the various subscribed to application services are initialized including, for example, but not limited to: the PBX server, Media server, file manager server, home automation server, presence and networking server, parental control services, and advertisement services, etc. The architecture such as shown in FIGS. 2A-2D provides a controlled managed services model for an IM messaging infrastructure.

Demarcation

Figure 3:
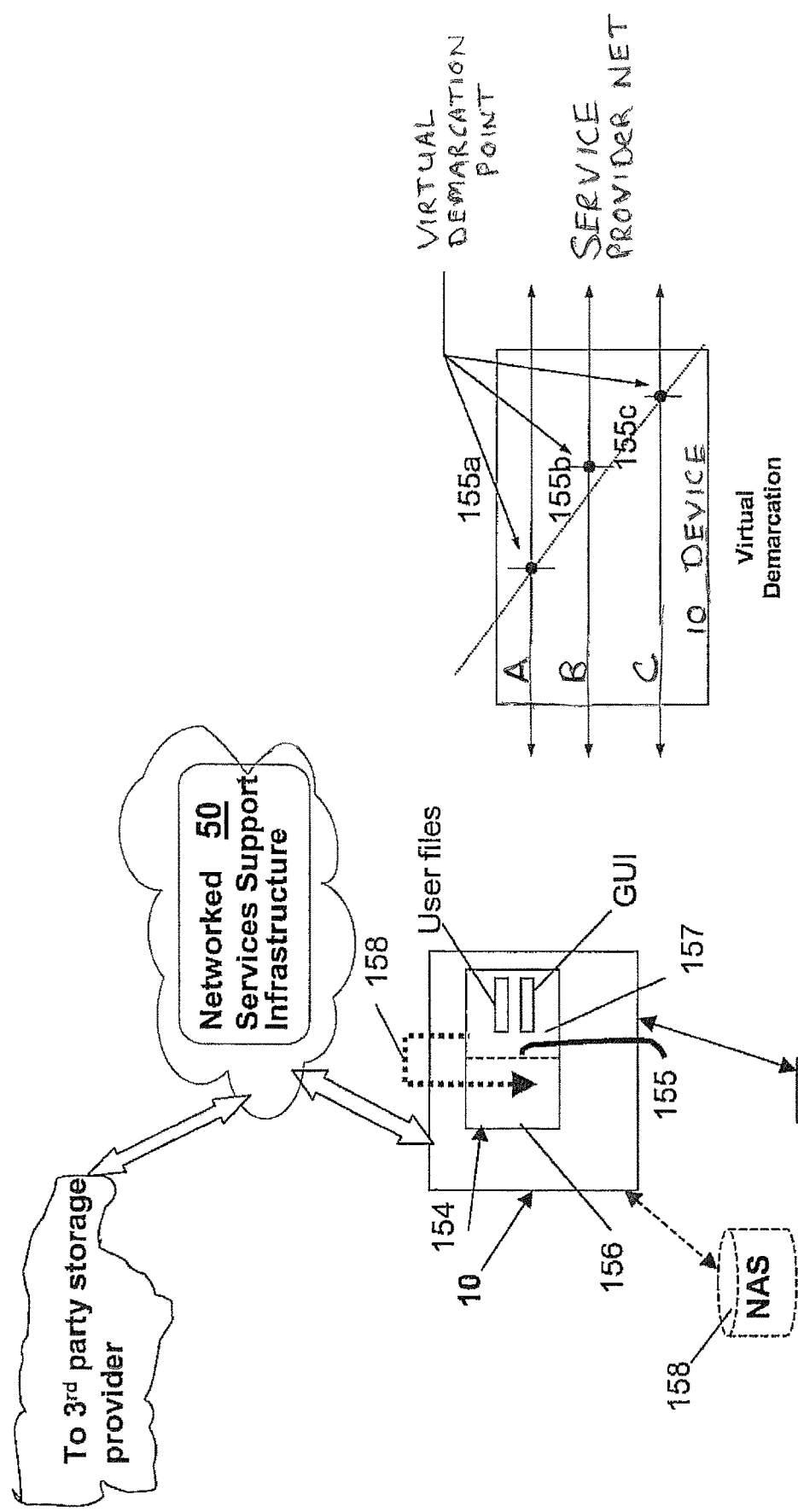
FIG. 3 conceptually depicts the physical demarcation point in a storage media that provides isolation of downloaded service logic and associated data for implementing services from service provider and/or downloaded content from a user generated content in accordance with the invention.

As shown in FIG. 3, in one aspect of the invention, the gateway appliance includes functionality for combining the storage available from its own internal and attached hard drive(s) 154 with any Network Attached Storage device 158 on the network to create a single virtual file system that consumers can use like a single drive. The gateway will automatically detect, mount, and manage the connections to the NAS devices and add them to its own file system. Users of the gateway are thus presented with a single consolidated storage device that they can access just like another drive on their PC. Users will not be exposed to the underlying protocols and management features required to provide such a feature. Users will no longer have to use each of the storage devices separately.

However, as further shown in FIG. 3, a virtual demarcation 155 is enforced at the centralized disc storage device 154 of the gateway appliance, e.g., which may comprise one or more physical hard drives, to physically and logically isolate the storage partition 156 where service logic and associated data for implementing services from service provider and/or downloaded media content are stored, and another partition 157 where user generated data, e.g., user files, is stored. The partition 156 belongs to the service center 50 that is limited to receiving logic and intelligence for the appliance and backed-up user files, all of which is managed by the service control network and enforced locally at the gateway; the other partition 157 is storage that is user accessible and includes a user accessible graphic user interface which may be accessed by a digital endpoint device, e.g., a PC, programmed to enable visibility if granted to the user. Thus, the user is enabled to skew the demarcation point depending upon the amount of control granted or authorized to the user according to subscribed features and service configurations. This separation within the gateway appliance 10 is an enabler for delivery of the service logic that resides on the appliance on the network side of the virtual demarcation. That is, the service provider offers all of its services upstream of this demarcation point and the customer can choose which service is selected that is within the control of the service provider's network.

While the service center 50 is responsible for placement of service modules and data beyond the demarcation point, the appliance 10 is equipped with certain functional elements such as encryption techniques, local directory obfuscation techniques, and local enforcement to prevent user visibility beyond the demarcation point that belongs to the service provider unless the user is enabled with such visibility. The intelligence and service logic that is on the appliance according to the invention is managed by the service center and provides the logic to limit user access.

FIG. 3 illustrates the virtual demarcation point within the gateway appliance located on the customer premise that occurs somewhere within the device allowing the customer and service provider to skew the physical location of the demarcation. The demarcation within this device can occur on a physical storage medium, e.g., hard disk drive 154 as shown in FIG. 2B, that has been sectored for different user, or in a virtual memory location, e.g., locations 155a, 155b or 155c, based on the service levels being offered, e.g., service A, service B or service C, respectively. This approach allows the customer more flexibility in manipulating the service rendered and services offered by the provider. By allowing the demarcation closer to the customer, this allows more control of features from the customer and allows the service provider closer control of the customer infrastructure without owning it all. Thus, with this device in place, the new demarcation moves based on the service.

For an example of demarcation control, if some data is required to be stored, e.g., a downloaded movie, the customer can store it locally, securely locally, or securely remotely. While it is the customer's responsibility to do storage locally and securely locally, with the new virtual demarcation, the service of providing locally secure data is now part of an offering of the service provider. While the data is still on site, the data is under control of the service provider and follows service agreements for that storage of data.

As another example of demarcation control, two movies may be downloaded and stored at the service center's partitioned side beyond the demarcation point as requested by a user via a user interface through a device connected to the appliance. This user interface, enabled via the user partition of the gateway appliance, is accessed through a PC, a TV, and cell phone. After authentication, the user could select and prioritize movies to purchase, for example, in compliance with the media content service provider. The choice of interfaces and amount of visibility by endpoint devices accessing this user interface has been optimally designed from a contention standpoint from perspective of controls, security, network service control manageability, and cost. In response, the selected movie(s) are downloaded to the service center's side 156 of the partition as shown in FIG. 3. Unless and until the user has purchased the movies for playback via an authentication process, that user will be prevented from accessing the content. Otherwise, the user may initiate streaming of the content directly to a digital endpoint device, e.g., a television, or will be granted permissions to download and play the movie according to the subscription with the media content provider as managed by the gateway device. If the user has purchased the movie, the movies may be transferred physically to the user storage portion of the partition. Otherwise, the content may be temporarily copied for local storage by the user at the user accessible portion of the demarcation point for playback at the user endpoint device.

Another example of demarcation control is the manipulation of features for a given service. Currently a subscription order is processed, and these features are manipulated within the service provider's network and sent down to the customer for provisional changes to equipment at the service center's side of the demarcation point. Via a GUI established for the endpoint device when connected with the gateway, when authenticated, files may be unlocked so the customer may locally manipulate services before and after demarcation point, thereby virtually shifting the demarcation point. Thus, a virtual demarcation point allows service providers flexibility in offering different services and features. Example services include, but are not limited to services such as: parental control, advertisement monitoring and replacement, home user habit monitoring, home channel monitoring, and back-up services.

Gateway Processing

For the in-home services, the multi-services gateway appliance connects the various service delivery elements together for enabling the user to experience a connected digital home, where information from one source (for example, voicemail) can be viewed and acted on at another point (for example, the TV). The multi-services gateway appliance 10 thus hosts the various in-home device interfaces and facilitates the moving of information from one point to another. Some of the in-home endpoint device processing duties performed by the appliance 10 include, but are not limited to: 1) detecting new devices and provide IP addresses dynamically or statically; 2) functioning as a (Network Address Translator) NAT, Router, and Firewall; 3) providing a centralized disk storage in the home; 4) obtaining configuration files from the network and configures all in-home devices; 5) acting as a Registrar for STP-based devices; 6) receiving calls from and deliver calls to voice devices; provide voicemail services; 7) decrypting and securely streaming DRM'd media; 8) distributing media to an appropriate in-home device; 9) compressing and encrypting files for network back-up; 10) backing-up files to the network directly from appliance; 11) handling home automation schedules and changes in status; 12) providing in-home personal web-based portals for each user; 13) providing Parental Control Services (e.g., URL filtering, etc.); 14) creating and transmitting billing records of in-home devices including recording and uploading multi-service billing event records; 15) distributing a PC client to PC's in the home used in support of the various services such as monitoring events or diagnostic agents; 16) storing and presenting games that users and buddies can play; 17) delivering context-sensitive advertising to the end point device; 18) deliver notifications to the endpoint device; and 19) enabling remote access through the web, IM client, etc. Other duties the gateway appliance 10 may perform include: service maintenance features such as setting and reporting of alarms and statistics for aggregation; perform accessibility testing; notifying a registration server (and location server) of the ports it is "listening" on; using IM or like peer and presence communications protocol information for call processing and file sharing services; receiving provisioning information via the registration server; using a SIP directory server to make/receive calls via the SBC network element to/from the PSTN and other gateway appliance devices; and downloading DRM and non-DRM based content and facilitating the DRM key exchanges with media endpoints.

Gateway Appliance Interfaces

As mentioned, in one embodiment, the gateway appliance behaves as a DHCP (Dynamic Host Configuration Protocol) server managing and automating the assignment of Internet Protocol (IP) addresses in a premise (home) network and may be installed in the premise (home) network behind the access modem such as DSL (digital subscriber line)/cable/DOCSIS (Data Over Cable Service Interface Specification). FIGS. 1B(1) and 1B(2) illustrate the gateway appliance connection to the in-premise devices in different embodiments. In FIG. 1B(1), a gateway appliance 124 connects to a broadband modem 122 for access to the WAN and acts as a replacement to a router in a network, connecting to various endpoint devices 132. In another embodiment, FIG. 1B(2) shows a gateway appliance 129 acting as a LAN connection on an existing router 128. The existing router 128 functions as a bridge and the gateway appliance 129 behaves as the router connecting to various endpoint devices 134. In this embodiment, the WAN connection from and to the appliance 129 is via the exiting router 128 acting as a bridge.

In support of the gateway primary processing for handling all aspects of the digital home as described herein with respect to FIGS. 1A-1B(2), the Gateway Appliance provides the interfaces to the following in-home devices: 1) an interface to the Digital Media Adapter (DMA) 35b for television (TV) enabling bidirectional wireline or wireless communication. This interface supports several functions for multiple services including, but not limited to: media (video and music) by enabling the transfer of media (video and music) to the TV via a peer and presence messaging protocol; voice services by providing for Called Line ID and for voice mail control; and provide Home Automation Services including obtaining status and control of networked home automation devices; 2) a bidirectional wireline or wireless interface to a PC device for supporting the transfer of media (video and music) to the computer for storage and viewing; for supporting voice services, e.g., by providing for calls from SIP soft clients; for file sharing via a peer and presence messaging protocol notification, file back-up, and home storage functions, this interface will provide for the bidirectional moving of files; and for Home Automation Services, it will provide status and control of networked home automation devices; 3) a unidirectional wireline or wireless Media Streamer interface for enabling the sending of audio content to a Media Streamer, which in turn will provide the audio to a receiver/amplifier of a Home Sound System (stereo or digital multi-channel); 4) a unidirectional wireline or wireless Internet Radio Interface that provides for sending of audio content to an Internet Radio; 5) a unidirectional wireline or wireless interface to a Portable Media Player (PMP) that provides for sending audio content to a PMP; 6) a bidirectional Phone Adapter/PSTN Gateway (PAPG) Interface that provides for configuring and registering of the PAPG with the gateway appliance via exemplary Session Initiation Protocol (SIP), FTP, HTTP over Ethernet protocols, and provides for sending and receiving of calls to/from the PAPG; 7) a SIP Phone Interface that is similar to the PAPG interface; and a bidirectional wireless or wireline Home Automation Controller Interface that provides for updating the controller of existing devices, changing device states (for example, "light on") and relaying device status from the endpoint device to the gateway appliance via the controller. The PAPG is a SIP to PSTN adapter having an Ethernet port on one side and a FXS (foreign exchange station) and a FXO (foreign exchange office) port on the other. A user can thus plug a phone into the FXS and can plug a telephone line from the central office into the other.

With respect to the media adapter element 35b shown in FIG. 1A, this device converts audio and video (optionally) to a format suitable for a TV (HMDI/DVI/HDCP/Component/RCA). In addition, the media adapter 35b is capable of receiving context-sensitive commands from a remote control device (not shown). This enables the use of menus on the TV for controlling services for various functions. The media adapter element 35b may be physically combined with the gateway 10 and/or the media adapter element 35b may be physically combined with set top box functions 35a. Thus, the media adapter/TV combination is enabled to provide the following features including, but not limited to: display of media; media control functions, when enabled (FF, REW, STOP, PAUSE, etc.); display of CLID (Caller ID); control of voicemail; picture viewing; control of home automation; and some user functions for the gateway appliance.

With respect to the Set Top Box 35a as shown in FIG. 1A, this device handles rendering of media content suitable for television, digital decryption, and other DRM functions, Video on Demand purchases, etc. The Set Top Box/TV combination thus enables: media format conversion (for example NTSC to ATSC); decryption; other DRM functions (such as expiry of leases), prohibition of copying to digital outputs, function restriction, etc.; Video on Demand purchases; and media control functions (e.g., FF, REW, STOP, PAUSE, etc.). With respect to PCs interfacing with the gateway appliance, these devices serve as file sources, control points and hosts for various clients. That is, computers will provide: source/target for files to be shared, backed-up or transferred to home storage; access a personal web page with notifications, RSS, shared photos, voicemail, etc.; browser control for home administrator and user, and a host for IM and SIP softphone clients and other client devices. Further, with respect to PAPG (incl. Integrated Access Devices) and SIP phones, the PAPGs and SIP phones serve as SIP endpoints. Additionally, the IADs connect to FXS phones or faxes and the PAPGs contain IAD functions and also connect to the local PSTN via a FXO port. Thus, the following functions are provided: SIP user agent signaling; voice and video capabilities (SIP phones); FXS signaling (IAD and PAPG); FXO signaling to PSTN (PAPG) and, telephony feature support.

Logical Architecture and Support Network Infrastructure

While the gateway appliances as described above are each equipped with various logic and intelligence for service features that enable the gateway appliances to provide various integrated digital services to the premise, as described herein with respect to FIG. 1A, the network elements 50 referred to also as support center (SC) supports and manages multi-services gateway appliances, for instance, so as to control the accessibility to functionalities and service features provisioned in the gateway appliances and the ability to communicate with other gateway appliances and various digital endpoint devices connected thereto. Examples of various functionalities performed by the network support infrastructure include, but are not limited to: service initialization of the gateway appliances, providing security for the gateway appliances and the network support infrastructure, enabling real time secure access and control to and from the gateway appliances, distributing updates and new service options to the gateway appliances, providing service access to and from the gateway appliances and remote access to the gateway devices, but not limited to such. In support of these services, the service center provides the following additional services and features: authentication; multi-service registration; subscription control; service authorization; alarm management; remote diagnostic support; billing collection and management; web services access; remote access to gateway appliances (e.g., via SIP or Internet/web based communications); reachability to access challenged gateway appliances; software updates; service data distribution; location service for all services; SIP VoIP service; media services; backup services; sharing services; provisioning; gateway interfaces to other service providers (Northbound and peering); load balancing; privacy; security; and network protection.

Figure 4:
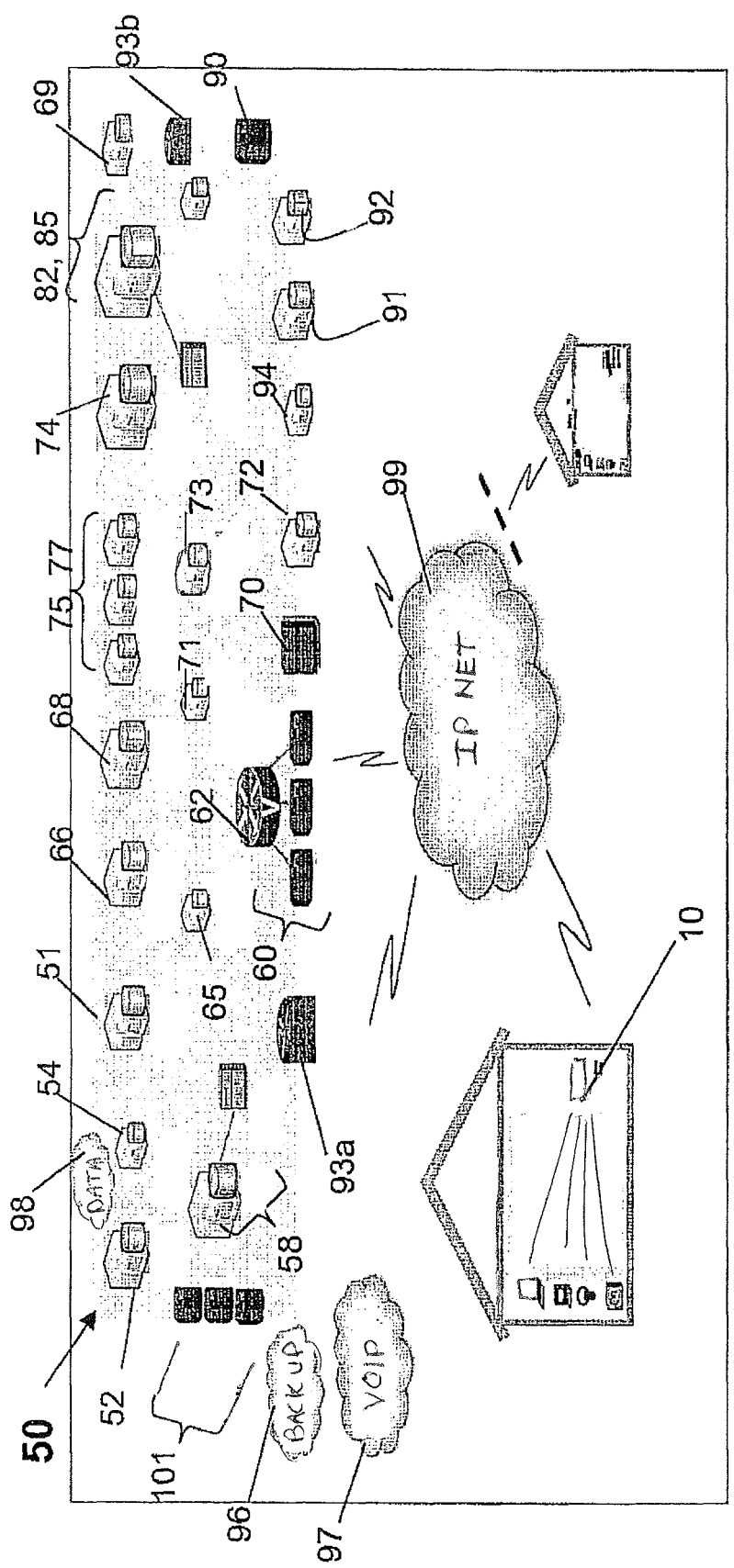
FIG. 4 depicts the networked operations services support infrastructure 50 for delivering service capabilities to the multi-services applications gateway appliance 10 of FIG. 1A.

The logical network architecture for the support network infrastructure delivering these capabilities is illustrated in FIG. 4. It should be understood that the functional components described in view of FIG. 4 may be combined and need not be running on discrete platforms or servers. Rather one server or component may provide all the functionalities for providing managed network of gateway appliances. In addition, any one of the components shown in FIG. 4 may perform any one of the functionalities described herein. Thus, the description in the present disclosure associating certain functions with certain components are provided for ease of explanation only and the description is not meant to limit the functionalities as being performed by those components only. Thus, the network elements or components 50 shown in FIG. 4 illustrate logical architecture only and the present invention does not require the specific components shown to perform specific functionalities described. Moreover, the functional components may use distributed processing to achieve a high availability and redundancy capacity.

The one or more network elements 50 illustrated in FIG. 4 support the gateway appliances 10 that are services point of presence in premises such as the home and the endpoint devices connected thereto. Examples of functionalities provided in the support network 50 may include, but are not limited to the following. Upgrades to gateway appliance firmware and various endpoint devices may be managed in the support network 50, for example, by a firmware update manager server 51. VOD (video on demand) functionalities, for example, serviced by VOD servers 52, ingest wholesale multi-media content and provide DRM-based premium content to the multi-services gateway appliance and endpoint devices. The support network 50 also may enforce DRM policies, for example, by a conditional access server 54, by providing key-based access and initiating billing processes. The support network 50 may also provide functionalities such as collecting billing information and processing billing events, which for instance may be handled by billing aggregator sub-system 58. The support network 50, for example, using one or more connection manager servers 60 may establish and maintain a signaling control channel with each active multi-service gateway appliance. Message routing functionality of the support network 50, for example, one or more message router devices 62, may provide intelligent message routing service for the network and maintain gateway device presence and registration status in an internal SC session manager sub-system. Publish and subscribe functionality of the support network 50, for example, a publish/subscribe (pub/sub) server sub-system 65 may provide publish and subscribe messaging services for the multi-services gateway appliances and the network elements.

The support network 50 may provide SIP-based directory services for voice services, for example, by its SIP directory server 66. In addition, location service functionality, for example, provided by the location server 68 may include IP and port level services for all inbound services. DNS services functionality may be provided by a DNS server 69 for all inbound services. The support network 50 may also provide virtual private network functionalities, for example, handled by its VPN server/subsystem 70, and provide VPN connection services for certain inbound services on multi-services gateway appliances. VPN connection services may be provided on those multi-services gateway appliances that have accessibility challenges, for example, those that are behind external firewalls and NATS. The support network 50 may also include functionality for determining the nature of the accessibility configuration for the multi-services gateway appliances. For example, the accessibility test determines whether the appliances are behind a firewall, whether NATS is required, etc. In one embodiment, accessibility service may be performed by an accessibility server 72 that functions in cooperation with the multi-services gateway appliance to determine the nature of the accessibility. The support network 50 also functions to provide provisioning services to all SC network elements 50 and multi-services gateway appliances 10. Such functionality of the support network 50, for example, may be implemented by the provisioning server 74 in one embodiment. Authentication functionality of the support network 50, for example, provided by an authentication server 71 provides authentication services to all SC network elements and multi-services gateway appliances. Subscription functionality of the support network 50, for example, provided by a subscription manager 73 provides subscription services to all multi-services gateway appliances. The support network 50 may include functionality for providing managing services for each of the services provided in the gateway appliance. For example, service managers 75 store and serve to distribute service specific configuration data to the multi-services gateway appliances. Service access test functionality of the support network 50 performs tests to multi-services gateway appliances to verify the accessibility for each subscribed service. Such functionality may be provided by service access test managers 77. The support network 50, for example, in an alarm aggregator subsystem 82 may aggregate alarms received from the multi-services gateway appliances. The support network 50 also include functionalities to support, for instance, by an alarms, diagnostics and network management server 85, network management and network management services. The support network 50 enables web interface communication mechanism, for example, via a Web services interface server 90 to, for example, provide access interface and manage authentication as multi-services gateway appliances access the SC for various services.

Additional SC network functionalities shown in FIG. 4 may include providing HTTP redirection services for public web access to the multi-services gateway appliances, which functions, for example, may be provided via a public Web redirect server 91. Public SIP redirect/proxy functionality provides, for instance, via a public SIP redirect/proxy server 92, SIP redirection and proxy services to public remote SIP phones and devices. The support network 50 also may include functionalities to provide a SIP-based network border interface and billing services for off-net voice calls. Such functionality in one embodiment may be provided in a Session Border Controller device 93a. Another functionality of the support network 50 may be providing SBC services to SIP roaming SIP callers in certain situations, which functionality, for example, may be provided by a Roaming SBC device 93b. The support network 50 also functions to provide dynamic NAT services during certain SIP roaming scenarios. Such functionality may be implemented in the Roamer Dynamic NAT Server 94.

The support network 50 further may provide off-site backup services for the SC network to a Wholesale Back-up Provider 96. The support network 50 further interoperates with Wholesale VoIP Provider 97, which may provide VoIP call origination/termination services for off-net voice calls. For instance, as will be described in greater detail herein, the support network 50 may provide VoIP/PSTN gateway that enables a translation between protocols inherent to the Internet (e.g., voice over Internet protocol) and protocols inherent to the PSTN. Other entities that may be partnered with the support network as shown in FIG. 4 include the content providers 98 that provide media-based content (including, but not limited to music, video, and gaming) to the SC network 50, gateway interfaces 101 for billing, alarms/NWM, provisioning interfaces for partnered wholesale providers (e.g., peering interfaces), and service provider customers (e.g., North bound interfaces).

Gateway and Service Network Initialization

Figure 5A:
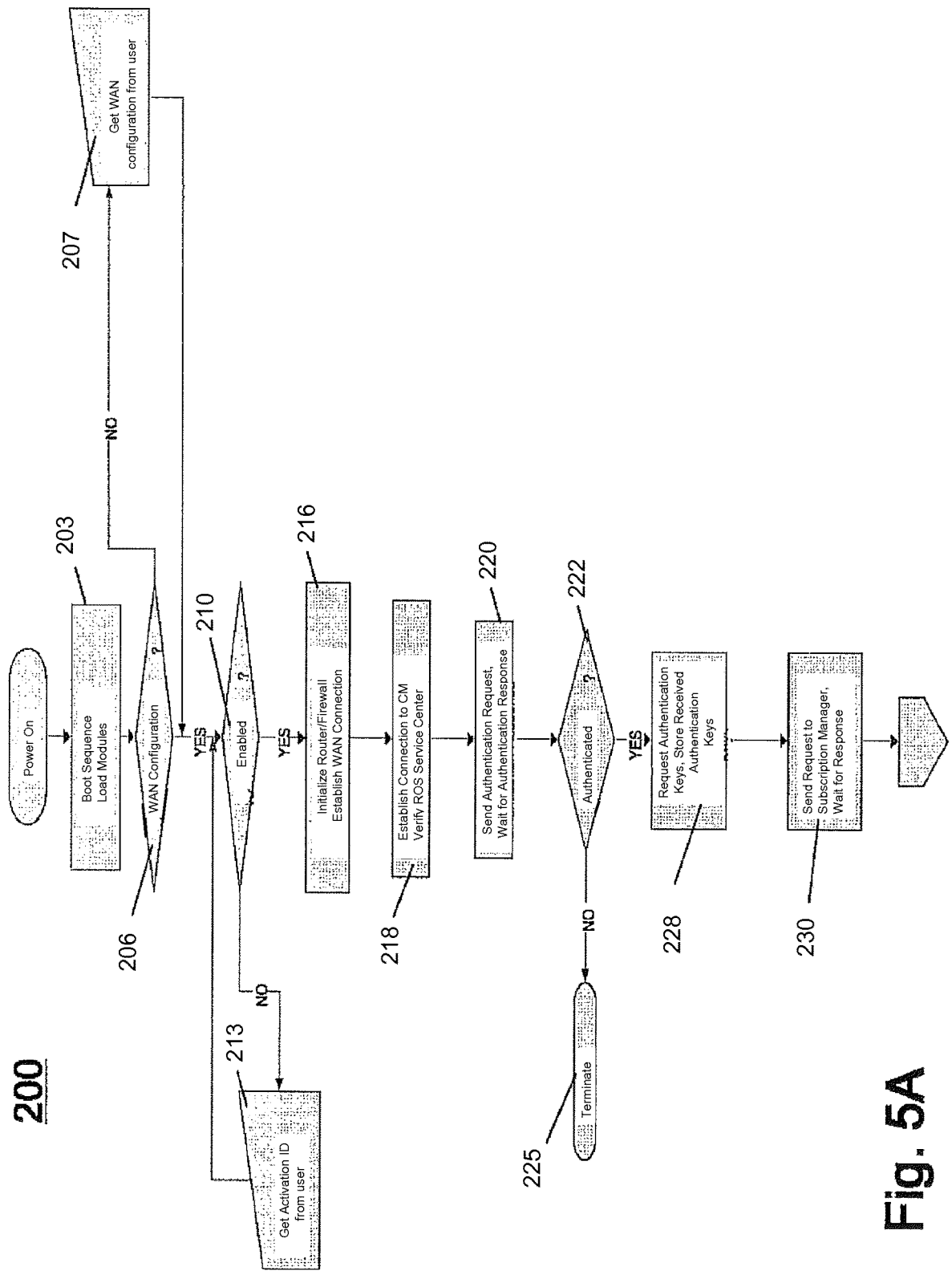
FIGS. 5A-5C describe aspects of an initialization technique 200 for establishing a gateway appliance's connection to and enabling communication with the networked operations services support infrastructure.
Figure 5B:
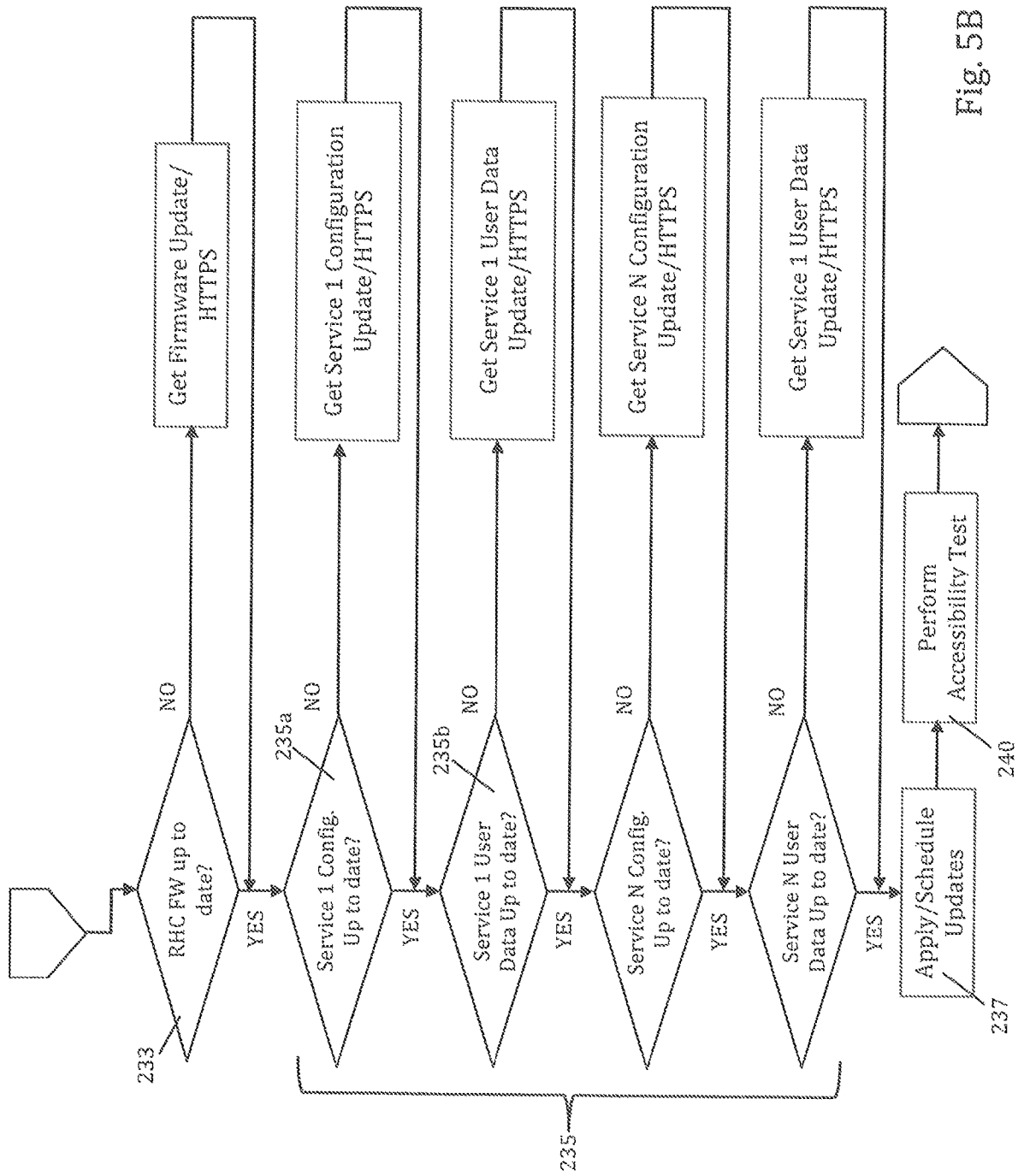
Figure 5C:
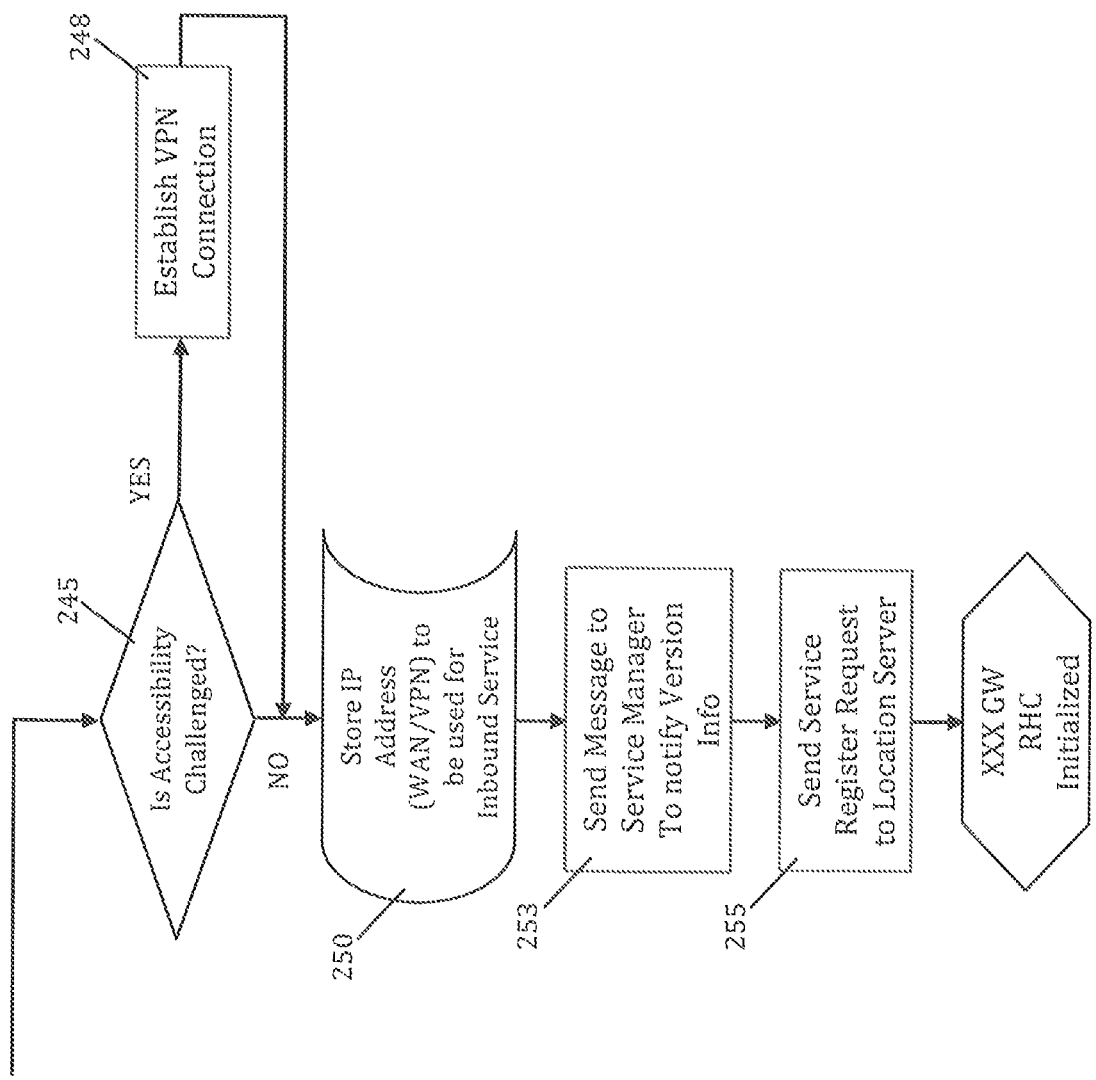

FIGS. 5A-5C describe high-level aspects of an initialization technique 200 for establishing a gateway appliance's connection to and enabling communication with the support network service center, and further the provisioning and management and maintenance of services. After power is applied to the appliance, a boot sequence is executed that loads the software modules of the gateway appliance at step 203.

As shown in FIG. 5A, a gateway appliance device is fully enabled if a subscriber activation code and optionally, the WAN configuration information is provisioned. Thus, optionally, at step 206, a determination is made as to whether the appliance's WAN configuration information is provided. If not, the process proceeds to step 207 where the system obtains from the user the gateway appliance's WAN configuration. At step 210, a determination is made as to whether the gateway appliance is fully enabled. If the gateway device is not fully enabled, the process is performed at step 213 to obtain an activation identifier (ID) from the user. It should be understood however, that before full activation, minimal functionality could be provided. Once the appliance is fully enabled, at step 216, there is initiated the process of initializing the router/firewall and establishing the WAN connection. In one embodiment, a Transport Layer Security (TLS) connection is established with the connection manager server functionality at the support network and communications with the support network at step 218. This TLS connection in one embodiment is a signal channel that is always-on for transacting various communications with the support network, for example, for the duration that the gateway appliance is powered on and providing its services and functionalities as the in-premise or in-home platform for endpoint devices associated with the premise. Continuing to step 220, the appliance then sends an authentication request including an authentication digest using a hardware identifier, an activation code, and a subscriber ID, and waits for an authentication response. At step 222, the process waits until the authentication notice or like response is received. If the authentication response is not received, the process terminates as shown at step 225. If the gateway appliance becomes authenticated, at step 228, the appliance requests from the SC the authentication keys and stores them at the appliance. These keys are used whenever an appliance has to be authenticated, e.g., when conducting a transaction or accessing the support center network, for example, through a web interface or a control signal channel.

Continuing to step 230 in FIG. 5A, the gateway appliance sends a request to the subscription manager functionality or the like of the support network, and the appliance waits until it receives a response. The request from the gateway appliance includes, for example, the appliance identifier information. In response, the subscription manager functionality of the support network replies with the latest firmware version and configuration information for that gateway appliance, for example, information associated with one or more services currently subscribed in that gateway appliance, the latest firmware information for the gateway and configuration for all subscribed services. There is also provided an indicator that identifies a change in user specific service data for all of the subscribed services, if any. Continuing to FIG. 5B, at step 233, the gateway appliance determines whether its firmware versions are up to date by checking the received version numbers with version numbers that currently exist in the appliance. If necessary, the gateway appliance receives the actual firmware/configuration data from the SC, for instance, through a web services interface over a secure HTTPS connection in one embodiment. At step 235, a determination is made as to whether the user firmware configuration data 235a and user data 235b for each service of up to N services that the user may be subscribed to are up to date. For each service, if it is determined that the firmware configuration data 235a and user data 235b are not updated, the gateway appliance may receive such data from the support network, for example, over the HTTPS connection. Continuing to step 237, the appliance may apply the configuration/firmware updates immediately or schedule them for another time. A user may utilize a GUI to schedule the updates. If certain firmware needs to be updated right away, there may be a prompt presented to the user to acknowledge and approve the updates. At step 240, a gateway appliance accessibility test is performed to determine if a VPN connection to the support network is needed. This may happen if the gateway appliance is behind a firewall or the like that protects the appliance from the public access. The test, for example, may be optional. In one embodiment, this test is done on start-up, and, for example, for cases when the appliance is disconnected from the WAN or a new IP address from the WAN is assigned. An accessibility testing functionality of the support network, for example, may send a connection request (such as stun or ping) in order to try to reach the gateway appliance. Different port numbers on a given IP address may be tested for reachabililty to the gateway appliance.

Continuing to step 245 in FIG. 5C, a determination is made as to whether accessibility has been challenged, e.g., the device lies behind a firewall at a private IP address. If accessibility has been challenged, then at step 248, a connection with a VPN is established. Step 250 represents the step of storing the WAN and VPN IP addresses to be used for inbound services. Examples of inbound services may include, but not limited to, voice service, remote web access, etc. At step 253, the gateway appliance sends a message to the support network, for example, which message is routed to service manager and subscription manager functionalities of the support network. The message informs the service manager and subscription manager functionalities, the gateway appliance's current version, and configuration information. Registering with those server functionalities may initiate notify handler service that enables asynchronous configuration, firmware, and/or user data updates. At step 255, a general multi-purpose registration is performed, whereby a service register request message is sent from the service manager to a location server functionality of the support network. This request message tells the location server functionality that the gateway appliance is ready to accept inbound services on a given IP address and port number. Thus, the information may include the IP address (WAN/VPN) and/or other specific data for informing the location server functionality how to find the gateway appliance. In one embodiment, a clock on a gateway appliance may be set when the appliance re-registers with the support network.

Architectural Overview for Establishing Connections and Authentication Process

Figure 6A:
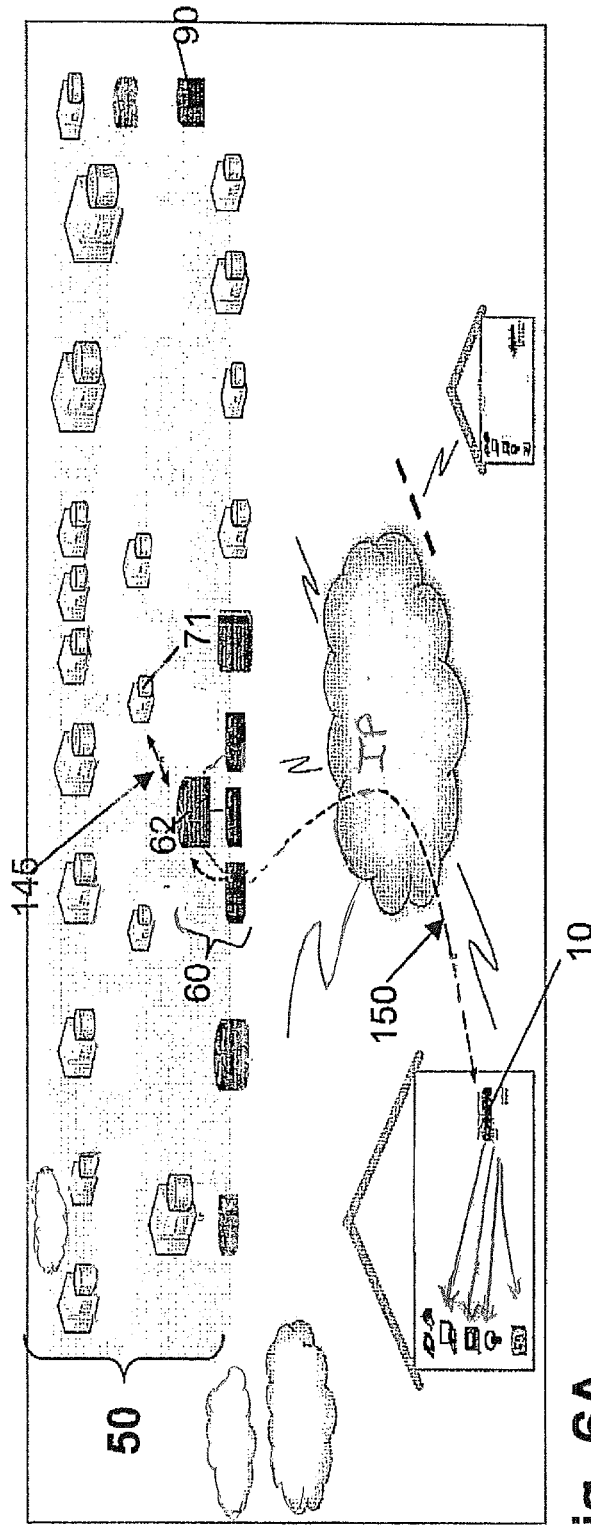
FIGS. 6A-6E describe more detailed interactions for functions and services to illustrate the core network elements of the networked operations service support center 50.

FIG. 6A is an architectural diagram illustrating a manner in which the multi-services gateway appliance makes an initial connection to the support network 50 in one embodiment of the invention. It is noted that the individual components shown in the support network 50 illustrate logical components or functionalities provided in the support network. As mentioned above, a signal channel in an exemplary embodiment is established between the gateway appliance and the support network during the appliance's initialization process, and in one embodiment this connection is maintained for the duration that the appliance is powered on and is providing its functionalities. Thus, a connection is established between the gateway appliance and the connection manager server functionality 60 or the like in the support network, for example, to provide connection services prior to establishing a session state and authenticating the gateway appliance. As shown in FIG. 6A, a TCP/TLS connection 150 is made between the gateway appliance using the appliance's broadband connection and the IP network to connection manager server functionality 60 of the services support network. The connection manager 60 or the like of the services support network 50 receives the session state of the network channel request where control is implemented to initiate authentication. A message router functionality routes the requesting message to an authentication server 71 or the like as shown in FIG. 6A. Prior to establishing any TCP/IP connection, an authentication is performed, as indicated at 145.

In one embodiment, the connection manager 60 may aggregate plurality of connection channels 150 and multiplex these signaling channels to a message router device 62. The connection managers 60 works with the message router 62 and the authentication server 71 to authenticate the multi-services gateway appliance and allow its access to the network by enabling the establishment of a control channel 150 providing an "always on" control channel between the multi-services gateway appliance and the services support center 50 once the gateway appliance is authenticated. The connection managers 60 or the like also provides network security and protection services, e.g., for preventing flooding, DOS attacks, etc. In one embodiment, there may be interfaces such as APIs for interfacing the connection managers 60 or the like to the message routers 62 and the multi-services gateway appliances 10. As the network of multi-services gateway appliances grow, the number of connection managers may grow to meet the demand for concurrent signaling control channel connections.

In one embodiment, message router device(s) 62 or the like provide control signal message routing services and session management services to the multi-services gateway appliance 10 and the other network elements of the support center 50. In one embodiment, the message router device 62 has control channel interfaces to the firmware upgrade manager server, VOD(s), billing system, content managers, pub/subs, service access test manager, authentication server, service manager, subscription manager, alarms aggregator, network manager and public web proxy redirect, and the multi-services gateway appliances. The message router 62 or the like may also include a session manager subsystem that maintains control channel state information about every multi-services gateway appliance client in the network. The message router 62 or the like, and session manager or the like enable sessions to be established to each multi-services gateway appliance 10 and each network element and provide robust routing services between all the components. The message routers 62 or the like may additionally connect to other message routers for geographic based scaling creating a single domain-based control channel routing infrastructure. The message routers 62 or the like may additionally connect to IM gateways and other message routers that provide user based IM services, which may enable users to interact directly with their multi-services gateway appliance via IM user clients. Thus, besides providing routing and session management for all the multi-services gateway appliances and the network elements, the message router element 62 or the like enables control signaling between all the network elements and the multi-services gateway appliances and connects to IM gateways to provide connectivity to other IM federations.

With respect to authentication functionality, an authentication component 71 provides authentication services for all the network elements of the SC. The SC network elements query the authentication server to verify the identity of elements, including the multi-services gateway appliance, during inter-element communications. The multi-services gateway appliances may indirectly utilize the authentication server to verify the identity of the network elements. The interacting network elements may return data that the multi-services gateway appliance uses to confirm the network element's identity.

The authentication server functionality 71 may interface to the multi-services gateway appliances and other network elements such as the message router or the like and session manger servers or the like, the accessibility server or the like, the service accessibility test mangers or the like, the web services interface or the like, the provisioning server or the like, the NWM or the like, pub/sub or the like, VOD's, CAs, and the billing system or the like.

Signaling Control Channel

As mentioned herein with respect to FIG. 6A, the connection manager servers 60 or the like functionality in the support network provide connection services and enable the establishment of a control channel, enabling an "always on" control channel between the gateway appliance and the service support center functions of the support network. Thus, in one embodiment, a gateway appliance establishes a TCP/TLS connection to the connection manager functionality in the support network as shown at 150.

Authentication

Once the gateway appliance is physically connected to the network, it registers and authenticates itself on the support network. In one embodiment, this registration and authentication is done through the above established secure connection. In one embodiment data link layer security may be established by implementing, for example, Simple Authentication and Security Layer (SASL). The SASL framework provides authentication and data security services in connection-oriented protocols via replaceable mechanisms (IETF RFC 2222). This framework particularly provides a structured interface between protocols and mechanisms and allows new protocols to reuse existing mechanisms and allows old protocols to make use of new mechanisms. The framework also provides a protocol for securing subsequent protocol exchanges within a data security layer. After establishing the TCP/TLS connection between the home appliance and the support network (e.g., connection manager server or the like) the SASL authentication process is initiated whereupon the gateway communicates authentication details to the connection manager server or the like. The connection manager server or the like of the support network routes the authentication request to the authentication server or the like via intermediary of the control message router device or the like and session manager servers or the like. Once at the authentication server or the like, the gateway appliance is authenticated, e.g., by processing the authentication details at the authentication server or the like. Additionally, control access information is communicated to a locations server or the like which may provide location information updates to, for example, other network functionalities or elements such as a file sharing server, remote web access server, and other elements. Once secure connection (e.g., XMPP connection) is established at step 326, authenticated session state between the home appliance and the support network is ensured and messages can safely flow to and from the gateway appliance. In one embodiment, authentication credentials may include: user ID, subscriber ID, and a unique identifier (id) that is hardware dependent. In an alternate embodiment, a unique hardware based id need not be sent, however, may be used to hash a string or digest. At this point, any requests originating from the gateway appliance may be serviced.

A chat based protocol or presence and peering based messaging protocol is used for the gateway device to establish connection with the support network. This may comprise a SASL or NON SASL-based XMPP (Extensible Messaging and Presence Protocol) described in IETF RFC 3920 and RFC 3921. For instance, using XMPP, messages are sent and received between the gateway appliance and the support network (e.g., via connection manager and message router functionalities).

During the authentication, if the support network does not contain the gateway appliance registration and subscription information, the support network may prompt the user via the gateway appliance for the information. Such information may include, but is not limited to, gateway identifier such as the MAC address, name for a fully qualified domain name (FQDN) which is a complete DNS name such as johndoe.xxx.com, subscriber information such as name, address, email, and phone number. Additionally, service plan information such as file sharing, voice, file backup, media services, personal page, home automation, billing, to which the user is subscribing or desires to subscribe, user name and password for the subscriber and billing options and information may be obtained.

In one embodiment, before completing the authentication process, the support network optionally may display to the user via the gateway appliance a list of the enabled services allowing the user to confirm the services enabled, and/or allow the user to add to or delete from the services enabled. Once the authentication process is completed, the support network registers the gateway appliance with other functionalities in the network for enabling different services. For example, for phone service there may be a registration process on the SIP redirect server functionality.

Authentication Keys, Service Keys, Dynamic Key Renewal

The gateway appliance and the support network utilize keys or tokens for authenticating the gateway appliance, web service interface requests, and other services subscriptions, for instance, to verify that the gateway appliances are valid users of the system and services. In one embodiment, the authentication keys (also referred to as tokens herein) are renewable and may change dynamically for each gateway appliance. For example, the authentication server or the like in the SC may generate updated keys or tokens for all or a selected number of gateway appliances, notify those appliances periodically or at predetermined times to retrieve the new authentication keys. In another embodiment, the gateway appliances themselves may request the authentication server or the like to provide a new or updated key. Yet in another embodiment, the updated keys may be pushed to gateway appliances. This way the keys or tokens are periodically refreshed. Such dynamically changing keys enhance security, for instance, making it difficult for hackers to track the changing keys.

Each appliance may have more than one authentication key, for instance, for different purposes. For example, there may be different keys or tokens for allowing access to different services or features provided by the appliance. Thus authentication keys are also referred interchangeably as service keys or tokens. These service keys may also dynamically change and are renewable. In one embodiment, the gateway appliance receives the service keys or tokens when individual services are provisioned on the gateway appliance. Thereafter, the service keys may be updated to change periodically, at a predetermined intervals, or regular intervals.

The keys or tokens themselves, in one embodiment, may be hardware based key. In another embodiment, they may be implemented independent of the hardware they are being used on.

Web Services Interface

The support network may also provide web services interface functionality (for example, shown in FIG. 4, 90) that forms an application programming interface (API) between the gateway appliances and the support network as a method to communicate between the gateway appliances and the support network. That is, in addition to the established signaling control channel, the gateway appliances and the support network may utilize web services interface to communicate. For instance, the gateway appliances and the support network may exchange information via secure HTTP or HTTPS using SOAP, XML, WSDL, etc., or the like.

When an authentication key is used or embedded in the message in order to validate the communication between one or more gateway appliances and the web services interface functionality in the support network. In one embodiment, the gateway appliance 10 may request from the support network, for instance, from its authentication server functionality, a temporary key, which is to be used when the gateway appliance 10 requests services via the web services interface 90. Preferably, this key is not a service specific key, but rather identifies a particular gateway appliance 10 to enter the network center through the web services interface 90. Every time the gateway appliance 10 requests a key, the authentication server functionality may store the key and the expiry time of the key. A response message provided from the authentication server has the key and expiry time. In one embodiment, gateway appliances are responsible to determine a status of the key compared to the expiry and to request a new key before the expiry time. In another embodiment, the web services interface authentication key may be assigned during initial registration and may be renewable as described above with reference to dynamic renewable authentication and service keys.

The web services interface subsequently directs message requests to the appropriate functionality in the support network. The incoming requests may be load balanced in one embodiment by the DNS server, and loading and performance information may be fed back to the DNS in support of this function. The web services interface may have interfaces (e.g., APIs) to the gateway appliance, the authentication server functionality of the support network, DNS, service managers functionality of the support network, NWM.

A gateway appliance may utilize the web services interface to pull data or information from the support network, while the support network may utilize the signaling control channel to push data such as various notification data to the gateway appliances.

Appliance Registration and Service Subscription

Figure 6B:
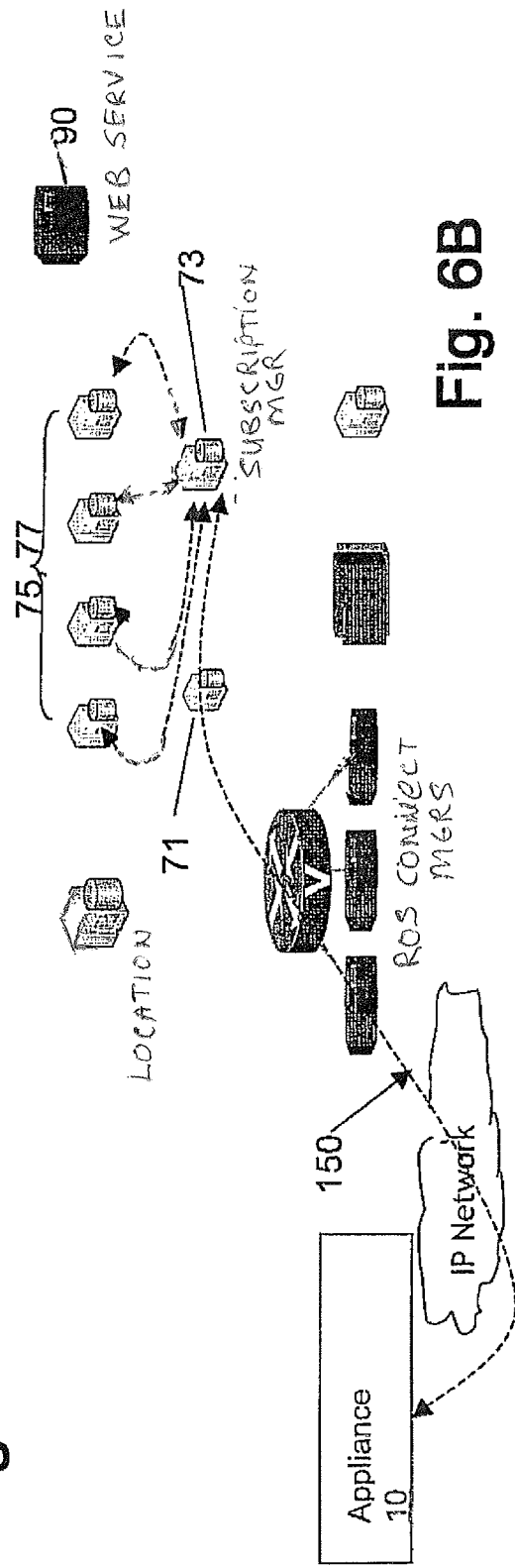
Figure 6C:
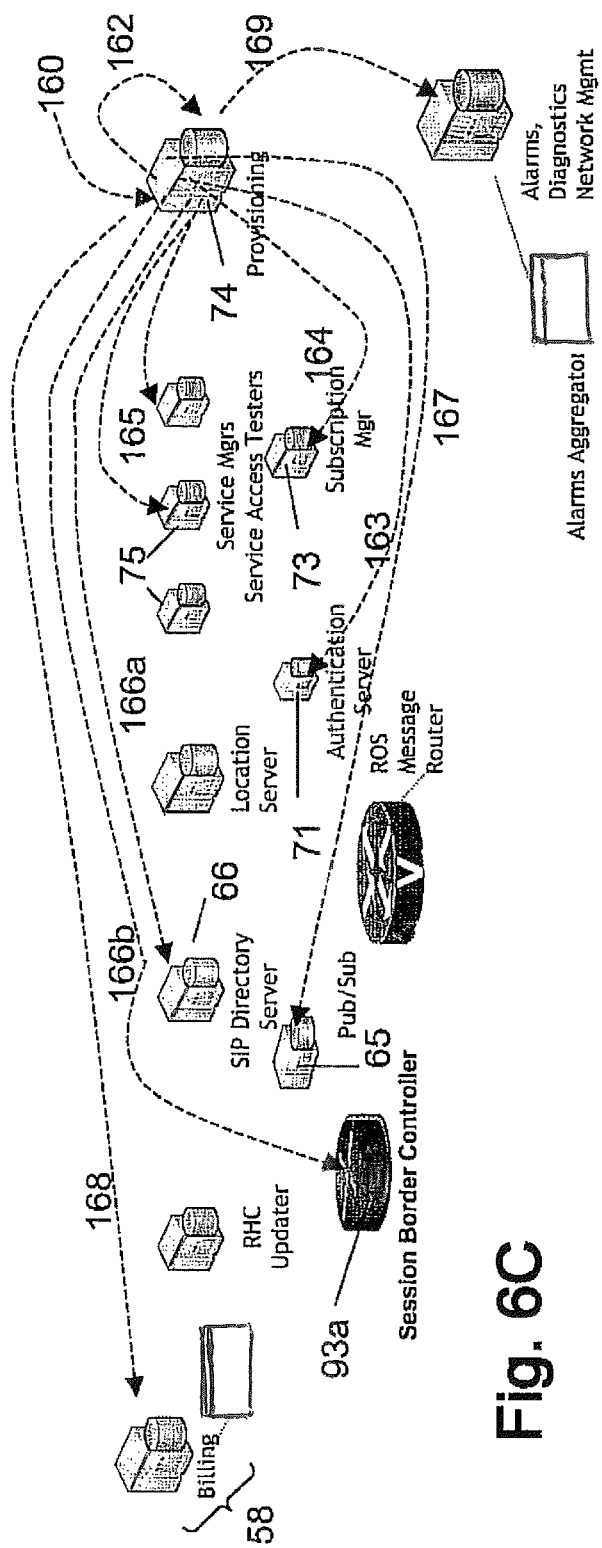

In one embodiment, the support network may further include provisioning manager functionality, which may handle gateway appliance registration and subscription activation. FIG. 6C depicts conceptually the process of subscriber provisioning in one embodiment provisioning manager functionality 74 may interface to $3^{rd}$ party order entry or provisioning system 160 that is enabled to accept purchase orders for gateway appliances and services provided therein. In another aspect, the provisioning manager may interface with a user interface provided in the support network for entering and accepting such orders. Thus, for example, gateway appliance registration or subscriber provisioning may occur through an internal customer service representative user interface application, or a customer/subscriber self-provisioning web application, or through a partner service provider application interface. Other registration methods are possible and they are not limited to those listed methods. For instance, the first time registration may occur during power-up and initialization stage as explained above, or any other way.

In each instance, the subscriber information may be input via the provisioning server 74 or the like functionality. As will be described in more detail, provisioning input may include attributes such as the gateway appliance identification information, user information, and service plan information. In one embodiment, the provisioning input data including subscriber provisioning action/data may be classified as accounting/business and operational data and may persist in the provisioning manager 74 as shown at 162. This may be an optional step, for example, where partner service providers have their own existing systems.

Examples of subscriber information include, but are not limited to the following. In addition, not all information is required as subscriber information. Examples are subscriber name, address, billing information, email, phone, social security number (SSN), etc.; gateway appliance ID, e.g., MAC address, FQDN such as e.g. johnsmith@ rosservice-.com. This data may be generated and may have different domain base depending on the provider. This ID may be called the JID (jabber ID) or BID (Box ID) or Family ID; a subscriber unique ID (Internal Generated Number); an assigned gateway appliance serial number (the serial number may be an external identifier of the gateway appliance); a gateway appliance model number (e.g., to link the software, configuration to the model); a user access password (this may be different from the gateway appliance access key which is operational system generated); a user service/ gateway appliance binding identifier (this may be generated by the system and mailed to user); a locale/region identifier; a list of the subscribed services, e.g., voice, video, remote access, backup; a list of service specific features, e.g., voice—call forwarding allowed, voice feature 2, etc.; a list of service specific user details, e.g., voice—DN, etc.; and Backup—Max GB, Max Bandwith, etc.

In a further step, as shown at 163 in FIG. 6C, the added gateway appliance and/or user, e.g., new subscriber is added to the authentication server functionality 71. Thus, for example, the authentication server functionality may maintain the following subscriber information/data for authenticating users and their gateway appliance devices 10: the JID/BID; the gateway appliance's serial number; a user access password; a user service/gateway appliance binding identifier; the subscriber active/disable status; the gateway appliance hardware ID; a subscriber/hardware binding: BOOL; a Web interface access key; and associated Web interface access key validity time.

In a further step, as shown at step 164, FIG. 6C, the added gateway appliance and/or user, e.g., new subscriber is added to the subscription manager (server or functionality or the like) 73. Thus, the subscription manager, for example, may maintain the following subscriber information/data for providing subscription information to gateway appliance devices 10: the model number, the JID/BID or the like to be able to create and distribute the right package of meta information and to identify the firmware ID, configuration and configuration data to the gateway appliance. Additional exemplary data made available at the subscription manager 73 may include, but not limited to: user ID; gateway appliance serial number; the gateway appliance model; the subscriber locale; current gateway appliance firmware version; and a list of services and enabled features, for example:
Service 1
Enable/Disable
Feature 1 Enable/Disable
. . .
Feature N Enable/Disable
Current Configuration Version
Service 2
Enable/Disable
Feature 1 Enable/Disable
. . .
Feature N Enable/Disable
Current Configuration Version
. . .
Service N
. . .

In a further step, as shown at step 165 in FIG. 6C, the added gateway appliance and/or user, e.g., new subscriber is added to one or more service manager (servers or devices or functionality or the like) 75. Service data maintained at the service manager 75 may include, but is not limited to: configuration files, e.g., voice: dial plans; parental control: black lists, etc. This data may be in a database or versioned files stored on disk. Optionally, the following subscriber data may be maintained at the service manager 75: the appliance's JID/BID; the provisioned subscriber data for each service (e.g., a list comprising Data 1, Data 2, etc.); and the generated subscriber data for each service (e.g., a list comprising Data 1, Data 2, etc.). It is understood that some services are basic services and some services may not have subscriber data at all. Thus, as an example, if implementing provisioning of Backup Services, the support network 50 may generate the following account on behalf of the subscriber: Backup Acct ID, KEY. The provisioned subscriber data and generated data are communicated to the gateway appliance.

In a further step, as shown at step 166a in FIG. 6C, the added gateway appliance and/or user, e.g., new subscriber, is added to a SIP directory server or like functionality 66 and additionally, to the Session Border Controller device 93a or like functionality, as shown at step 166b. For example, the SIP directory server 66 may be provisioned with data such as the SIP user identifier (e.g. www.gw10.ros.com); associated gateway DN numbers; and any other data as may be required by the SBC, e.g. realm data or location data for the endpoint device. Additional service data that may be provisioned may include: OFFNET/ONNET DN numbers; and other SIP Service specific data.

In a further step, as shown at step 167 in FIG. 6C, the added gateway appliance and/or user, e.g., new subscriber is added to the publication/subscription (Pub/Sub) server or like functionality 65. The new subscriber information maintained at the pub/sub may include the subscriber for gateway appliance firmware update events and for service configuration/locale events, e.g., U.S. dial plans, parental controls, etc. The pub/sub may maintain various event channels and the content for event channels (i.e., events per channel) and subscribed users for the event channels (i.e., users for channel).

In a further step, as shown at step 168 in FIG. 6C, the added gateway appliance and/or user, e.g., new subscriber is added to the billing sub-system server 58 or like functionality. The new subscriber information maintained at the billing sub-system server may include, but not limited to: the subscriber name; address; billing information; email; phone; SSN; user ID, e.g. johnsmith@rosservice.com; a subscriber unique ID (Internal Generated Number); an assigned gateway appliance serial number (the serial number may be an external identifier of the gateway appliance); a locale/region identifier; and a list of the subscribed services.

In a further step, as shown at step 169 in FIG. 6C, the added gateway appliance and/or user, e.g., new subscriber is added to the Alarms, Diagnostics, and Network Management server or like functionality and alarm aggregator sub-system. The new subscriber information maintained at the alarms, diagnostics, and network management server may include: alarms; user identifier and other data required for alarms management system; and diagnostics.

Thus, the provisioning functionality or the like 74 generally provides provisioning services to all SC network elements. The provisioning servers 74 may send and receive provisioning information via a gateway interface (e.g., APIs) to and from $3^{rd}$ party provides such as wholesale VoIP and backup service providers. The provisioning servers may also send and receive to the branding customer service provider (aka "North Bound" interfaces). The provisioning server may provide a graphical user interface for service provider users and customer users to order, initialize, and provision services. The provisioning server further may distribute the order or provisioning information to the following functional elements: subscription manager, authentication servers; service manager(s); SIP directory server; pub/sub servers; VOD(s); CA's; billing system; firmware update manager; location server; the NWM; SBC's; content provider(s); and wholesale providers via the gateway interfaces (APIs).

While the provisioning service or functionality was described with respect to registering new gateway appliances or subscribers, functionality for provisioning new services for existing users or gateway appliances may be provided in the similar manner, for example, by the provisioning server 74 or like functionality.

Automatic Discovery and Configuration of Endpoint Devices

A customer or user self-provisions endpoint device is on a particular multi-services gateway appliance. The provisioning system or like functionality 74 may provision how many endpoints and the types of devices that can be self-provisioned by the user. In one embodiment, the gateway appliances are capable of automatically discovering and configuring the appliance compatible devices belonging to enabled services in the premise such as the home or business, for instance, with minimal human intervention (e.g., for security purposes some devices may need administrator level prompting to proceed with configuration actions). For instance, the appliance compatible devices are devices that the appliance can communicate with and thus become the center of management for the services offered by these devices. One or more of these devices may have automatic configuration capabilities such as universal plug and play (e.g., uPNP devices). These devices also referred to as endpoint devices may include but are not limited to: media adaptors, SIP phones, home automation controllers, adaptors that convert IP interfaces to PSTN FXO, and FXS interfaces, etc. In one embodiment, the method of configuration, e.g., automatic discovery and configuration may be based on the specific device's current firmware or software or like version. The appliance in one embodiment also may keep a record or table of configuration information, for example, for those devices configured automatically. Such information may include, for example, for media adaptor, supported formats and bit rates, for home automation controller, information pertaining to the type of controller such as Insteon, Awave, etc.

As another example, if the phone service is enabled and if the appliance detects a new SIP/Saporo device, the appliance may prompt a user to determine if the detected device needs to be configured on the appliance. If it does, then the appliance may configure the detected device on its network (home network or other premise network). Yet as another example, when new drives are added to the appliance for storage expansion, the appliance may automate initialization of the new devices.

Subscription Management

The gateway appliance may request information from the support network for services that the gateway appliance is subscribing to, for example, during initialization stage as mentioned above or at any other time. The support network in one embodiment contains subscriber and gateway appliance identification details. Thus, the support network may respond to the request with the subscription information and version numbers for various configuration data needed for the services that are subscribed. FIG. 6B illustrates how a gateway appliance 10 establishes a service subscription request (service/request check), for instance, via the TCP/TLS/XMPP control channel 150 to the network support center 50. This service/request check may be available to ensure that the multi-services gateway appliance is in sync with the network provisioning system as to what type of services are allowed for the user. This allows finite and real time control of services allowed by the gateway appliance for a user. The service check may also be useful to keep track of the firmware/software of the gateway appliance, and to keep the same software base irrespective of the country/region, but have the ability to load configuration/customization information per user based on locale or other criteria.

As an example, during the multi-services gateway appliance initialization process, the multi-services gateway appliance queries the subscription manager, for example, via the control channel, to determine what services and features are enabled for the multi-services gateway appliance. The support network, for example, using its subscription manager functionality 73 responds with the subscription information associated with this particular gateway appliance. Examples of data that subscription manager functionality 73 may store in one embodiment may include but not limited to JID/BID, gateway appliance model number, services subscribed to, features subscribed to per service, and revision exception list for each gateway appliance. The multi-services gateway appliance 10 checks the received subscription information such as version information against the current versions on the multi-services gateway appliance 10. If the multi-services gateway appliance determines that the versions are different, it may start initiating download from the configuration data through web services interface 90. Preferably, the multi-services gateway appliance's firmware and service configuration are implicit subscriptions and hence the multi-services gateway appliance will receive notifications when new changes are available. The changes indicate the version to download and the same logic of version checking is performed in the multi-services gateway appliance. The multi-services gateway appliance 10 subsequently enables the subscribed services and features.

The subscription manager functionality 73 also informs all requesting SC network elements what services and features are enabled on a particular network element. The subscription manager functionality 73 also determines what service specific configuration data needs to be downloaded to the requesting multi-services gateway appliance. In an exemplary embodiment, the subscription manager functionality 73 determines the data needed by interacting with service manager functionality 75, which stores and distributes specific configuration data for services. The subscription manager functionality 73 may interface to the multi-services gateway appliances (e.g., indirectly) and the following functionalities of the support network: message routers and session manager(s), the accessibility server, the service access test mangers, the provisioning server, the NWM, VOD's, CAs, pub/sub, service manager server, and billing sub-system. The subscription manager functionality 73 may additionally support some internetworking to other service providers via the gateway interfaces.

In one embodiment, the support network includes service manager functionality for each specific service. The service manager functionality 75 may store and distribute service specific configuration data for each supported service on a per multi-services gateway appliance basis. Thus, service manager functionality 75 may include service specific configuration managers for voice, back-up, or any other service that are provided. Examples of this configuration data include, but not limited to, VoIP configuration data such as location-related dial plan information and content/media configuration data such as URL links, etc. The service manager functionality or servers 75 work with subscription manager functionality 73 to resolve multi-services gateway appliance version requests and ensure that the multi-services gateway appliances 10 have the correct version of configuration data. In one embodiment, there is a service manager for each supported service. In addition, there may be a service manager or like functionality for storing and distributing baseline multi-services gateway appliance configuration data. Subscriber data per service may exist inside the service manager and also, stored directly in the service component, e.g., SIP Redirect/SBC device. The service managers 75 or the like functionality or servers or devices may interact with the subscription manager 73, provisioning, NWM, web services interface 90, pub/sub, message routers, and multi-services gateway appliance. Additionally, 3rd party wholesale providers, such as a backup service, may interface to the service managers via a gateway interface or an API.

In an exemplary application for gateway appliance services, data is brought down to the gateway appliance to enable it to provide various services. Configuration data is provided to the gateway appliance from the support network. For instance, subscription manager functionality of the support network, for example, as part of initialization process, queries the service managers functionality to obtain configuration data that can be sent to the gateway appliance and which versions from configuration perspective to report back to the appliance. Such configuration data may include a web service interface URL of the service manager for where the gateway should communicate. The subscription manager functionality then sends the metadata of the configuration data, that is, information associated with the configuration data back to the gateway appliance. The gateway appliance then may update its configuration if needed by accessing the service manager functionality, for example, via the web services interface, and retrieving the needed data. In another embodiment, the support network (e.g., service manager functionality) may push the needed data to the gateway appliance via the signaling control channel. For each service, the support network provides configuration data to the appliance (e.g., via service manager functionality) and posts a notification if new configuration data is required. When the user invokes the service, the gateway appliance will thus know all that it needs to invoke the service. For instance, data that the gateway appliance needs may be obtained from the service manager functionality. Login information and keys may be obtained from authentication server for a particular service, e.g., for service keys.

Pub/Sub and Updates

As previously mentioned in view of FIG. 4, the publisher/subscribe (pub/sub) server or like functionality 65 accepts and maintains subscription requests for appliance upgrades and device upgrades from networked services support elements, and particularly, from every gateway appliance 10 in the system. Networked elements communicate with the pub/sub system or like functionality and publish information that other elements may have subscribed to. The pub/sub matching engine matches the published information with users (typically gateway appliances) that have subscribed for notices of new specific information. If the pub/sub matches a "pub" with a "sub", a notification message is sent, for example, via XMPP protocol or like peer and presence messaging protocol on the signaling control channel, to the subscribing user, notifying them of the new information.

Figure 6D:
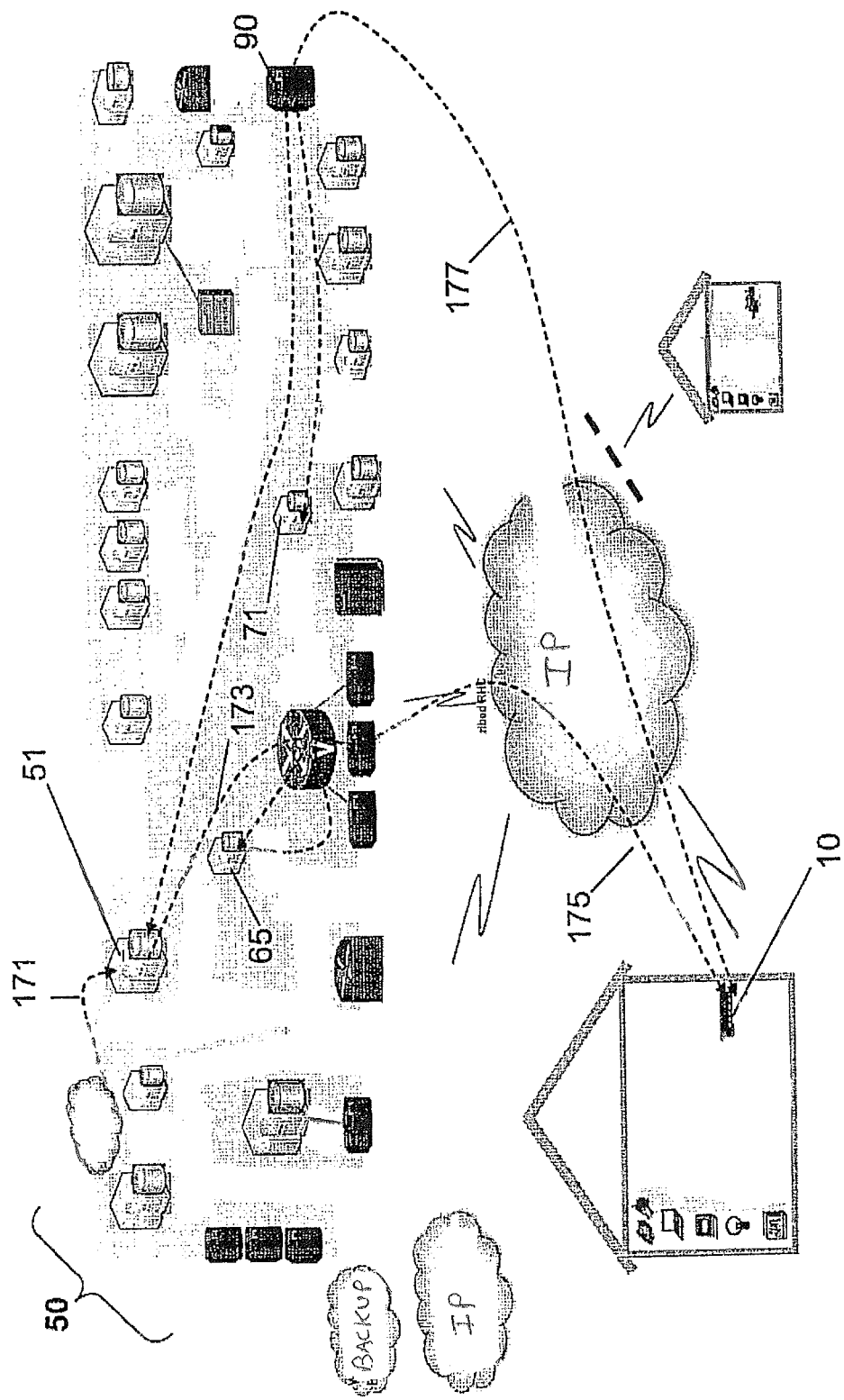

FIG. 6D highlights how the gateway appliance and the service center network elements utilize the signaling control channel and the publisher/subscriber (pub/sub) function to subscribe for notification of certain events and publish notification of these events in one embodiment. In this high-level example, the gateway appliance subscribes for firmware or software updates for the gateway appliance or endpoint devices that it connects, and is subsequently notified when such an event occurs. It is understood that the pub/sub system provides subscription and publication matching and notification services for both the gateway appliances and the networked service center elements or functionalities. Thus, the logical pub/sub device may have interfaces to all elements that use this mechanism to communicate with each other including, for example, firmware update manager, RMR, provisioning server, authentication server, service manager, subscription manager functionalities, and the gateway appliances.

In an example scenario depicted in FIG. 6D, the updater component or functionality with knowledge of updates to gateway firmware or software or the like, endpoint device firmware or software or the like, or service configuration files or the like, may publish the update information to the pub/sub server or like functionality 65, for example, as shown by the route 173. The updater component 51 may receive a message or notification at 171 that updates are available from other sources. Additionally, various service managers (or like functionality) 75 that handle specific services and associated configuration information and data may publish information in the pub/sub that updates are available for those services. Thus, in one embodiment, update manager functionality 51 may publish information on pub/sub 65 as to the availability updates for gateway appliance and endpoint devices. Similarly, specific service managers or like functionality 75 may publish information on pub/sub 65 as to the availability of updates for the respective specific services.

In one embodiment, the update notice published by the updater, service managers, and/or firmware manager may include, but is not limited to, new configuration version information for latest firmware or software for the specific service or devices. A matching engine functionality of the pub/sub server 65 determines which gateway appliances are subscribed to receive these updates, and generates a notification message 175 that updates are available for receipt at the gateway appliance 10, for example, via IM-like messaging (or any other presence and peering protocol) over the public Internet.

Figure 6E:
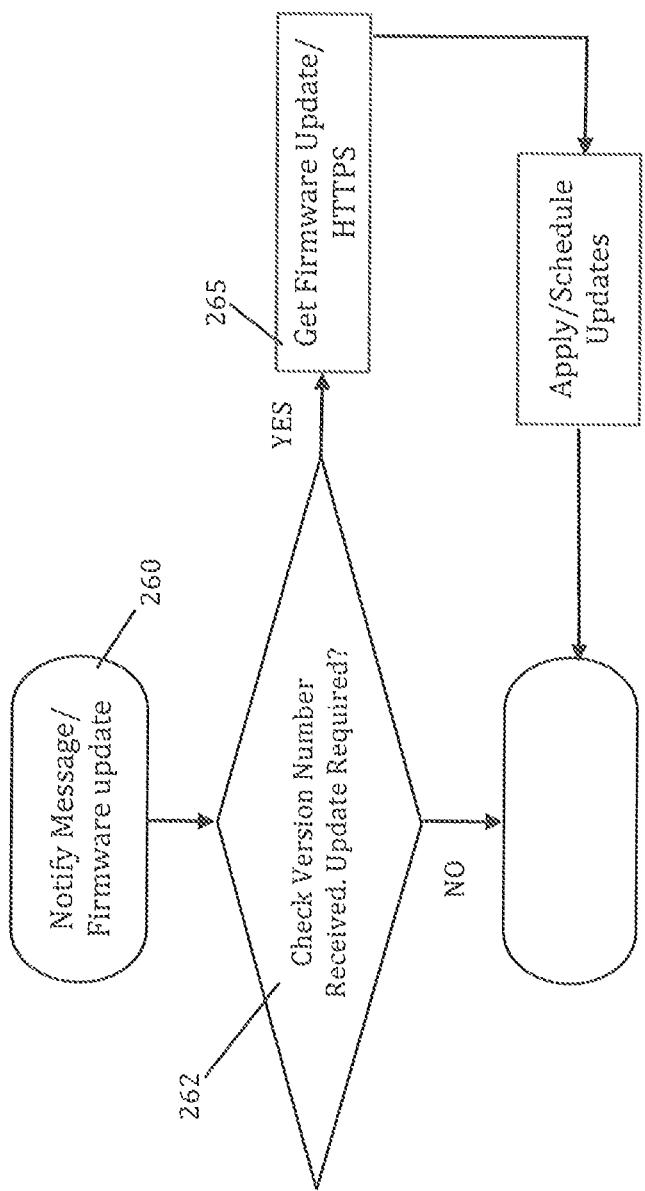

FIG. 6E shows at step 260 the gateway appliance receipt of a notify message indicating the published firmware or configuration update either for itself or a digital endpoint device. At step 262, the gateway appliance makes a comparison against the current firmware version and determines if the update is needed. If the update is needed, the appliance initiates a pull operation to retrieve the firmware update, for example, over a secure HTTPs connection at step 265 and may start or schedule application of the firmware updates at step 267. In one embodiment, a descriptor package helps the gateway appliance interpret the command to obtain the software update, e.g., at a certain location in the networked service center. In an orderly and secure manner, e.g., via HTTPS protocol, each of the subscribing devices may seek out where in the network the published software update resides and once authenticated, via authentication server or like functionality, it will retrieve the software. Referring to FIG. 6D, from the support network perspective, a request is received from each of the gateway appliances, for example, via a web services interface 90, to pull the new firmware version. In one embodiment, this may take place according to a schedule or priority basis. Then, an authentication process is performed, for example, via authentication server or like functionality 71, and once the appliance is verified, the available firmware update may be pulled from the updater functionality 51 (or from individual service managers or firmware update manager or like), and forward to the appliance as shown at 177.

As mentioned above, consumers may subscribe for updates to digital endpoint devices connected to the gateway appliance as well in one embodiment. For example, a user has a certain type of phone and, if there is an update, the pub/sub notification feature or functionality will notify the gateway appliance of the updates available for that phone type. Thus, all of the gateway appliances that have that phone will be informed with service upgrades. In one embodiment, matching engine functionality notifies all the update information concerning operation of the phone device to the subscribers, e.g., like RSS feeds and/or notifies the matching gateway appliance (that is, the gateway appliance determined as having this phone as one of its endpoint devices) of updates, for example, via signal control channel (e.g., using XMPP), for example, when news or updates are received for this particular phone. The matching engine determines all of the subscribers that are subscribed for that service and will put out update notification to the appliances.

Thus, service managers and/or firmware update manager publishes update information availability to the pub/sub functionality, the gateway appliances subscribe to desired updates, for example, by registering the current versions of its firmware and software to the pub/sub functionality, and the matching engine functionality of the pub/sub matches the published data with subscribing appliances and sends notification to each subscribing appliance.'

A pub/sub server may calculate the notification rate for providing the firmware update and sends the information back to the control message router which forwards the firmware upgrade information to the appliance in the form of a data structure, for example, including but not limited to IQSet (a type of XMPP message), upgradeDetails (details for upgrade), downloadTime (time it takes to download the upgrade), and timeToUpgrade (time it takes to install upgrade at the appliance). The firmware updates are then downloaded from the firmware download server via, e.g., HTTPS connection, to the appliance. Optionally, a package download status message may be sent to the component or functionality (e.g., FUM) from which the upgrades were downloaded shown at 344. Further, after installing the upgrade at the appliance or the endpoint device, package install status message may be sent to the FUM or like functionality to notify the status of the latest upgrade installation. The gateway appliance may be reregistered or restarted and the patch installation verified. The appliance may also generate a notification 347 that the firmware upgrade patch has been completed which notice is forwarded to the FUM or the like functionality of support network.

It should be understood that a firmware upgrade throttling mechanism may be provided such that, dependent upon the load status (resource utilization) as determined by the provisioning firmware download server, the firmware update rate may be modified on the fly.

As described above, one or more gateway appliances communicate with the FUM or like functionality to download compatible software for itself and the endpoint devices. In one embodiment, the appliance is responsible for updating the endpoint devices with the downloaded software. A user of the appliance may have an option that is configurable to have updates automatically downloaded when available or be prompted to initiate the download. For instance, when a new version of appliance firmware is available, the FUM or like functionality notifies the appliance either directly or via pub/sub. If the user is configured for automation, then the appliance would initiate download of the firmware. If the user is configured to be prompted, then the appliance notifies the user and waits for an ok from the user. If the user agrees for the update, then ROS would initiate download of the firmware.

In one embodiment, once the firmware is downloaded the appliance performs the automated firmware upgrade when indications are clear that the upgrade will not be interrupting other functions or services provided in the appliance. For determining compatibility with other existing functions or services, the appliance performs a basic set of "acceptance" tests to make sure that the subscribed services are still functional after the firmware upgrade. This may be done, for example, referring to a matrix or table of information regarding compatibility or interoperability among software, firmware, hardware or like of various services, gateway appliance components, and endpoint devices. In one embodiment, this matrix or table of information is received as part of configuration data from the support network, for example, during initialization procedure and during other communication session and may be maintained in the gateway appliance. In another embodiment, the compatibility test may be performed before the upgrades are downloaded, thus necessitating only the compatible versions of upgrades to be downloaded. The appliance in one embodiment has the capability to fall back to a previous release in the event of a software upgrade failure. In one embodiment, as described above, FUM or like functionality keeps track of the various appliances that it communicates with and the firmware version on each appliance. In another embodiment, FUM does not have knowledge of which appliances need which upgrade. Rather, FUM simply publishes information regarding any updates to the pub/sub server or like functionality and it is up to the pub/sub server to notify the appropriate gateway appliances.

Similarly, for the end point device a user may have the option to automate the download or be prompted to initiate the download when an update is available in the FUM, for example. For each appliance, the FUM or like functionality may be responsible for tracking the software version status and upgrade availability for the devices that each appliance communicates with. Thus, in one embodiment, the FUM or like functionality may maintain a matrix that may include, but not limited to the following information: the appliance version; the services enabled on each appliance; currently connected devices on each appliance; the software version currently on each device; and the software versions of the end devices that are compatible with the existing appliance version. When a new version of software or firmware for an end device that is supported on an appliance is available on the FUM or like functionality, the FUM may do the following for each ROS: check to see if the new version is supported on the current version of the appliance firmware; if the new software load and appliance version are compatible, then FUM notifies the appliance if that end device is supported on the appliance; if the user is configured for automation, then the appliance may initiate download of the firmware; if the user is configured to be prompted, then the appliance notifies the user and waits for an ok from the user; if the user agrees for the update, then the appliance may initiate download of the firmware; and if the appliance chooses to download the update, then the FUM or like functionality allows the appliance to download the new version. Once the software or firmware or like is downloaded, appliance may perform the automated firmware upgrade of the end device when indications are clear that it will be not be interrupting the rest of the functions and services. The appliance may perform a basic set of "acceptance" tests to make sure that the end device is still functional after the firmware upgrade in the similar manner described above with reference to the appliance firmware upgrade. The appliance also may have the capability to fall back to a previous release in the event of an upgrade failure.

In one embodiment, as described above, FUM or like functionality keeps track of the various appliances that it communicates with and the firmware version on each appliance and/or its endpoint devices. In another embodiment, FUM does not have knowledge of which appliances need which upgrade. Rather, FUM simply publishes information regarding any updates to the pub/sub server or like functionality and it is up to the pub/sub server to notify the appropriate gateway appliances.

With respect to FUM and specific service managers providing update and configuration information to various gateway appliances and/or network elements, there may be a plurality of ways in which such notification may occur. In one embodiment, different methods may depend on different categories of configuration and upgrade data organized, for example, in the individual FUM or service managers or like functionality. For example, data may be classified into different categories such that for one class of data there should be notification available to all appliances and/or network elements. For this class of data, FUM or service managers or like functionality may publish the available information via the pub/sub functionality and allow pub/sub to determine which appliances or network elements should be notified and handle sending of notifications. Another class of data may be data that is directed to a subset of elements, for example, regional data that are directed to appliances located in certain regions or locales. For this type of data, pub/sub feature may also be utilized. Yet another class of data may be data that is solely for a specific appliance or network element. For this type of data, the service mangers or FUM or like functionality need not utilize pub/sub feature, rather the data may be communicated directly to the individual appliance directly, for instance, using an XMPP control channel, or to the individual network element via interfaces.

Accessibility Testing

In one embodiment, the accessibility testing feature determines whether the gateway appliances are accessible from a signaling point of view, from the support network. The accessibility tester performs an accessibility test, for instance, from a public interface utilizing UDP/TCP/HTTPS and sends the results of the accessibility test information to the requesting one or more service managers. The accessibility tester in one embodiment may test different port numbers on the IP address for accessibility. Once the accessibility test is successfully performed, the service specific manager updates the location server component with the gwid, served, and an "active" indication. The service accessibility response is then forwarded back to the message router for routing ultimately back to the gateway appliance.

Peer to Peer Accessibility Testing

As described above, in certain environments, the gateway appliances are behind a firewall making it difficult to communicate with them from a signaling point of view. From a signaling viewpoint, messages should communicate back and forth between the two gateway appliance devices and ultimately to the digital endpoint device in the home, e.g., sharing or posting a digital photo to grandma's TV, requesting transfer of or sharing list of music lists, favorites, songs, over the Internet between two gateway devices. This negotiation may be initiated via a presence and peering based communication protocol such as an IM-based messaging over the signaling control channel as the network state characteristics of the appliance are known at the support network. For example, the support network may determine whether one appliance is behind a firewall having a private IP address making it hard for the other device to signal back via HTTPS signaling. Appliances have this awareness that it is behind a firewall, for example. Thus, according to one embodiment, a method of negotiating directly over the control channel to establish peer-to-peer connectivity, i.e., a peer-to-peer accessibility testing feature functionality is provided to ensure service accessibility. Thus, in one embodiment, the peer-to-peer accessibility testing feature negotiates and creates using a control channel, a media path to share data between the peers.

In another aspect of peer-to-peer accessibility testing, an accessibility tester or like functionality may request one gateway device to determine whether it can talk to another gateway device, for example, for determining whether that another gateway device can receive inbound services. In operation, the accessibility tester functionality via, for example, message routing functionality sends a message to one gateway device to ping or try to access in other ways a second gateway device. The message may, for example, include each gateway device's identification information and access details such as IP address and port number. The requested gateway device then pings the second gateway device to determine whether it can reach the second gateway device and sends the results back to the accessibility tester functionality.

Gateway Appliance to Gateway Appliance Communications

Figure 6F:
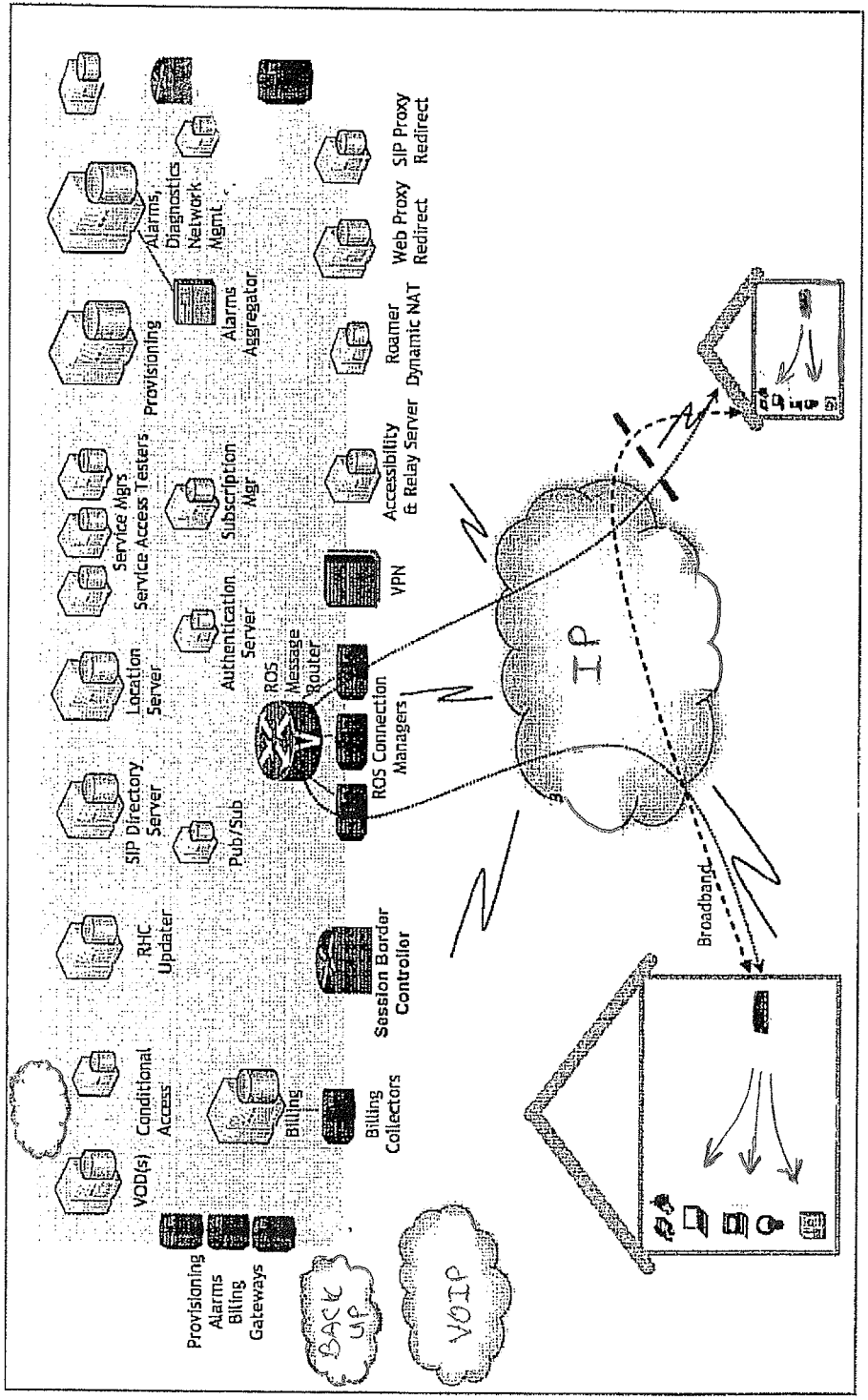
FIG. 6F is an architectural diagram that illustrates an overview for communicating or sharing between the gateway appliances in one embodiment.

Another feature made available in the system and method of the present disclosure is communication capability between the appliances. This feature, for example, may be utilized for enabling secure peer-to-peer sharing of data between or among the gateway appliances. FIG. 6F is an architectural diagram that illustrates an overview for communicating or sharing between the appliances. In one embodiment, signaling information is communicated via the signaling control channel, for instance, using XMPP, and then the gateway appliances $10$, $10_n$ negotiate the subsequent transfer of media or data path. In one embodiment, this media or data need not travel via the signaling control channel. Thus, for example, HTTPS path may be negotiated between the appliances $10$, $10_1$.

Services

As mentioned, FIG. 2A describes the high level service framework upon which are built services 130, e.g., downloaded via the support network as packages that are developed and offered by a service entity for customers. These services may be offered as a part of a default service package provisioned and configured at the gateway, or provisioned and configured subject to user subscription and may be added at any time as plug-in service modules in cooperation with the service center. It is understood, however, that while the gateway appliance includes much of the intelligence or service logic for providing various services, it is also possible that for some services, some or all of service logic may reside in the support network and/or with a third party provider.

Backup and Storage Services

The gateway appliance interoperating with the network support may further provide data backup and restore services. For instance, the gateway appliance may include a user interface and application or like functionality for allowing users to select files, for example, stored on user's PC, on the gateway appliance or other endpoint devices for the backup and restore services. The term "file" as used herein comprehensibly refers to files, folders, directories, any data in any format, for example, media, ascii, etc. The gateway appliance may encrypt and compress, and transfer the files to a backup storage. In one embodiment, the backup storage is a storage provided by a remote third party backup service data center. In this embodiment, data is backed up to and restored from the backup service data center, for instance, via interoperating with the support network, which, for example, interfaces to the remote third party backup service data center. In another embodiment, this backup storage may be at the gateway appliance itself, for instance, on the non-user accessible region of the gateway appliance storage that is only accessible by the services support network. Yet in another embodiment, files may be distributedly backed-up on the non-user accessible region of other gateway appliances, for example, which may reside at other premises (it should be understood that one premise may have more than one gateway appliances). For instance, a file may be divided into multiple parts and each part may be backed up on different gateway appliances. Further, one or more parts may be backed up redundantly, that is, on multiple gateway appliances. Combinations of any of the above-described embodiments may be utilized for backup and restore services. In one embodiment, a user may provision and subscribe to the type of backup services desired with the provisioning and/or subscription service as described above.

Two-Stage File Back-Up

In one embodiment, the gateway appliance and support system architecture provides a file management feature generally including functionality that enables a user to back-up files or content to a virtual memory storage area provided in the gateway appliance, and then subsequently forward the backed-up files to an external wholesale service provider providing the backup service. Thus, gateway storage device provides the protected storage for user files and user content at its side of the demarcation point in a two-stage storage process: 1) storing the content across the virtual demarcation point (partition); and then encrypting the content; and 2) dispersing the stored content to other gateway appliances, or at another storage location provided by the service center or by a partnered $3^{rd}$ party back-up storage service provider. This could be performed automatically or on a scheduled basis. The gateway appliance knows where the pieces will be stored based on the service configuration and subscription. The locations of appliances that may back up content pieces are known at the network level, e.g., hardware IDs of each of the gateways are known based on the unique identity of the appliance, and the mappings of the IP addresses that change dynamically of the appliances are known at the location servers so the location of backed-up content for a user is always known.

It is understood that, in connection with the implementation of back-up services provided by partnered third party providers, for example, the gateway appliance is configured to communicate with the back-up file service provider via the web interface and thus requires the URL of the service provider for where the gateway should communicate. Configuration data is provided to the gateway appliance from the subscription manager as part of initialization process that queries the service providers to obtain configuration data that can be sent back to gateway appliance, and tell which versions from configuration perspective to report back to the appliance. For back-up services, this may be a version 1 at URL 1 so the gateway appliance should go to this location or, based on location of the gateway appliance, may be sent to URL 2. For each service, configuration data is provided to the appliance. This is all based on handshaked communications. When the user invokes the service, the gateway appliance knows all that it needs to invoke the service.

As controlled by the service center, in an alternate embodiment, the encrypted content to be stored are transmitted to another gateway appliance's storage locations beyond the respective demarcation points for storage thereat the other gateway appliances in a distributed, safe, and redundant manner. That is, each file may be partitioned into a plurality of pieces for further transfer or storage in a redundant and secure manner, e.g., and transferred to the service control partitions behind the demarcation point. These pieces may then be encrypted and sent out externally for further storage, automatically, e.g., at time of log in, on a scheduled basis, or upon user initiation.

Web Butler

The gateway appliance is provided with a service that functions as a proxy for taking action on a user's behalf and includes the computer readable instructions, data structures, program modules, software agents, and objects that may be integrated with the actual service packages as a user feature. This proxy function may be configured to automatically upload pictures, for example, to a service provider via service module located at the device, or taking actions for other services on a user's behalf. Via the web butler proxy, implementing a search or in accordance with a user subscription, content from different internet-based media feeds (e.g., free content) may be aggregated and automatically downloaded to the gateway appliance.

Automated Failure Recording and Recovery and Rules Based Notification Services:

The gateway appliance is provided with a service that provides maintenance aspects of the gateway architecture managed at network service level. Such a service comprises automated failure recording and recovery platform management whereby a rules-based engine will be automatically notified and queried to implement a fix upon the detection of a system or service failure. The rules-based engine comprises a fix in the form of a process that may be performed at the service framework and/or platform management levels for each type of service failure. More particularly, the rules based engine is provided as part of the service management feature through the platform management heartbeat connections with processing threads. Upon detection of a failure or alarm by the platform manager component, the rules based engine will be requested and request what actions to perform, e.g., a sequence of rules that would direct functionality to go to network and get new firmware upgrade, for example, or go back to previous firmware version or configuration based on the rule specified to render the service operational. This will enable a service to be always available with service failures automatically addressed without having to restart platform. Additionally, notifications are sent to the service provider when failures occur at the appliance.

File Sharing Services

File sharing service of the present disclosure in an exemplary embodiment allows users to share files, for example, pictures, music, videos, documents, presentations, grocery list, bookmarks, etc., with friends and family members or other users. The files can be shared with user's "buddy list" or other contacts maintained at the gateway appliance at a premise such as the home. Once users are authenticated, the gateway appliances may communicate with each other, for instance, using the mediated or negotiated media or data path between each. Gateway appliance may also track functionalities that the user is enabled to do, e.g., send photos at a digital picture frame to a buddy or other gateway appliance of a member of a community of interest, e.g., a family or friend, or share a picture for display on a television of a buddy.

In one embodiment, presence and peering messaging protocols such as IM-based protocols may be used for sharing, and may interact from a protocol perspective, to push to a subordinate device at another gateway appliance, e.g., a digital endpoint such as a television or digital picture frame. To accomplish this, a negotiation is made to determine who transfers what to which device based on the stored rosters, and determine a signal path to accomplish the transfer accepting files for users in the home, and a process for acceptance of files for a particular user at the home, e.g., specific files may be accepted for some user devices to the exclusion of other devices, e.g., belonging to a teenager or minor.

In this manner, for example, a file sharing (e.g., pictures, documents), movie list sharing, music playlist sharing, application sharing, and video cam sharing, all can be a managed by the community or network of gateway appliances that are designated as buddies. The gateway appliance, in one embodiment, maintains directories of access and sharing and which services are involved to access and transfer content.

In addition to sharing data and files with different gateway appliances and endpoint devices connected thereto, data and files can be shared among the endpoint devices connected to the common or same gateway appliance. Thus, for example, a photo stored on a PC can be transmitted to a digital picture frame on the same gateway appliance network, emails received via the PC can be displayed on the television connected to the network, etc.

Additional examples of functionalities associated with file sharing on a gateway appliance may include, but is not limited to: allowing a user to tag or add comments, descriptions to the files for sharing, allowing friends and family or the like viewing the shared file to leave their comments, providing scratchpad function to share, allowing users to share widgets, RSS feeds, and tabs on their personal page with family and friends or the like, allowing users to create slideshow with media and share it with family and friends or the like.

File sharing functionalities may be performed manually, semi-automatically or automatically. For example, in addition to allowing users to select files and one or more user or user groups for sharing, there may be provided a personal page access or the like, which, for example, may present the user with predefined parameters for sharing such as files or folders designated previously for sharing, and a list of contacts preset for sharing. The list of contacts may have been imported from other applications such as email or IM buddy lists and/or entered manually. Thus, with a set of predefined parameters in place, file sharing may be invoked with minimum user interaction, for instance, as one-click function. In another aspect, file sharing functionality may be setup such that, for example, when a change or new file is detected, the file sharing is invoked automatically. For example, a file or folder may be designated as an automatic share file or folder, and if any change in the data of that file or folder is detected, file sharing is initiated automatically.

Figure 3A:
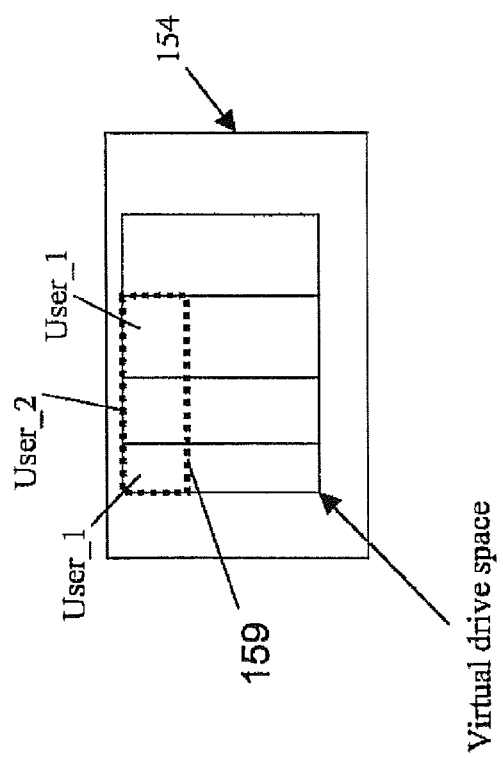
FIG. 3A conceptually depicts a virtual hosting (space-sharing) service provided by the gateway device of the present invention.

In a further aspect of the invention related to file-sharing, the gateway appliance and support system architecture provides a hosted service-virtual space on the centralized disk storage at the gateway for users. Dedicated areas of user storage may be designated as shareable including application level sharing for any application that has data. As shown in FIG. 3A, this virtual storage area 159 may be combined from its internal hard disc storage with any network attached storage device located at the network to create a single virtual file system that consumers can use like a single drive.

Through the roster or buddy list enabled by the peer and presence messaging protocols implemented over TCP, the users may dynamically share in a virtual space via their PC or other endpoint devices connected with the gateway. Any type of data may be shared including user generated data such as, but not limited to: files, photos, slide-shows, video and audio files, .mp3 playlists, web-links or bookmarks, or any information (e.g., web-blogs, comments, discussion forums, personal information, and to-do lists) via secure gateway to gateway communications. Thus, for example, via the gateway, buddies could configure RSS feeds to their personal page on this share space. The shared file is at virtual, programmatical area in application level space at the gateway. This data or file or information to be shared may be designated by the user and tagged, via an endpoint device user interface, to indicate the data or file to be automatically stored at the virtual file location for that user or information as shared content. The shared content communicated may have associated privileges depending upon the recipient, e.g., content is delivered with permissions given, e.g., read-only permission, or an update permission, e.g., to invite comments for sharing or discussion among buddies, at the virtual level. Thus, the invention provides for community sharing with a built in management structure that enforces service subscriptions for such service.

Coupled with permissions functionality whereby connected users may have permission sets associated with them, a dynamic virtual space sharing environment is provided where select users can be notified of certain events on a scheduled basis, for example. Permissions are enforced locally on a buddy by buddy basis, e.g., privilege granted to add comments via the messaging infrastructure. The gateway provides a granular privileged support, e.g., read, write only, update privileges, etc., and the notification may be via telephone, IM, e-mail program, etc.

Via the file-sharing interface provided by the gateway, buddies could "subscribe" for changes to such shared spaces. When there are changes or additions to the subscribed share space, the buddies will get notifications through email or IM or through their personal web page. Thus, if granted the privileged, via the peer and presence communications protocol implemented, a notification may generated that is packet transferred to the buddy's gateway device via TCP for indicating to a user that shared data is available. For example, that a shared space session is being initiated by a buddy, e.g., for purpose of sharing an application, or adding comments.

Other functionalities include, but are not limited to: viewing a to-do list on TV, or providing scratch pad capabilities; and sending a signal from the gateway appliance to generate for display at the TV device the to-list or any user generated data, via messaging infrastructure, provision of a single click-share service. This is especially applicable for VPN closed user groups environments via a VPN providing a virtual closed network environment within which users (buddies, friends, family) may interact, e.g., share a common interface to enable real-time video gaming.

As mentioned, file sharing may occur between and among different digital endpoint devices, among different gateway appliances, and among different digital endpoint devices associated with one gateway appliance and various endpoint devices associated with another gateway appliance, etc. For instance, a user may send a photograph (or any other file or media) from a mobile phone (or other digital endpoint devices) to a gateway appliance. The gateway appliance may forward that photograph to another digital endpoint device connected to the same gateway appliance. The gateway appliance may forward that photograph to another gateway appliance, which in turn may forward the photograph to an endpoint digital device associated with that other gateway appliance, for instance, another mobile phone, a digital picture frame, a PC, etc. As digital endpoint devices may include WIFI or other wirelessly enabled digital cameras, sharing of files from those wirelessly enabled digital cameras may occur in a similar manlier.

Remote Web Access

Remote web access feature in an exemplary embodiment allows a secure mechanism to connect to and access the gateway appliances from anywhere through the web. A public web proxy/redirect servers or like functionality of the present disclosure in one embodiment provide HTTP redirection and proxy services for public web access to the gateway appliances. In one embodiment, for the gateway appliances that reside behind external firewalls, VPN accessibility is provided. In one embodiment, a user may access a web page provided by the web proxy/redirect servers. The user is prompted to enter information such as user identifier (ID) and password. Steps are initiated to enable establishment of a path or channel via which the information may be safely exchanged that enable a secure communications session to be established between the remote web browser and the gateway appliance. For example, the web proxy/redirect server encrypts the user information (e.g., ID and password) and transmits the encrypted information over the always-on control channel described above to the target gateway appliance, that is, the gateway appliance the user is attempting to access via the remote web. The gateway appliance then authenticates the user ID and password, that is, determines whether the user ID and password are valid for accessing the gateway appliance. If the user ID and password are valid, the gateway appliance communicates to the web proxy/redirect server that the user can access the gateway appliance. The web proxy/redirect server in turn provides the IP address for the gateway appliance to the user for directly connecting to the gateway appliance, for instance, via secure HTTP or HTTPS connection. In one embodiment, all service decisions with respect to further communications are decided at the home appliance. Thus, a user may remotely order a movie and have it downloaded to the user at his/her gateway appliance or remotely control home automation devices for controlling various devices at a premise.

IM Server

As mentioned, the gateway appliance is the central communication platform that interoperates with multiple devices in the home to form a home networking environment. In the context of home automation, the gateway appliance 10 is additionally provisioned with a home automation controller device that communicates with the IM server function to facilitate home network management, including: a home automation controller that interfaces with a TV/Web interface that interfaces with the digital media adaptor component and a device driver (e.g., USB) that interfaces with the home automation network (e.g., Zigbee network) via a home automation control node that is responsible for communicating with the "smart" devices designed for home automation. The digital media adaptor component further communicates with the TV device at the premises, and the TV/Web interface further interfaces with the computing device, e.g., PC at the premises. Further, the IM server functionality interfaces with an IM client that is either local (at the premises) or remote and may include a SIP phone or a PC.

In the context of home automation services, the appliance supports multiple types of home automation controllers and multiple protocol standards including a variety of non-IP protocol standards and vendor specific proprietary protocols such as Insteon, Zwave etc. This enables the user to integrate multiple vendor devices in the home. It is further understood that the controller device itself may support more than one automation protocol such as Insteon or (legacy) x10 devices and these protocols will be transported via RF or electrical path. The gateway appliance only communicates with controllers via vendor specific protocols.

Gateway_appliances are able to communicate with each other to share information through this IM server functionality provided at the appliance. All the messages and commands are communicated through a secure network connection.

Appliance GUI

For ease of operation, the appliance provides a GUI interface that supports functional test, diagnostics, and control capabilities for itself and for the other home network devices that it communicates with. The test and diagnostics include logs, statistics, and alarms (alerts) for use by service support centers and users. The control capabilities include automated configuration and management. To this end, users of gateway appliances $10, \ldots, 10_n$ accesses the web/internet via a personal computer/computing device, mobile or laptop computer, personal digital assistant, or like device implementing web-browser functionality, e.g., Firefox 1.5 and Internet Explorer® 6.0 or later, or other browsing technology that may be compatible. In an exemplary embodiment, the browser interface employs the latest user interaction techniques, e.g., Web 2.0, and implements web development technologies such as AJAX (Asynchronous JavaScript and XML).

With respect to accessing the gateway appliance and services via a web interface, users will log-in to a home page screen (not shown) via a web-based communication by entering a username and a password. Upon submitting this login information, both the username and password will be validated. If either the username or password is invalid, then an appropriate error message is displayed explaining the nature of the error. If the login is successful and the gateway appliance has already been initialized, a user's personal page will be loaded by default which page is user is configurable. A tooltip functionality is provided for more details about the status. If the status is red, the user can select the status indicator to get a diagnostic screen with a network map (not shown). This screen will display the current status of all devices managed by the gateway appliance and includes a button to allow the user to test the current status. A top bar is also used to indicate the progress status of any backup jobs currently running. A tooltip is provided to indicate the schedule name and the progress percentage. The top bar is also used to indicate the space usage of the user. A tooltip is provided to indicate the percentage of the space used by the user of the allocated space configured by the administrator user. There is a label provided that displays the current user information (e.g., administrator), and next to the label is a link to logout of the home center. When the user clicks on the logout link, the users' web session will be invalidated and the login page will be displayed. A further link is provided to change the user preferences. For example, when the user clicks on the "Preferences" link, a dialog box will be displayed that will allow the user to change the user preferences settings such as color, font, and themes.

If the feature represented by the icon is not available, then the icon will be grayed and a tooltip will be provided to display an explanation. Although not shown, notifications for each feature are displayed as an animated icon below that feature in the second bar. A tooltip is provided with more details for each notification. When the user clicks on the notification icon, that feature page will be loaded to display the detailed notification information.

Home Automation Services

In the home networking environment, the gateway appliance operates as the management center for managing the various services and devices that form the home network. One of the services offered by the gateway appliance is the home automation service. Via a home automation page, the user is enabled to view and manage the home automation devices. The home automation service is enabled/disabled by the service center. When enabled, the gateway will be able to communicate simultaneously with multiple home automation vendor controllers installed in the home. If the installed controllers are supported by the gateway, they may be automatically discovered by the gateway. When being provisioned, the following elements are processed: 1. system configuration; 2. map builder; 3. event builder; 4. scene builder; and 5. group builder.

System Configuration

When the gateway appliance is first introduced in the home network and if the home automation service is enabled by the service provider, then the gateway appliance detects and automatically discovers the following components: all the controllers that are part of the home automation network and whose protocol is supported on the gateway appliance; all the end devices supported on each of those controllers; and the firmware versions on each controller and end device. Once the controllers are detected, the gateway appliance allows the administration user to configure the detected controllers. As mentioned herein, once the controllers have been detected and configured, the gateway appliance updates the Firmware Update Manger (FUM) with the controllers and end devices supported on the home network along with their current firmware versions. For each gateway appliance on the managed network, the FUM maintains the knowledge of the controllers and end devices. It is the responsibility of the FUM to keep track of firmware updates for controllers and end devices and inform the gateway appliance when an upgrade is available. The gateway appliance additionally maintains a table of the controllers and supported end devices on each controller. This is later associated with user defined labels used for the GUI display as will be described in greater detail herein.

Map Builder

The map builder component provides the computer readable instructions, data structures, program modules, objects, and other configuration data for enabling a user to configure the home automation service. In this process, two types of maps are generated: a general map and a detailed map. The general map allows the user, during configuration, to label end devices, i.e. "stairway lamp", "joe's dimmer desk lamp", "downstairs HVAC unit", etc. The user selects or designates a specific device and can turn it on, off or change it to a specific setting (for example, set the "joe's dimmer desk lamp" to 50% power, set the thermostat of the "downstairs HVAC unit" to 75 degrees). The detailed map extends the capabilities of the general map by including a floor plan to associate with the labeled end devices and enables the following: 1) constructing a floor plan of the house; 2) labeling end devices, i.e. "stairway lamp", "joe's dimmer desk lamp", "downstairs HVAC unit" etc.; and 3) associating devices with specific rooms by dragging and dropping icons in specified locations in the room. The user may also generate an automation network map of the home and select a specific device and turn it on/off or change it to a specific setting (for example, set the "joe's dimmer desk lamp" to 50% power, set the thermostat of the "downstairs HVAC unit" to 75 degrees). An administrator/user has the ability to create two types of maps: home automation network map (termed as "network map") and the controller map that is used by authorized personnel (service provider/home user) for diagnostics. The network map includes the gateway appliance, all the controllers, and all the controlled devices in their specific location; and the controller specific map (termed as "controller map") includes the map of each controller and the devices controlled by that controller.

Thus, the gateway appliance supports a map builder process to enable the admin/user to build the maps. In this process, a user is enabled to: 1) create a floor plan of the house; group each room as part of a section such as "upstairs", "downstairs", "east", "west", "basement" etc. If the user does not want to use the section, the default value can be "downstairs". Then it shall be possible to label each room with an appropriate name such as "Joes' room", "living room", "kitchen", etc. Hence, the gateway appliance may provide a list of standard labels as given below: living room, formal dining, family room, kitchen, breakfast room, second living room, third living room, foyer, front porch, patio, <username> bedroom (this label could be used multiple times with a different username), master bedroom, master bath, hall bath, <username> bath (this label could be used multiple times with a different username), media room, and user specified.

Each of the icons representing the controlled devices can be labeled with a unique user defined label (such as Joe's desk lamp, kitchen lamp, etc.), or comprise standard labels. Each of the controlled devices is additionally assigned status indicators. The gateway appliance shall provide pre-defined status indicator templates for each type of end device (e.g., if the lamp has a dimmer switch, then that lamp will have a dimmer switch template). Hence, the status indicators are assigned either automatically (gateway appliance communicates with the controller and get the status indicators for each end device) or manually (the user would have to assign the status indicator). Examples of status indicators include, but are not limited to: on/off for a lamp, dimmer setting on the lamp, temp for A/C/heater unit, etc. The gateway appliance may provide a set of standard status indicators as well as shown in the table below.

| No. | Device type | Status indicator |
|---|---|---|
| 1 | gateway appliance (performance statistics) | Packet throughput statistics (WAN/LAN, AP)<br>temperature conditions of the system board(s)<br>disk usage<br>disk frag<br>Process management (to be displayed only to the service provider):<br>  1. All processes running on the gateway appliance<br>  2. All configuration<br>  3. Start/stop control of all processes running on the ROS<br>IM agent:<br>  1. Each IM user client<br>  2. Status and statistics for IM-based notification services |
| 2 | Automation controller (map display) | Status of each end point device connected to each controller |

| No. | Device type | Status indicator |
|---|---|---|
| 3 | PC | Connected/Not connected; last time back up was done; last time file was shared |
| 4 | Phone | Last reboot date; Last registration date; operational status |
| 5 | Media adaptors | File formats supported; Max throughput allowed; DRM supported; operational status |
| 6 | MOCA adaptor/HomePNA | Node configuration; MAC control parameters; PHY control parameters; Vendor ID parameters; traffic statistics; operational status (what channel etc) |

Event Builder

The gateway appliance supports an event builder process to further automate the home by enabling detection of an "event" that enables/disables the activity of a device. Example events may include, but are not limited to: rain threshold exceeded, an alarm going off, or motion detected by the motion sensor. For example, a trigger maybe set to turn off the sprinkler system if a "rain level exceeded" event occurs. Another example is to record a video snapshot if a motion detector event is received. When an event enabled through the event builder gets activated, the user is notified. An event trigger is built as part of the set up procedure. This builder includes events that when detected will trigger an action, e.g., to automatically enable/disable the activity of a device such as shown in the Table below:

| Trigger events | Triggered actions |
|---|---|
| Rain threshold exceeded | The sprinkler system is deactivated until the rain threshold level is not exceeded |
| Alarm goes off | The alarm is again set for activation to the preset configuration until deactivated |
| Motion detected by the motion sensor | Captured on the camera/Light comes on |

Scene Builder

The gateway appliance supports a scene builder process to enable the setting of "scenes" or scenarios enabling users to control multiple devices simultaneously. For example, the user may have a "sleep time" scene, either scheduled to occur automatically or invoked by the user at a certain time. When the "sleep time" scene is invoked, lights are automatically turned off, blinds are drawn, thermostats are adjusted, night lights are turned on, etc. Instead of the user manually moving about the house and making these adjustments, the user schedules this automatically in the gateway appliance or the user will simply invoke this scene via a web-based graphical user interface. The scene builder enables a user to: construct, modify, or delete scenarios, schedule scenes to be automatically or manually invoked, obtain a status check or user control of constructed scenes from all local and remote interfaces, and create user defined scenes. The gateway appliance includes a default scene builder for the user to use and modify if needed. One exemplary default scene builder is configured as shown in the Table below:

| | Lighting | | Thermostat | Blinds | |
|---|---|---|---|---|---|
| Scene | Device labels for the rooms | Dim Setting | Zone number | Temp def F. | Device labels for the rooms | Raise % |
| Night scene | Living room Lamp1 | 50% | 1 | 75 | Kitchen blind 1 | 0 |
| | Kitchen lamp 1 | 100% | 2 | 85 | MB blind 1 | 100 |
| | | | 3 | off | | |

Preferably, the device labels for this default scene builder is constructed based on the labels that the user has created while building the network map.

Group Builder

The gateway appliance supports a group builder process to enable the grouping of items together and give it a labeled name. All the devices in this group will go to the same state. This is in direct contrast to the "scene builder" where all the devices included in a scene may be set to different levels. If light 1, light 2, and light 3 are in a group, then a single command (e.g., "ON") executed on the group will cause all the lights in the group to be in the "ON" state. Alternately, in another group configuration, if light 1, light 2, and light 3 belong to a "night scene", then when the night scene is invoked, light 1 could be at lit at 50%, light 2 at 20%, and light 3 may be "OFF". The built group may become a part of a scene which can be invoked automatically or manually, or be invoked as a group whereby all the individual components are set to the same final state.

Controller Status Indicators

In order for the user to control the various automation devices, it is important that these devices are monitored on a regular basis and the result of the monitoring is displayed to the user. The status indicators of the controlled devices provide a means to monitor the automation device. The home automation controllers are capable of tracking the status of the devices that it controls through the methodology implemented to communication between itself and the devices (e.g., z wave/Insteon protocol). These controllers may communicate with the end point devices using multiple protocols. Some of these protocols may have a "closed loop" design, i.e., the devices provide acknowledgement back to the controller so that if the acknowledgement is not received, the controller retries the command (e.g., the Insteon protocol). These types of controllers can send control and simple data between devices (i.e., a light switch turning on multiple lights/devices) within the home. To give an example of the above mentioned scenario, assuming that the controller is controlling an Insteon-based lamp A, the gateway appliance knows (through status indication) that the lamp A is on and communicates to the controller that lamp A needs to be turned off. The gateway appliance tells the controller to turn off lamp A; in response, the controller (e.g., Insteon based) transmits this signal (RF and/or electrical) to the physical entity lamp A; when the lamp goes off, then the controller gets an ACK/NACK back from the device acknowledging that the lamp A was turned off/not turned off (if the end device is an X10 protocol-type device then there is no acknowledgement received); the gateway appliance then updates the status indicator of the device depending on whether it was an ACK/NACK. Thus, if the ACK/NACK is not received within a configurable period of time, then the gateway appliance reissues the command to the controller and restarts the timer. If there is no ACK/NACK received by the time the timer expires, then the gateway appliance alerts the user.

The gateway appliance polls all the controllers at a configurable time interval, e.g., 5 minutes. Alternatively, the gateway appliance may receive events from the controllers informing gateway appliance of the status of the end devices. Either way, the gateway appliance maintains the status of the devices based on the polling/event result. The status of each device is reflected on the network/controller map. For all X10 devices, the status indicates a value of "unknown".

If a controller was configured by the user as a managed device but the gateway appliance does not receive any communication message from the controller, then the status indicator reflects the lack of communication. If an error code is received from the controller, then the gateway appliance either translates the error code and displays it in common language or directs the user to a help page where the error code is explained. If a controller is able to detect (possibly through an error code) that a managed end device is not responding to it, then gateway appliance interprets that detection and conveys it to the user by either displaying the error in common language or directing the user to a help page where the error code is explained.

When the gateway appliance receives an indication from the user through any of the access methods to execute a particular command on a device or a group of devices, the gateway appliance responds by performing the following: it maps the user command to a corresponding message to be sent to the controller and then sends the message to the controller; and it waits for the acknowledgement message from the controller for a configurable preset period of time. If the message is received within the pre-set time period and the message indicates that the activation/deactivation was a success, then the gateway appliance sets the status indicator of the corresponding device based on the message. If the message is received within the pre-set time period and the message indicates that the activation/deactivation was a failure and a reason code accompanied the failure indication, then the gateway appliance maps the reason code to a user friendly message and displays the message. If no reason code was indicated in the failure message, then the gateway appliance displays the message "unknown reason".

In the event that the controller did not get an ACK back from the controlled device, the controller may send a NACK message to the gateway appliance indicating that the device did not respond. When the gateway appliance receives this message, the gateway appliance displays the message "device not responding" to the user and does not change the status indicator of the corresponding device. If the acknowledgement message is not received within the pre-set time period, then the gateway appliance retransmits the message one time and restarts the acknowledgment timer. If the controller does not send an acknowledgment message the second time before the timer expires, then the gateway appliance displays the message "acknowledgement not received" to the user and does not change the status indicator of the corresponding device.

The acknowledgement message is received after the acknowledgement timer expires, the gateway appliance ignores the message.

User Access and Control

The home automation device is accessible remotely or in-home. Each of these accesses can be enabled through multiple interfaces as defined in the following table:

| Interface No. | Type of interface | Remote access | In-home access |
|---|---|---|---|
| 1 | Web | X | X |
| 2 | IM | X | X |
| 3 | phone (touchtone, IVR) | X | X |
| 4 | TV | | X |
| 5 | Manual | | X |
| 6 | Remote controller (vendor supplied) | | X |
| 7 | A Mobile device | X | X |

The administrator has the ability to enable or disable remote access of any of the automation entities given in this table. As defined herein, the home automation feature is password protected. The system supports two levels of user access, User and Administrator. The administrator is able to perform all operations, including setting privileges for each user. The system implements default settings for each new user.

The methods of access and control is individually enabled or disabled by the administrator. For example, a user may have access to see the status of the automation device, but not reset the devices. The gateway appliance supports configuration and provisioning activities via the remote access (through the web) as defined herein. Thus, when a gateway appliance is powered up in a home, an administrator/user who has remotely, through the web, logged into the home automation service on the gateway appliance is capable of configuring the gateway appliance.

Web Access and Control

Via a web-based interface providing access to gateway appliance functionality, the gateway appliance generates a map-like view of the automation devices and their status. Wherever possible, the graphical user interface device status provides graphical representation of the current status, i.e. "light on" "light off", door open, etc. When accessed via the web, the system provides a menu driven method of control, or a map driven (network map and controller map) method of control. An administrator/user may be responsible for setting the remote access privileges for all the users. When the control is menu driven, the display consists of: a device name (such as lamp, blinds); a room label on the device (Joe's desk lamp, kitchen blind); a status indicator (lamp dimmed 50%, blinds raised 50%); and an action to be taken. The following table presents example room labels such as described herein and the examples of status indicators for each devices:

| Device name (including room label) | Status indicator | Action to be taken |
|---|---|---|
| Blinds | Raised: 0%, 25%, 50%, 75%, 100% | Raise what % |
| Lamp | On/off<br>Dim - 25%, 50%; 75%; off | Switch on/off or Dim what % |
| Door | Open/Close | Open/Close |
| Garage door | Open/Close | Open/Close |
| Window | Open/Close | Open/Close |
| Alarm | Motion sensor - on/off<br>Front door- open/close<br>Back door- open/close<br>Window1- open/close<br>Window2- open/close<br>Window3- open/close<br>Garage door - open/close | On/off<br>Open/close |

Each action entered by the user is recorded temporarily and once the user has input all the actions and confirmation is received to apply the actions, then the actions are executed. After the actions are executed the web page is refreshed with the updated status indicator.

Access to the network map of the home automation system may be governed according to privileges where users have the ability (privilege to be set by the admin) to view the network map of the home automation system through the web. The status indicator of each device is displayed on the network map. Once the network map is displayed, the user is able to change the setting on each device. The user does this by clicking on the device that he/she wants to set. At this point, a configuration window is displayed to the user that includes the status indicator parameters that can be changed by the user. Once the user completes configuration of all the chosen devices to the new setting, an updated view of the network map is displayed to the user without the user having to refresh the view. The administrator or user is additionally enabled to zoom in on a particular controller on the network map and view in another window the controller map which displays each device that the controller controls. The status indicator of each device is displayed on the controller map.

IM Access and Control

A gateway appliance has the ability to connect to the home automation service in the gateway appliance device through IM from a PC or any other IM interface that is supported. Particularly, the gateway appliance is configured to appear as a buddy in the user's buddy list. The name for the gateway appliance IM buddy client user agent as it appears on the buddy list is configurable.

Once the user clicks on the gateway appliance buddy the following events are initiated: the user is entered into an IM "chat" mode; a menu option with "home automation" as one of the options is displayed to the user; and when the user chooses the "home automation" the user is prompted for a password. Once the password is authenticated, the user is capable of asking status, and then changing status and optionally receiving notifications via IM. An example IM interface dialog is presented to the user that will display one or more of the following: whether any unexpected events have occurred in which case the user may be prompted to enter an instruction; request a status check; change a device status; and review an event log. In one example, upon selection of change device status request, the user will be prompted with choices for selecting a device type, e.g., light switch; garage door; outlet; sprinkler system; or a main menu option. Furthermore, in one example, upon selection of a device, e.g., a garage door selected, the user will be prompted to select the actual garage door, e.g., door 1, door 2, and main menu. Thus, the user interaction is text based and menu driven.

TV Interface Access and Control

The TV interface support both menu option and network map options as described herein. The user is able to designate particular events and their updates (such as time and temperature) to be continuously displayed on the TV when a media is playing on the TV. The TV interface displays notifications of events as designated, e.g., A/C breakdown; water leak; and motion detected.

Telephone Interface and Control

The user is additionally able to connect to the home automation service in the gateway appliance device through dialing their home number, e.g., a 10 digit home number. A sequence of events may be executed in response to a received call that has been answered, e.g., the call is considered answered if the voice mail gets connected. The user may be given the option to escape out of the voice mail if so configured. The menu option for IM with text to speech conversion is available and shall be offered when the home automation choice is selected; the user is prompted for a password. If the right password is entered, then the user will receive a confirmation, e.g. an audible tone, to the user that he/she is in the home automation command interface. The same commands offered in IM with text to speech conversion are offered for the phone interface.

Once the user connects to the gateway appliance, then the user is connected to a menu driven IVR type or functionality. The menu presented is exactly the same as the IM interface as described herein. The home automation interface on the gateway appliance is deactivated when the phone goes off hook. The home automation interface on the gateway appliance is activated even if the voice mail picks up the call.

Mobile Device Interface

The system optionally supports WiFi-IP for interacting with mobile devices. Thus, a user may access the home automation service through a HTML supported mobile in a manner similar to the web interface as defined herein. Additionally, the user screen is modified to fit the mobile device. For example, the users may optionally connect wireless IP cameras to the gateway appliance system and stream or store IP video and review this data from a web or TV interface.

Home Automation Services GUI

A home automation page can be generated to display the following for all of the controlled devices: 1) the user defined name for the device, after the devices are automatically detected, the gateway appliance will default the name to the type and the user can modify the name by using inline editing; 2) a status indicator icon or label indicating the current status and possible value of the device; 3) a user defined room in which the device is located, when the devices are automatically detected, the default room will be the empty, however, the user can change the default room by using inline editing; 4) the manufacturer and type of device; and 5) any actions that can be done on each device.

A total number of rooms can be displayed and an icon is provided that enables the user to add a new room to the list. When the user clicks on the add icon, a new room screen will be displayed. The content area lists the rooms in a table with the following columns: 1) a user defined name for the room, the user can modify the name by using inline editing; 2) the floor on which room is located, the user can change the default room by using inline editing; and 3) the actions that can be done on each room, e.g., delete the room. When the user moves the mouse over each room in the table, the room plan is displayed inline.

A user may edit an existing room. The content area thus displays the current room name and floor that the user can edit to change.

Integration with the Calendar

When the user sets a schedule on any of the home automation devices, the schedule will be integrated on a calendar application. For example, if the user has scheduled housekeeping tasks at specified times, then the calendar automatically reflects those tasks. In each user's calendar, only the tasks assigned by that user are reflected. Similarly, if the user has utilized the scene builder to generate a "night scene" that is initiated at 8 p.m. everyday, then the calendar shows the scheduling of the "night scene" everyday at 8 p.m. The user is then able to click on the scheduled tasks and modify the task. When the tasks are displayed on the calendar, the user may click on the task and make any changes on the task. The calendar is updated to reflect the changes. Thus, if the time of the scheduled task was moved from 8 p.m. to 9 p.m., then the calendar automatically refreshes to show the new scheduled time.

Alarms, Logs, Statistics and Diagnostics

Referring to FIG. 4, the support services network 50 also may process alarms, logs, and statistics. For example, alarm aggregator 82 of the alarm subsystem may collect alarm statistics from the gateway appliances, for example, using the signaling control channel, and from other network elements, preprocess, and screen the collected alarms and pass them to the alarm subsystem for appropriate processing. Alarm aggregators, for example, may request alarm and diagnostic information from selected gateway appliances at predetermined intervals. Alarms may also be collected on demand, for instance, when a user requests diagnostic information for a selected gateway appliance. Further yet, the gateway appliances may communicate alarms as they occur. The alarm subsystem 82, 85 may log and provide diagnostic access to all the network elements and utilize the underlying accessibility framework for hard to reach gateway appliances. The alarm subsystem 82, 85 further may run diagnostics, configuration control, and provisioning control.

Figure 6G:
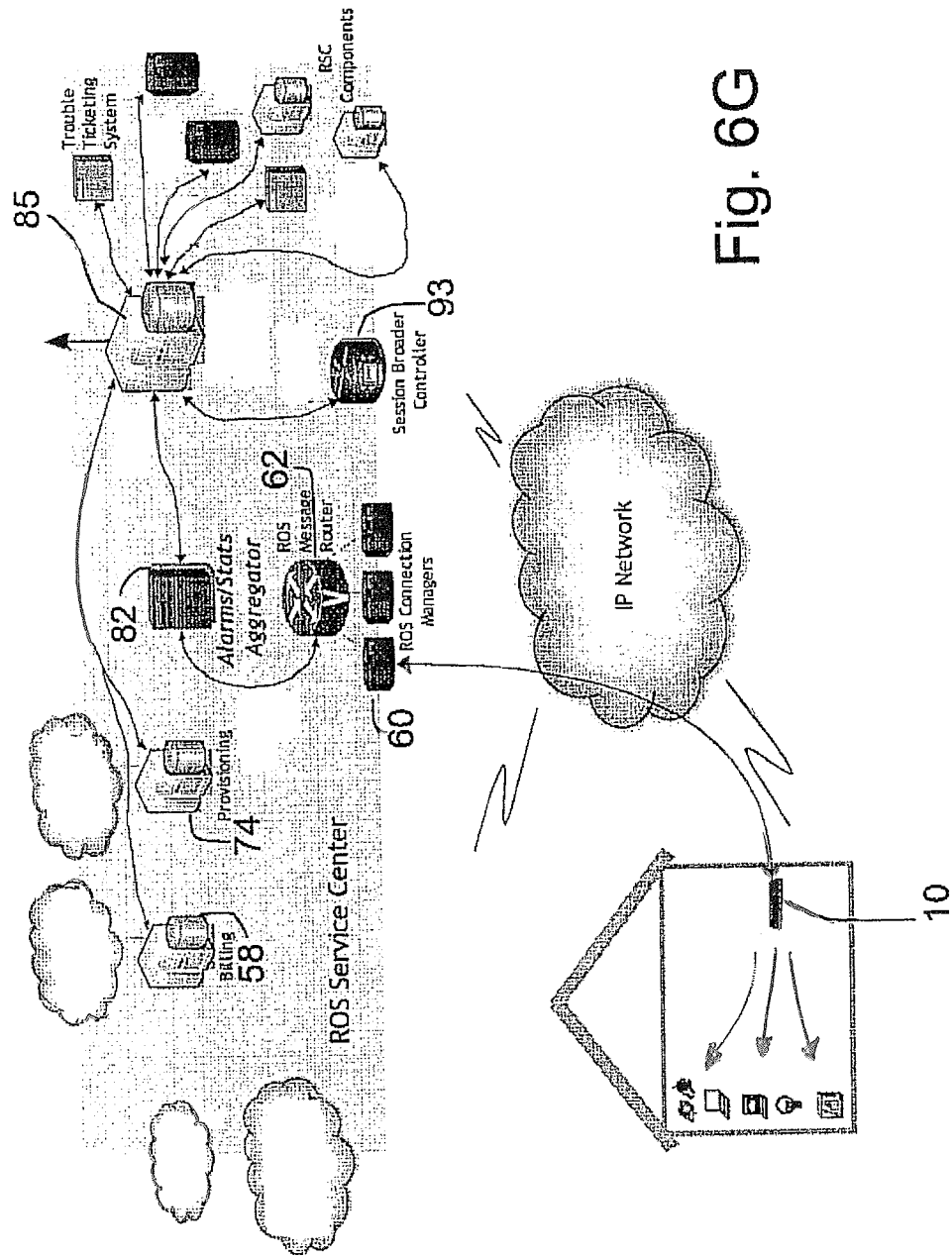
FIG. 6G illustrates an architectural overview of alarms and statistics aggregator functionality in the support network in one embodiment.

FIG. 6G illustrates an architectural overview of alarms and statistics aggregator functionality in the support network in one embodiment. In an exemplary embodiment, the alarms and statistics aggregator functionality 82 provides a method for monitoring and troubleshooting the gateway appliances. The aggregator functionality 82 in general may provide a collection point for all alerts and statistical data from the gateway appliances. These alerts and statistics may be massaged, e.g., filtered or reformatted, and forwarded to a $3^{rd}$ party network management system 85 for monitoring and managing the gateway appliances. In another aspect, the aggregator functionality 82 may serve as a conduit for querying information from each gateway appliance 10. Information requests may be performed through simple networking management protocol (SNMP) that gets initiated by the network management system 85. Alarms from the gateway appliance 10 may travel through the connection manager or like functionality 60, message router or like functionality 62 to the aggregator(s) 82 or like functionality to reach the NMS 85. In one embodiment, the aggregator(s) 82 receive alarms, logs, and statistics in the format of XMPP messages. The following depicts an example alarm message structure generated by the gateway appliance for communication to the service center. The alarm message shows a SNMP Trap encapsulated in XMPP.

```
<stream:stream
    xmlns='jabber:client'
    id='c2s_345'
    from='gateway appliance-unique-number@prodeasystems.com'
    to='alarms@prodeasystems.com'
    version='1.0'>
<SNMP Trap> Version number = SNMPv2
    Community name = gateway appliance-Network
    PDU type        = Trap
    Request ID      = 1
    Error status    = 0
    Error index     = 0
    Variable bindings = {Alarm = rhcCallRoutingFailure
        Subsystem = gateway appliance-Voice
        Region = 75080}
</SNMP Trap>
```

In one example embodiment, the SNMP Trap is formatted in XML or like mark-up language. In operation, the aggregator 82 translates messages from the gateway appliance to a SNMPv2c format and then forwards the messages to the NMS 85. Aggregators 82 may also translate SNMP gets queries from the NMS 85 to XMPP messages for sending to the gateway appliances. Regardless of the direction of communication, the aggregators 82 translate the message to the appropriate protocol. Other network elements may utilize the aggregator 82 for alerts and statistical requests. In one embodiment, alarms from any network elements of the support network may travel directly to the NMS 85 without passing through the aggregator 82.

In one embodiment, a mechanism for load balancing and redundancy may be provided for the alarms and statistics aggregators 82. One mechanism may include performing load balancing across the aggregators 82 through a separate application or functionality referred to as alarm component. Alarm components may manage connectivity between the message routers 62 and the aggregators 82 as well as evenly distribute incoming messages across all aggregators 82. The aggregators and components may run in N+1 configuration, which may permit an aggregator or component to be unavailable without affecting the collection of alarms and statistics. In addition, there may be aggregators dedicated to translating and passing SNMP gets for querying information from the gateway appliances. These aggregators may communicate directly with the alarm components to forward the XMPP translation of a SNMP get to a message router 62, which forwards the XMPP message to the gateway appliances. In one embodiment, the majority of aggregators may be dedicated to routing messages to the NMS 85, while a fewer such as one or two aggregators may handle routing messages to the gateway appliances.

In another embodiment, connectivity to the message router functionality 62 may be integrated directly into the aggregator 82. In this embodiment, the routing of messages from the gateway appliance 10 to an aggregator 82 may be based on the following: each gateway appliance may establish a static connection to a message router 62. Each connection manager 60 may have a static connection to a message router 62. Each aggregator 82 may establish static connections to multiple message routers 62, for instance, with no router having more than one aggregator connection. Messages from an appliance 10 may then flow through a common path to the same aggregator. If an aggregator is unavailable, then messages for that aggregator may route to the closest available aggregator through the message routers 62.

Aggregators or like functionality 82 may themselves generate an alarm, for instance, upon failure of the aggregator to translate a message to SNMP. Similarly, an alarm may be generated upon failure of the aggregator to translate a message to XMPP and forward the message to a gateway appliance. The alarms and statistics aggregator 82 or like functionality may also generate alarms, for instance, upon establishing successful connection to a message router, failed connection, when an active connection is lost, or upon failure to forward a message to a gateway device. Such alarms may include the IP address or the FQDN of a message router and reason or description for the event.

In one embodiment, each NMS may be associated with a service provider. For enabling aggregators or like functionality 82 to route messages received from the gateway appliances to a specific service provider NMS 85, the alarm message may include an identifier for the service provider or the aggregator 82 may query the service provider, for instance, from an external source, based on the gateway appliance's ID such as Jabber ID. In addition, the aggregator 82 may track a list of IP addresses and ports for each NMS 85. Further, the aggregator 82 may support the option to route messages to one or more NMS 85 based on the service provider associated with the gateway appliance sending the message.

In one embodiment, the alarms and statistic aggregator or like functionality 82 may support different states when active. One state may be unlocked. During unlocked state, the aggregator receives incoming messages and translates messages. Another state is locked. In locked state, the aggregator is no longer accepting incoming messages, however, the application, i.e., aggregator may be still translating messages. This state may be useful for gracefully halting or shutting down an aggregator. Generally, an administrator may be given privileges to be able to move an aggregator instance into a locked state or unlocked state. In addition, an administrator may be enabled to shut down an aggregator instance. Further, the aggregator cluster 82 may be designed such that a single aggregator instance may be upgraded or shutdown without affecting or having to shutdown or stop all aggregator instances.

In another embodiment, the alarms and statistics aggregator or like functionality 82 may be monitored. A monitoring agent may oversee the various aggregator processes and watch over the state of its servers or like functionality, for example, to ensure the aggregator service remains available. The monitoring agent may perform appropriate notifications to appropriate components or functionality if any problems are detected during monitoring process. In another aspect, there may be monitoring agents for other elements or functionalities in the support network.

In one embodiment, the alarms and statistics aggregator or like functionality 82 may maintain various counters and statistics relating to the number of messages and events occurring within each aggregator instance. For example, each aggregator instance may track a list of gateway appliances from which it has received incoming messages and/or the number of incoming messages it receives from a gateway appliance; track the number of messages discarded due to its inability to translate a message from XMPP to SNMP, or from SNMP to XMPP; and track the total number of messages discarded due to the unavailability of a gateway appliance, etc. This information may be queried from each aggregator instance through the use of a SNMP get and stored in the NMS 85 for near real-time and historical reporting. The report may be available to the network administrator for monitoring traffic levels across the aggregator instances. There may be an option, for example, for an administrator to reset or clear one or more or all counters or information.

Logging is a useful function for troubleshooting events that occur within an application. The alarms and statistics aggregator may include a generic process responsible for logging messages. Logs of processing performed by the aggregators may be recorded and stored. Such processing may include, but not limited to, attempts to connect to message routers, failed connections including IP addresses and port numbers or FQDN of message router, and lost connections, etc. In addition, incoming or outgoing messages in the aggregator may be logged including, for example, messages it failed to forward.

In addition, other network elements, servers or service functionalities may be capable of logging events, statistics, and generating alarms based on various processing performed specific to each server or functionality in the support network. The alarms and statistics aggregator may also interface with those network elements to collect various alarm and statistical data related to processing.

From the gateway appliance perspective, the gateway appliances may have the ability to generate alarms when a pre-configured threshold value is exceeded on the device. A user may have an option to set the method by which the user may be notified when an alarm is generated. In one embodiment, multiple notification events may be defined on the appliance. These notification events may be capable of being associated with different roles so that assigned user can be notified when the event occurs. Examples of different methods of notification may include but not limited to e-mail, a text or SMS message, instant messaging, personal page, TV, and telephone. Every role (types of users) may have the ability to receive notification for any notification event. In one embodiment, the same notification or alarm event may be notified in multiple ways to the same user. Analogously, the same notification or alarm event may be notified in multiple ways to different users.

The generated alarms may be logged and their statistics generated. Similarly, other information may be logged and their statistics generated. Alarms, logs, and statistics kept in the support network may be accessed by a user at the gateway appliance using web services interface in one embodiment. Further, HTML GUI may be provided for the user to access the alarm, logs, and statistical information associated therein. Different levels of logging may be enabled or disabled depending on the access privileges set through configuration. The gateway appliance, in addition, may be enabled to filter logs, alarms, and statistics based on search criteria.

Example functionalities based on which an appliance may generate logs and statistics are defined in Table 1.

TABLE 1

| Sample of System functionality | Condition for logs and statistics to be generated |
| --- | --- |
| monitor the CPU utilization on a continuous basis | if the CPU utilization exceeds preconfigured threshold values the system may create a log |
| Memory monitor the disk utilization on a regular basis | the amount of memory usage if the disk utilization exceeds preconfigured threshold values the system may create a log to capture: preconfigured threshold value current utilization level |
| Keep track of login attempts | if unsuccessful login attempts are noticed the log shall capture: date and time of the login attempt the userid of the login attempt number of attempts made |
| Track firewall probe attempts | Provide firewall process logs If the number of attempts exceeded the maximum allowed value within a preconfigured duration, the events may be logged. |
| Track bandwidth manager status | 1. Log the status 2. Log any throttling actions 3. Log any pre-configurable thresholds |

With respect to alarms generation, the gateway appliance is capable of: 1) displaying alarms on the network map of the user; 2) sending alarm to the service provider; and 3) sending an alarm to the user. Any/all of these methods can be configured against a particular alarm. Example conditions under which alarms are generated are given in Table 2:

TABLE 2

| Name of alarm (examples) | Condition for alarms to be generated | Actions to be taken |
| --- | --- | --- |
| TEMP_ALARM | If the temperature thresholds on the devices that are temperature controlled are exceeded | shutdown the GW device and optionally: send an alarm to the OAMP Server notify the configured user |
| DISKUTIL_ALARM | the disk utilization exceeds critical levels | notify the configured user |
| SYSDOWN_ALARM | when applications or subsystems are down or service faults are detected | send alarms to the support network notify the configured user |
| FIRMUPFAIL_ALARM | failed firmware upgrade | notify the configured user |
| LOGIN_ALARM | If the number of login attempts exceeds the configured maximum value within a preconfigured duration | notify the configured user |

Billing

The gateway appliance in an exemplary embodiment is an interactive device for a premise such as the home that enables users to purchase and activate services. The support network 50 thus further may provide bill collecting capabilities for services rendered at the gateway appliance. Examples of services, for example, may include voice, media such as movies and music, backup services, home automation, file sharing, and parental control, etc. Referring to FIG. 4, billing aggregator or like functionality 58 may communicate with the gateway appliances and the third party service providers (e.g., VOD(s), CA(s), wholesale voice providers, backup services, etc.) to collect and correlate billing records.

In one embodiment, the gateway appliances and other network elements may generate records of billable events, which may be used for billing, verifications, troubleshooting, and other purposes. The gateway appliances, for example, may record all billable events and send the data to the billing aggregator or like functionality 58 using, for example, the signaling control channel, for instance, via the message router. This transmission of billing data may occur at a regular interval or a predefined interval or at other desired time or period.

Thus, from a gateway appliance perspective, an appliance may keep records of usage information and events (referred to as event records) associated with services such as those associated with voice calls, media services, etc. In one embodiment, it may be possible to derive billing data from a single event record without having to correlate with any other event record. The gateway appliance 10 interfaces, e.g., transparently through the routing manager functionality, with billing collector 58 and sends the event records to the billing collector or like functionality 58, which collects event records from all gateway appliance platforms. In one embodiment, the collection may be executed at predefined intervals, for example, as configured on individual gateway appliance 10. In one embodiment, the gateway appliance may be capable of initiating the transfer of the generated event records to the billing collector, e.g., at configurable intervals.

An example protocol used for communicating the event records between the gateway appliances and the billing collector is XMPP, although not limited to such. XMPP is defined in IETF RFCs 3920 and 3921. For example, the process of transferring the records generated by the appliances may be through the XMPP protocol and the application layer protocol attributes. Example attributes of the XMPP protocol may include: the appliance initiating a "message" stanza; the "to" attribute containing the full JID of the billing collector or like functionality; a stream unique "id" assigned to the message; and the body of the message containing the appliance generated event record in a string format. An example application layer protocol may contain data such as a unique message ID which may be different from the message of the XMPP layer, message sequence number (e.g., 1, 2, 3, etc.), and total number of bytes in the event record contained in the body of the XMPP "message."

As mentioned, one or more gateway appliances 10 may communicate billable events via XMPP messages that include billable events to the billing collector or like functionality 58 via a message router or like functionality 62. In one embodiment, the message for the event record transfer from a gateway appliance 10 to the billing collector 58 may be a two-way handshake. Thus, in one embodiment, the billing collector 58 sends an acknowledgment to the appliance for every message received. The appliance may resend the message if it does not receive an acknowledgment, e.g., within a predetermined time. In one embodiment, when the billing collector 58 receives the message from the appliance, it checks the message for errors (e.g., whether the total number of bytes in the enclosed event records is equal to the total number of bytes mentioned in the application layer attributes parameter). If there are no errors, the billing collector 58 writes the data to a file and stores it, e.g., on a storage device.

In one embodiment, the billing collector 58 then sends the acknowledgment to the appliance. The acknowledgment message, for example, may contain the same message ID as the received message, so that for instance the appliance can identify that it is a receipt of the message sent. As mentioned above, in one embodiment, if the gateway appliance does not receive the acknowledgment message within a predetermined wait-time, it may resend the message. Thus, in one embodiment, the billing collector 58 may receive a re-send of the previous message. However, in one embodiment, the billing collector 58 need not know that it is a re-resend. Instead, in one embodiment, the billing collector 58 may treat the message as if it were the first message of its type. If an error occurred in the message, for example, the number of bytes in the received event records does not match the number of bytes in the message attribute, then the billing collector 58 may formulate an error message and send it to the appliance. The message may contain an error reason, for example, "error in bytes received."

Parental Control

Yet another functionality that may be provided in the appliance gateway in conjunction with the support services network includes parental control. The parental control functionality in one embodiment may allow parents to track what their children are doing on their PC's or what content children are watching, for example, on a media device such as the TV or PCs, and provide an easy way for parents to grant permissions for children to watch a show on a remote TV or watch pay per view content. Furthermore, the parental control functionality in one embodiment may allow parents to monitor and control access to media devices such as a telephone providing voice services associated with the gateway appliance.

In one embodiment, software running on the PC as a background service may record all desktop activity as a video and distribute it to the gateway appliance to be stored on a hard drive. The video may be published on the local network using a protocol such as UPnP. Parents can then view the video by connecting to the video stream hosted on the gateway appliance from a TV by using a set top box, which acts as an UPnP renderer. This unique method provides a near real-time view of all PC desktop activity from a remote and convenient location. Parents need not have to go to the child's room to check up on any PC activity. Parents can track their child's PC habits while they are watching TV. If the set top box is capable, the PC view could be shown with picture-in-picture overlaid on the live TV signal.

In another embodiment, video content managed by the gateway appliance as a service may be accessed in the home on TV's using a set top box. The service provides a mechanism for parents to manage the parental controls of the service content. When a child tries to watch a movie, but cannot since it is blocked by parental controls, he may press a button on the remote to send a notification to parents TV to get permission to watch. On the parent's TV, a notification appears. Parent opens the notification on TV, sees data about the movie, and then indicates with the remote if the movie is allowed. If it is allowed, then the movie may be unblocked for the child. If it is not allowed, the movies are still blocked and the child may get a notification on his TV that the parent has not given permission. This way the child does not need to run to the parent and provide explanation of the movie, or the parent need not independently search for information about the movie in order to decide whether to provide permission for viewing.

In yet another embodiment, the gateway appliance may provide a pay per view service. The gateway appliance may provide parents with configurable mechanisms to allow children to ask permission to watch pay per view content. When a child wants to watch a pay per view movie, he presses a button on the remote which then sends a notification to the parents, for example, using TV, SMS or email. The parent receives the notification with all the information about the movie and the cost. The parent can then indicate whether the movie can be watched. The gateway appliance may have a web server to allow the parent to remotely specify permission by hosting a web page, which can be accessed by a browser on a mobile phone or a link embedded in an email. If the parent grants permission, then a notification may be sent to the gateway appliance to allow the payment. A notification may also be sent to the child's TV indicating permission was given. If permission is not given, then a notification may be sent to the child's TV indicating that decision. This mechanism allows parents to give their children permission to watch pay per view content remotely, without being at home. Parents can see the information about the show and can directly control the payment transaction.

In another exemplary embodiment, the gateway appliance may provide parental control functionality with respect to voice services associated with the gateway appliance. For example, the gateway appliance may be associated with a telephone device (i.e. a traditional PSTN telephone through an adapter, a session initiation protocol telephone, IM client) to provide managed voice services. An adult, by utilizing the exemplary service may monitor and manage all voice conversations the service provides. As an example, a parent can press a button on a TV remote, which may display a list of all voice calls that have occurred in the home with a particular telephone device. The gateway appliance may be configured to associate users with particular telephones such that the parent can monitor and manage access to specific voice services available to their children. By way of example, an adult can monitor a particular telephone device usage by observing the time-of-day the call occurred, the day-of-the-week the call occurred, the type of call (i.e. local, long distance, international), the length of the call, the date on which the called occurred, the number called, and the number of the calling party. Furthermore, through the gateway appliance, an adult can manage a child's usage of a telephone device by limiting accessibility of the device according to various parameters that may include, but not limited to, the identity of the user, time of day, day of week, and type of call. Thus, the gateway appliance provides parents a real-time view of the voice services being as well as a method for managing the use of telephone devices within the home.

The gateway appliance may keep track of all content that is being watched on the services it provides. A parent can press a button on a TV remote, which may display a list of all content that is currently being watched in the home. The gateway appliance may be configured to associate users with particular media devices such as TVs such that the parent can see what content their children are watching on their TVs. This provides the parents a real-time view of the kinds of content their children are watching. This mechanism also allows the parents to keep track of how much TV their children are watching.

In operation in one embodiment, functionality in a set top box (STB), for example, may overlay GUI on the live TV signal. The STB may have a universal remote control, which allows the user to control TV/cable/satellite functions in addition to one or more features provided by the system and method of the present invention in one embodiment. By pressing a special button on the remote control, a gateway appliance menu system may be overlaid on the TV signal. A user may then use the navigation buttons on the remote to select one or more gateway appliance features.

The parental control functionality may be established by a parent setting preferences on the gateway appliance through a media device. Specifically, the parent may utilize a media device such as a TV or a PC that is connected to the gateway appliance to establish certain parental control parameters. For example, a parent could limit their child's access to certain media devices based on the various parameters the parent entered into the gateway appliance. Parental control parameters that may be established by a parent include, but not limited to, (i) limiting access to certain media devices for a certain user because of their identity, (ii) establishing a password for a specific media device thereby not allowing an end user to access that device without the password, (iii) limiting access to a specific media device based on the time of day, (iv) limiting access to a specific media device based on the time-of-week restrictions, and (v) utilizing media content ratings thereby restricting an end user from accessing certain media on a media device that is deemed inappropriate for that end user based on the media content ratings. Thus, a parent through a media device associated with the gateway appliance may establish accessibility parameters that enable the parental control functionality within the exemplary system.

In one embodiment, when a child tries to watch a movie that is stored on a gateway appliance, the STB may query the appliance if there are any restrictions on playing the movie. The gateway appliance in one embodiment may keep a database of all of the parental control settings. The gateway appliance may use this data to decide if the movie can be played, for example, based on the ratings metadata of the movie. If the movie is locked by parental controls, the gateway appliance may inform the STB to display a list of options on the TV. The list of options may be overlaid on the TV signal by the STB. One of the options may be to ask the child's parent(s) or like for permission to watch the movie. When the child selects that option, a message is sent to the gateway appliance. The gateway appliance may have a notification mechanism, which allows notifications to be sent to any device it manages. When the gateway appliance receives the request for parental controls permissions message, it may use its knowledge of how to contact the parent(s) or like and which device to send the notification. All users of gateway appliance can use an interface such as a Web GUI to configure how they should be notified and for which notifications which devices should be used. This notification configuration data may be stored on the gateway appliance, for example, in its database. If the parent(s) or like are watching TV in their own room, then the gateway appliance may send the notification and the metadata about the movie to the STB for that TV. The STB may overlay the message and movie data on their TV signal. The parent(s) or like may be able to read the message and then select from a list of options how to respond to the child's request. When the parent has made a selection using their remote control, that STB may send that response back to the gateway appliance. The gateway appliance may send that response as a notification to the child's TV using its STB. If the response was to allow the movie to be watched, the RHC may remove the lock on the movie, and it may allow the movie to be streamed to the child's STB. If the response was not to allow the movie to be watched, the child may not be able to play the movie and may be given the option to pick another movie.

Voice Services

Voice services support is another capability provided by the gateway appliance and networked services support infrastructure of the present invention. Subscribers have at their disposal a rich set of voice services including, but not limited to: anonymous call rejection; call forwarding (unconditional, call forwarding on busy, call forwarding on not available); call hold; call logs; call pickup; call transfer, call waiting; call waiting with caller ID; caller ID delivery; caller ID/caller name blocking; caller name delivery; contacts/address book management; do not disturb; emergency call handling; fax support; international dialing support; message waiting indication for voicemail; national dialing support; selective inbound call restrictions; speed dial; three-way conference calling; and voicemail.

Where applicable, subscribers may configure features and services via a web interface or using Vertical Service Codes (VSC). Call history for calls received, calls originated, and calls missed may be provided in the subscriber's personalized call portal. Complete voice package to customers may be offered as extensive voice network architecture.

In one embodiment, the subscription manager or like functionality provides the subscription information as well as configuration data information for voice provisioning details to the gateway appliance. For instance, the subscription manager or like functionality may receive metadata regarding provisioning, e.g., information associated with configuration data needed to provide the service from the voice service manager or like functionality. In another embodiment, the gateway appliance may request the configuration data information from the voice service manager or like functionality. The gateway appliance may then download the needed configuration data described in the metadata from, for example, the voice service manager or like functionality. The actual downloading may occur at a later time or at the time the voice service is being provisioned. Exemplary voice services that may be provisioned at a gateway appliance include dial plan configuration and inbound/outbound routing configuration supported auto configuration device list.

Figure 7:
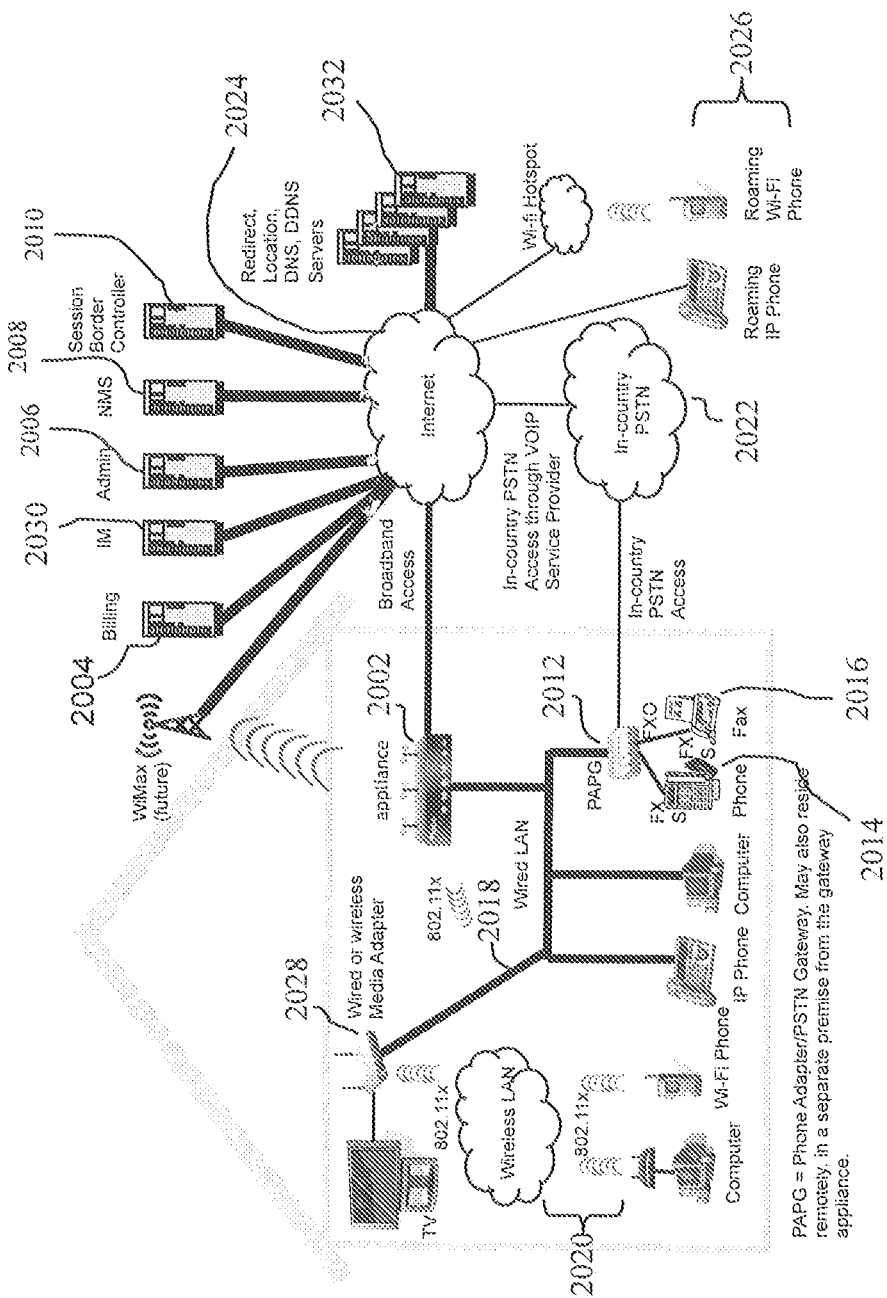
FIG. 7 illustrates an example architectural diagram for providing call (e.g., voice or other media) processing in one embodiment.

FIG. 7 illustrates an example architectural diagram for providing call (e.g., voice or other media) processing in one embodiment. In-premise or in-home components may include gateway appliance 2002 of the present disclosure, SIP and FXS endpoints, possible in-home gateways, and software clients. Support network components or like functionality may include billing 2004, provisioning, network management 2008, and session border controllers 2010. Examples of end user functionality may include, but is not limited to, voice services to home owners globally in multiple countries; instant messaging contact list downloads with presence functionality; office or email application contact lists downloads; ability to make calls from IM clients to VOIP or PSTN terminations; ability to make calls from IP Phones to IM clients, VOIP or PSTN terminations; ability to make calls using "click-to-call" from web browser; ability to make video calls; ability to make calls from traditional phones (through a Phone Adapter) to IM clients, VOIP or PSTN terminations; ability for user to manage services from TV; if the home owner has subscribed to a PSTN line, PSTN routing can be used as an overflow option or as the primary choice, based on station; whole house voice mail services; ability to make intercom calls based on public numbers or speed dial numbers; ability for the user to manage gateway appliance contact lists, and other service attributes; voice services integrated with other services on the same platform; ability to use interactive voice prompts to manage services; and ability for one user to have multiple gateway appliance devices geographically scattered. Such a gateway appliance sub network may have common billing and allow the user to move endpoints between gateway appliances.

From the support network or management perspective, call services may be managed and provisioned centrally and remotely (e.g., using web browsers or other interfaces), billing information and statistics records may be collected from the gateway appliances.

In one embodiment, if a user has subscribed to a PSTN line, PSTN access may also be provided. For example, a phone adapter/PSTN gateway 2012 may be used to provide access to PSTN and an interface for traditional PSTN phones. Optionally, PSTN access may be provided through a break-out from the internet at a later point in the network.

Shown in FIG. 7, the appliance 2002 resides in-home, connecting to various end-user devices. The devices may be traditional phones 2014 and faxes 2016 (e.g., through a phone adapter/PSTN gateway 2012), IP devices 2018 connected over wired LAN or IP devices 2020 connected wirelessly. Appliance 2002 may also support connections to the in-country PSTN 2022 (e.g., through a phone adapter/PSTN gateway or through break-out from a VOIP service providers network) to the Internet via broadband access 2024 (e.g., via 802.11x WiFi, WiMax).

In one embodiment, the functionality between RHC and PAPG remain country-independent as much as possible. A user may be able to manage service aspects utilizing a TV display and remote control, for example, using a media adapter (UPnP AV or other). A media adapter may be able to handle context-specific (e.g., in relation to what is displayed on the TV) input from a remote control and communicate this to the appliance 2002. This interface may be used for a user to select menu-driven items.

In one embodiment, services may be provided between in-home devices (e.g., 2012 . . . 2018) and remote devices (e.g., 2022 . . . 2026). In-home devices may include, but are not limited to: SIP endpoints (e.g., a SIP phone connected over ethernet or over 802.11x or a computer connected over ethernet or over 802.11x, or other means); IM endpoints (e.g., devices capable of IM signaling over ethernet or 802.11x or other means such as computers and wireless phones); traditional FXS phones and Fax machines, for example, connected via a phone adapter/PSTN gateway or like devices, for example, making them appear like SIP endpoints to gateway appliance 2002. Remote devices may include devices located outside the home, worldwide. The actual end devices may be of multiple types and is not required that they are visible to RHC. For instance, they may interact via SIP on a broadband interface or through the phone adapter/PSTN gateway or like device or functionality. Remote devices may include, but are not limited to: SIP phones (wireless or wireline) associated with a gateway appliance; external IP Phones (both gateway appliance-based and non-gateway appliance based); PSTN phones; and IM clients.

In one embodiment, the gateway appliance 2002 may serve as an in-premise server responsible for call processing. PAPG 2012 may connect traditional FXS phone/faxes or like, the PSTN, and gateway appliance platform. Media adaptor 2028 may be used to allow a user control of services such as voicemail from such devices as TV. Further, there may be provided media services for conferencing. IM 2030 may provide instant messaging services to users with IM-capable platform and handle contact lists and associated management. Provisioning 2006 in general provides provisioning services and gateway appliances and users. NMS 2008 may manage and process alarms and other information from the gateway appliance 2002, for example, received via aggregator functionality in the support network. Billing 2004, for instance, collects billing information or billable events and records from the gateway appliance 2002. SBC 2010 in general serves as an interface to a VOIP service provider or like. This functionality 2010 may also provide security functions. SIP directory/redirect server (shown at 2032) may provide routing and dynamic DNS (DDNS) server (also shown at 2032) may enable gateway appliance behind NAT, for instance, by correlating gateway appliance FQDN to IP address. SIP location server (also shown at 2032) may provide location mapping functionalities.

Interfaces at the premise interfacing to the gateway appliance 2002 may include wired local area network supporting, for example, including 10/100 ethernet, multimedia (MOCA), and homePNA. The appliance 2002 may also support wireless interfaces such as 802.a, 802.b, and 802.g network, etc. In addition, external interfaces such as traditional PSTN line interface between PAPG and CO, Cable, DSL or Fiber-based interface to ISP, and wireless broadband (Wimax or any other standard) interface may also be supported.

Example services, which may be supported by functionalities in the gateway appliance 2002 may include, but are not limited to: calls from one home endpoint to another in-home endpoint (e.g., intercom calls); calls from a FXS phone behind a PAPG to the PSTN, VOIP network, or an IM endpoint; calls from a wireline or wireless SIP phone to the PSTN, VOIP network, or an external IM endpoint; calls from an IM client on a computer to the PSTN, VOIP network, or another external IM endpoint; a SIP phone may be registered in-home or externally from a remote location (such a location may be a wireline network or wireless (e.g., WIFI) hotspot; and origination using a click-to-call mechanism, where the termination may be selected from a contact list using a browser from a computer or phone or like. The origination may be another registered device.

The SBC may hide the details of the networked support services infrastructure from the wholesale provider for inbound calls and hide the details of the wholesale providers' VoIP network from the networked SC. On calls inbound from the wholesale provider, the SBC sends a SIP invite to the SIP redirect server and subsequently extends the call based on a redirect (3XX) message received from the SIP directory server. On call requests received from the appliances, the SBC sends a SIP invite to the SIP directory server and subsequently extends the call based upon a redirect (3XX) message received from the SIP directory server. Media may or may not be anchored to the SBC, depending on network optimization requirements. The SBC also may record billing records and events for all SIP calls and send these records to the billing collector or system.

Public SIP redirection and proxy servers or like functionality in one embodiment may provide SIP proxy/redirect services to public remote SIP phones and devices. The public SIP proxy/redirect servers provide a similar function for SIP requests as the public web servers for HTTP requests, described above. The users of these servers may be remote based WiFi or IP SP phones that need to register with the "home" gateway appliance or place a call, which routes through the gateway appliance. The request is resolved by the DNS and directed to the public SIP server, the public SIP server queries the location server and then, depending on the type of request and the accessibility of the gateway appliance, the public SIP server may either proxy or redirects the request. In one embodiment, all remote phone registration requests to gateway appliance may be proxied by the public SIP server. These servers or like functionalities may have interfaces to the location server, the SBC, the VPN router/server or like functionalities and the gateway appliances.

Off-Premise Voice Extension

An embodiment of the present invention allows an off-premise phone to register with a gateway appliance as an extension to the phone service provided via the gateway appliance. In this embodiment, a gateway appliance or device may serve as an IP-based residential Private Branch Exchange (PBX). This PBX may serve as a switchboard to route calls among extensions as well as off-premise extensions, for example, for a phone such as an IP-based WiFi phone, which accesses the public internet through WiFi connection, or a computer-based soft client which communicates in voice over IP technology and runs on a computer. One or more functionalities at the support network 50 relay the registration message, the call setup message as well as voice stream between the home PBX and the off-premise user.

As an example, with reference to FIG. 4, when a phone is powered on, it first connects with an available WiFi network, and then finds the support network 50, for example, a session border controller (SBC) 93 or like functionality and sends out the registration message. For example, the call from the phone may be addressed to a particular domain, which may be resolved by DNS and directed to SBC 93. Similarly, a user may start a soft client (soft phone) and key in user name, password, and the identification of the home PBX.

The soft client sends the registration to the support network 50 and the support network 50 determines where the corresponding home PBX is and forwards the registration message. The home PBX records the location information of the phone. All consequent calls can be established between the phone and the called party through the support network 50 and home PBX. The voice stream is established after the signaling messages are exchanged.

In one embodiment, SIP server (SRS) or like functionality 92 may provide session routing, re-direction, and authentication on a session basis. Routing to gateway appliances 10 may be based on information (e.g., appliance address, etc.), which for example, may be contained in a database, for example, updated by provisioning servers and location servers 68 or like functionality. The information may be updated on a real-time or near real-time basis. Thus, for example, location server or like functionality 68 may provide dynamic location data such as IP addresses and port numbers of gateway appliances and presence (e.g., voice service availability) indicator of a gateway appliance. SRS 92 in addition may have capabilities to log events and generate alarms based on various processing it performs.

The Session Border Controller (SBC) or like functionality 93 may provide a secure network border control, for example, for voice and video services. The SBC 93 may act as a back-to-back user agent and may provide varying degrees of topology hiding, call routing, and access screening, etc. In one embodiment, the SBC may be relied on to provide the routing towards the various wholesale providers based on the destination address returned by the SRS or like functionality 92. In one embodiment, the information in the SRS 92 may originate from provisioning functionality (subscriber data) and/or operational data (provisioned on the SRS). In one embodiment, SIP interface is utilized between the SRS 92 and SBC 93. A SBC may request call routing from the SRS 92. The SRS determines the appropriate routing of the call and returns a response indicating how the SBC should handle the call.

In one embodiment, the SRS 92 is capable of receiving register messages from SBC, locating a gateway appliance information for voice service using gateway appliance ID. If the appliance information is found, the SRS 92 returns the IP address and port number. If the SRS does not find the appliance, the SRS 92 may return a not found message to the SBC. The SRS 92 is also capable of receiving invites from the SBCs 93, from the appliances 10. The SRS 92 may map the user part of the To address to the destination address key, verify that the domain portion of the destination address is correct. The SRS 92 also may determine whether the type of a call, e.g., "support network origination", "off-premise extension origination", "non-support network origination", for example, by receiving the invites over separate IP/port address combinations.

If the call is a "support network origination" call, the SRS 92 may authenticate the originating party. The SRS 92 may use the destination address key to identify if the number belongs to a gateway appliance or is an outbound call, and try to find the destination IP address and optionally port number. If the SRS 92 finds that the address entry exists in the database or like and that the gateway appliance and the voice service on that gateway appliance is available, it returns the address. If the SRS 92 finds that the address entry does not exist, it may assume that the call is for outbound. In this case, SRS 92 may return the original To address as the contact address. This way, the SBC 93 may determine routing to the appropriate wholesale provider based on the target address in the contact header. The SRS 92 may return a logical identifier in the contact header to identify the logical routing to the SBC 93. For example, a header may be "informationprovider@wholesaler1.com"

For a "non-support network origination" call, similarly processing described above for a "support network origination" call may be performed except, for example, the origination party is not authenticated.

If the call is an "off-premise extension origination", the SRS 92 may map the domain portion of the From address to the destination gateway appliance key and queries database to find the matching gateway appliance record. If it finds a matching record, the SRS 92 returns the IP address and port for the gateway appliance. If the SRS 92 does not find the gateway appliance, it returns a not found response to the SBC 93.

Location server or like functionality 68 in one embodiment, generally is responsible for updating support network databases which, for example, may require real-time accessibility information. For instance, although not required, as discussed above, a SRS 92 may comprise a database or like which it queries for location information. A location server or like functionality 68 in one embodiment interfaces with this database (e.g., via database supported interface) to update or load dynamic location data. In addition, the location server or like functionality 68 interfaces with a gateway appliance, for example, using XMPP control channel. This interface may be used when a gateway appliance updates its information during initialization or when its contact data changes. Thus, some example functionalities at the location server 68 may include, but is not limited to the following: location server 68 may receive IP address and port combination from the gateway appliances as they complete initialization or as they change IP address; access challenged gateway appliances may send the VPN accessible IP address and port; the location server 68 may set the availability indicator to "available" when it receives an IP address/port update from a gateway appliance; the location server 68 may be capable of receiving availability updates from XMPP framework; and in addition, the location server 68 may receive service indicator from a gateway appliance that tells which service the IP address and port applies. Like other network elements of the support network 50, the location server or like functionality 68 may be capable of logging events and statistics and generating alarms based on its various processing.

Utilizing an off-premise extension facility in one embodiment disclosed herein, an off-premise phone user, thus, may initiate/receive external calls as if the user was still home. For example, an out-of-state college student can dial hometown buddies with this off-premise extension phone and vice versa. An off-premise extension soft client user can call friends and families from overseas using internet access. Further, calls from the off-premise extension phone can be consolidated with the rest of the home extensions and can be reviewed at any time, for example, for billing and parental control. In one embodiment, the existence of the support network 50 ensures the constant connectivity between the home PBX and the off-premise extension phone.

Billing Requirements VoIP

As mentioned, the gateway appliance is an interactive home device that enables the home user to purchase and activate services offered by the service provider. Some of these services are premium services such as movies and music whereas others are non-premium services such as home automation and file sharing. For the VOIP service in particular, call records are generated by the gateway appliance that are maintained, not only for billing purposes, but alternately utilized for other purposes such as diagnostics, performance studies, statistics, and billing adjustments, etc. The billing collector is responsible for collecting the call records from the gateway appliance and transferring them to the backend billing system.

A billing interface is provided between the gateway appliance and the billing collector element of the service center. Particularly, records are generated at the gateway appliance and are transferred to the billing collector via XMPP protocol transfer using XML file structure.

Accounting Framework for the Gateway Appliance

In one example related to voice services, the gateway appliance captures usage information associated with the VoIP events generated during the voice call. Although the SBC generated records are utilized for billing the call, if necessary, the gateway appliance generated event records may be utilized for billing the call. The event records are self contained in that no correlation of the event records is required for billing purposes.

Generally, associated with the accounting functionality programmed for the gateway appliance, before the event records generated by the gateway appliance are transferred to the billing collector the following occurs: gateway appliance is initialized; and the billing collector has established a session with the routing manager. The gateway appliance may initiate the transfer of the generated event records to the billing collector at configurable intervals.

The gateway appliance utilizes the XMPP protocol as defined in IETF RFCs 3920 and 3921 for transferring the files to the billing collector. Hence, the process of transferring the records generated by the gateway appliance shall be defined through the XMPP protocol and the application layer protocol attributes. The following define the attributes of the XMPP protocol:
1) the gateway appliance shall initiate a "message" stanza;
2) the "to" attribute includes the full JID of the billing collector; 3) a stream unique "ID" shall be assigned to the message; and 4) the body of the message includes the gateway appliance generated event record in a string format. The application layer protocol includes the following data: 1) a unique message ID which is different from the message ID of the XMPP layer; 2) a message sequence number (1, 2, 3, etc.); and 3) total number of bytes in the event record contained in the body of the XMPP "message".

As mentioned, with respect to the gateway appliance-billing collector record transfer process, the message for the event record transfer from the gateway appliance to the billing collector is a two way handshake message. The billing collector sends an acknowledgment to the gateway appliance for every message received. If an acknowledgment is not received, then the gateway appliance resends the message. The role of the gateway appliance in the gateway appliance-collector record transfer process is defined as followed.

The gateway appliance formulates a XMPP protocol and application layer protocol as per the attributes defined hereinabove and starts a timer in the application layer when the message is sent out to the billing collector. For the first message of its type, the value of the timer is equal to a pre-configured value. When the value of the timer has exceeded its pre-set value (e.g., an acknowledgement has not been received from the billing collector), then the gateway appliance shall resend the message. This message shall contain the same value for all the XMPP and application layer attributes defined above, except for the following application layer attributes: a) the message sequence number shall be incremented by 1; and 2) the gateway appliance shall restart the wait-timer in the application layer with the value of the timer incremented to e.g., previous value+5. After the message is sent to the collector, the gateway appliance waits for the acknowledgment from the billing collector. If an acknowledgment has not been received by the time the wait-timer has exceeded the set value, then the gateway appliance shall repeat steps 4 and 5 each time incrementing the message sequence number by one and the wait-timer by 5 seconds. If after the $5^{th}$ attempt (i.e., message sequence number=5) the gateway appliance does not receive an acknowledgement, then the gateway appliance will stop sending the message and generate a critical alarm. If the gateway appliance receives an error response form the collector with a reason value of "Error in Bytes received", then the gateway appliance shall resend the message to the collector. The message shall contain the same message ID (in the application layer) as the previous message, but the message sequence number shall be incremented by 1. The value of the wait-timer shall be set to the same value as the previous message for which the error response was received.

The event records generated by the gateway appliance for the VOIP service are now described. These records are generated in response to significant events detected by the gateway appliance during a call. These events are: 1) start; 2) stop; and 3) inter.

The format of the records is mostly based on the Internet Protocol Detail Record (IPDR) standards. The following table specifies the fields that are generated by the gateway appliance. The fields contain a subset of the IPDR and the fields given in italics are proprietary fields.

Figure 1C:
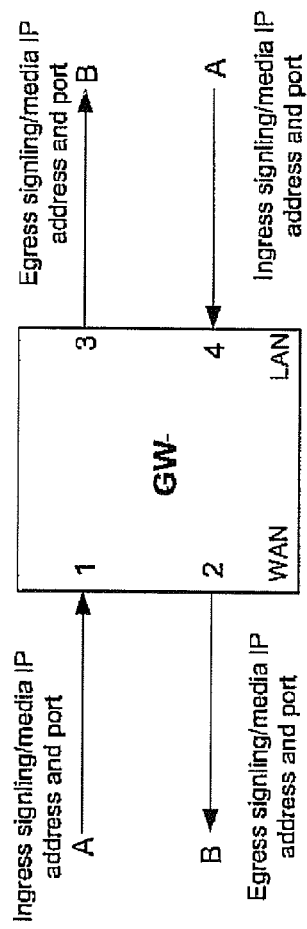
FIG. 1C illustrates the Ingress/Egress Interfaces on the gateway appliance according to one embodiment.

FIG. 1C depicts the concept of the ingress and egress with respect to the gateway appliance and this concept is used to capture values in the fields described on the gateway appliance CDR. The components, servers, services, etc., described in the present disclosure illustrate logical functionalities and they are not meant to be limiting in any way. Rather, they may be implemented as one or more applications, devices or the like, depending on design and implementation choice. In addition, the various functionalities may be implemented on a distributed or central platform.

| | Attribute | Data type | Possible values | Description |
|---|---|---|---|---|
| 1 | CDR sequence number | | | |
| 2 | Hostname | | | gateway appliance JID |
| 3 | IpAddress | | | gateway appliance IP address |
| 4 | gateway appliance firmware version | | | |
| 5 | ingressAccessStartTime | dateTime (GMT) | 2006-11-3-T22:50:00.000Z | When the first INVITE is received from the calling party |
| 6 | ingressStartTime | dateTime (GMT) | 2006-11-3-T22:50:00.000Z | When ACK is received for 200OK |
| 7 | ingressAccessEndTime | dateTime (GMT) | 2006-11-3-T22:50:00.000Z | When the first BYE is received/sent |

-continued

| | Attribute | Data type | Possible values | Description |
|---|---|---|---|---|
| 8 | ingressEndTime | dateTime (GMT) | 2006-11-3-T22:50:00.000Z | the same as above |
| 9 | egressAccessStartTime | dateTime (GMT) | 2006-11-3-T22:50:00.000Z | When the first INVITE is received |
| 10 | egressStartTime | dateTime (GMT) | 2006-11-3-T22:50:00.000Z | When the ingress call is answered with 2000K |
| 11 | egressAccessEndTime | dateTime (GMT) | 2006-11-3-T22:50:00.000Z | When the first BYE is received/sent |
| 12 | egressEndTime | dateTime (GMT) | 2006-11-3-T22:50:00.000Z | the same as above |
| 13 | ingressCallDuration | Integer (ms) | 18000 | Value in milliseconds from ingressStartTime to ingressEndTime |
| 14 | egressCallDuration | Integer (ms) | 18000 | Value in milliseconds from egressStartTime to egressEndTime |
| 15 | timeZoneOffset | Integer | −300 | Time offset, in minutes, of local time zone referenced to GMT. Local time zone should reflect calling party time zone for correct billing |
| 16 | ingressCallID | String | | Unique call ID of ingress call |
| 17 | egressCallID | String | | Unique call ID of egress call |
| 18 | ingressANI | String | 5000@alice.ros.com | Calling Party ID of the ingress call |
| 19 | IngressSubscriberID | | | Extension number of the gateway appliance endpoint (if A -> B, in an inbound call, this will be empty; in an outbound call, this will be the ext of A) |
| 20 | egressANI | String | 5000@alex.ros.com | Calling Party ID of the egress call (if A -> B, in an inbound call, this will be the ext of B; in an outbound call, this will be the DN of B) |
| 21 | EgressSubscriberID | | | Extension number of the gateway appliance endpoint (if A -> B, in an inbound call, this will be the ext of A) in an outbound call, this will be empty) |
| 22 | ingressOriginalDestinationID | String | 5000@alice.ros.com | Original Destination ID of the ingress call (If A -> B CF C, then this field shall contain B which is the originally dialed number) |
| 23 | ingressDestinationID | String | 5000@alice.ros.com | Destination ID of the ingress call (If A -> B CF C, then for an inbound call where B is a gateway appliance SIP endpoint then this field shall contain C; for an outbound call where A is the gateway appliance SIP endpoint then this field shall contain B) |
| 24 | egressOriginalDestinationID | String | 5000@alice.ros.com | Original Destination ID of the egress call; (If A -> B CF C, then for an inbound call where B is a gateway appliance SIP endpoint then this field shall contain B; for an outbound call where A is the gateway appliance SIP endpoint then this field shall contain B) |
| 25 | egressDestinationID | String | 5000@alice.ros.com | Destination ID of the egress call (If A -> B CF C, then for an inbound call where B is a gateway appliance SIP endpoint then this field shall contain C; for an outbound call where A is the gateway appliance SIP endpoint then this field shall contain B) |
| 26 | DNIS | | | Dialed Number Identification Service for 2-stage dialing. |
| 27 | PIN | | | Personal Identification Number |

| Attribute | Data type | Possible values | Description |
|---|---|---|---|
| 28 Ingress signal type | | | Either WAN or LAN (FIG. 1C) |
| 29 Egress signal type | | | Either WAN or LAN (FIG. 1C) |
| 30 gateway applianceingressSignaladdress (Note2) | | | gateway appliance ingress signaling IP address (FIG. 1D) |
| 31 gateway applianceingressSignalPort (Note2) | | | gateway appliance ingress signaling IP port (FIG. 1D) |
| 32 gateway applianceegressSignaladdress (Note2) | | | gateway appliance egress signaling IP address (FIG. 1D) |
| 33 gateway applianceegressSignalPort(Note2) | | | gateway appliance egress signaling IP port (FIG. 1D) |
| 34 gateway applianceingressMediaaddres(Note2) | | | gateway appliance ingress media IP address (FIG. 1D) |
| 35 gateway applianceingressMediaPort(Note2) | | | gateway appliance ingress media IP port (FIG. 1D) |
| 36 gateway applianceegressMediaaddress(Note2) | | | gateway appliance egress media IP address (FIG. 1D) |
| 37 gateway applianceegressMediaPort(Note2) | | | gateway appliance egress media IP port (FIG. 1D) |
| 38 silenceCompressionMode | | | On/OFF |
| 39 thirdPartyID | String | Bob.ros.com | Third party ID if PaymentType value is charged to $3^{rd}$ party |
| 40 callType | String | A (Administrative) I (IVR) N (no answer) V (voice) D (data) F (fax) | Type of Call |
| 41 paymentType | String | Toll-free, charge_to_calling_party charge_to_called_party charge_to_$3^{rd}$_party | Indication of which party pays |
| 42 callProgressState | State to which the call progressed | | |
| 43 callCompletionCode | String | CC: Call completed normally CAD: Abnormal disconnect UCN: unconnected network failure UCI: unconnected invalid address CIP: Call in Progress | Final call completion code for billing use. CIP indicates event-driven IPDR, which is generated ruing call/connection progress. |
| 44 DisconnectReason | String | NormalCall Clearing noAnswer busy failure | Reason that call was disconnected based on Call Completion Code |
| 45 extendedReasonCode | | | Further disconnect information |
| 46 Disconnect initiator | | | Indicates if Bye was sent or received by the gateway appliance |
| 47 proprietaryError | | | gateway appliance-specific use. |
| 48 ingressFeature | String | R(Roaming) L(Line) E(Extension) | Indicates what type of feature (For an inbound call A -> B where A is roaming and B is extension, then this field shall contain R) |
| 49 egressFeature | String | R(Roaming) L(Line) E(Extension) | Indicates what type of feature (For an outbound call A -> B where B is roaming, then this field shall contain R; if A is roaming and B is a DN, then this field shall contain L) |
| 50 ingressCodec | String | G711Alaw, G711ulaw, | CODEC being used |

-continued

| | Attribute | Data type | Possible values | Description |
|---|---|---|---|---|
| 51 | egressCodec | String | G726, G729, G729a, G.729e, iLBC G711Alaw, G711ulaw, G726, G729, G729a, G.729e, iLBC | CODEC being used |
| 52 | supplementaryService | String | Call forwarding, call transfer | Name of supplementary service used in this call |
| 53 | ingressInboundPacketCount | Integer | | Number of packets received on ingress |
| 54 | ingressOutboundPacketCount | Integer | | Number of packets sent on egress |
| 55 | egressInboundPacketCount | Integer | | Number of packets received on ingress |
| 56 | egressOutboundPacketCount | Integer | | Number of packets sent on egress |
| 57 | ipAddressIngressDevice | String | 66.226.243.247 | SBC's address for incoming line call |
| 58 | ipAddressEgressDevice | String | 66.226.243.247 | SBC's address for outgoing line call |

Figure 1D:
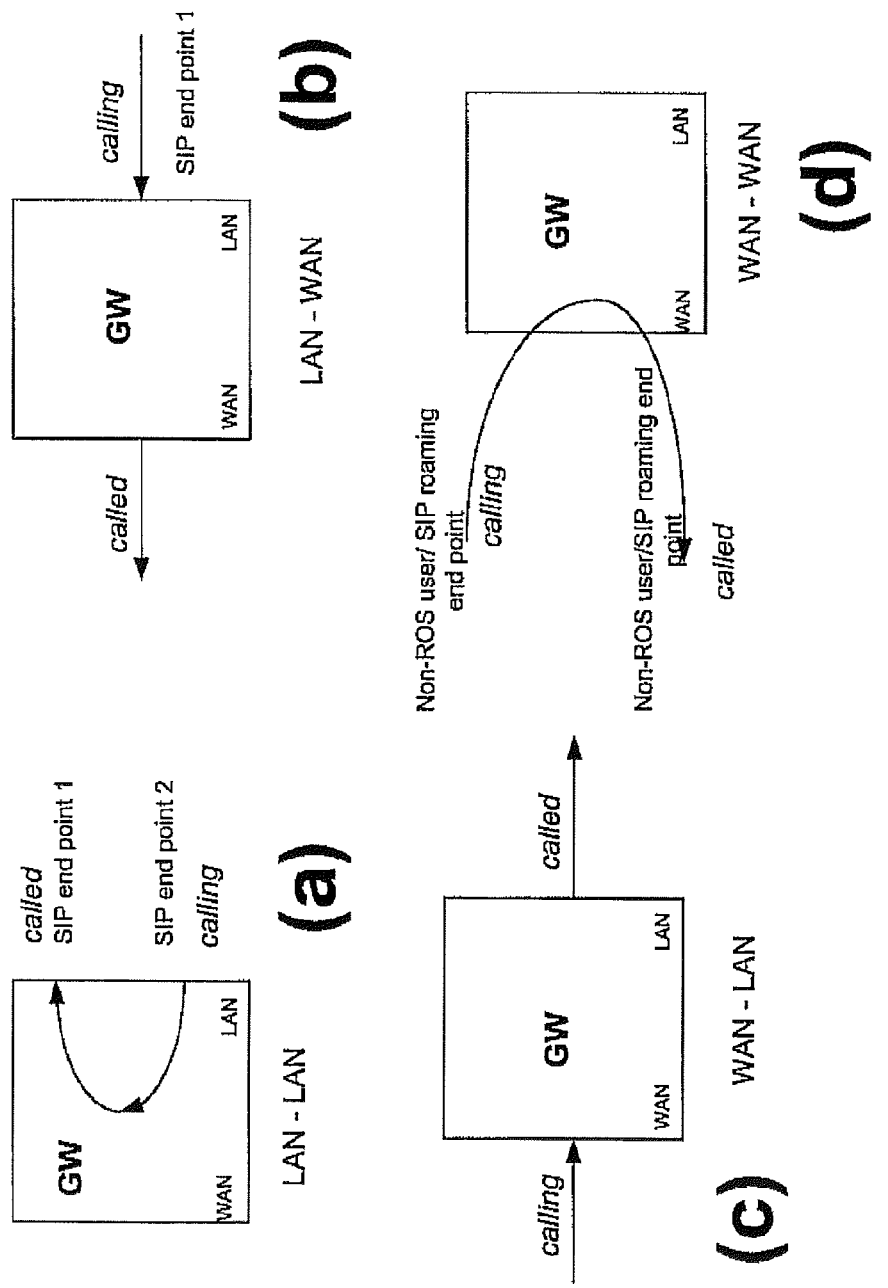
FIG. 1D illustrates the gateway appliance interface IP address and port of the gateway appliance according to one embodiment.

The following table defines the association between the FIG. 1C (signaling type) and FIG. 1D (gateway appliance interface IP address and port).

| Ingress signaling type (FIG. 1C) | Egress signaling type (FIG. 1C) | gateway appliance ingress signaling/media interface (FIG. 1D) | gateway appliance egress signaling/media interface (FIG. 1D) |
|---|---|---|---|
| LAN | LAN | 4 | 3 |
| LAN | WAN | 4 | 2 |
| WAN | LAN | 1 | 2 |
| WAN | WAN | 1 | 3 |

Call Forwarding and Transfer Scenarios

There are two types of call forwarding (CF) scenarios: 1) unconditional; and 2) no answer. A call is considered transferred when A calls B and B answers the phone and then transfers to C. The following example cases describe the population rules for the corresponding CDR fields for CF and call transfer scenarios.

Call Forwarding Scenarios for the Inbound Call

Consider the scenario A→B CF C. Call forwarding of B can only be performed to an off-net number and not to another extension. Hence, the following example cases 1)-3) are considered: in all the cases, only one CDR is generated by the gateway appliance and all the egress information will be that of the B→C call leg.

| Cases | A party | B party | C party |
|---|---|---|---|
| 1 | Off-net | In-house | Off-net |
| 2 | Roaming | In-house | Off-net |
| 3 | Roaming | Roaming | Off-net |

Example Case 1

| | | |
|---|---|---|
| 1) | ingressAni | DN of A (offnet number) |
| 2) | IngressSubscriberID | empty |
| 3) | Egress Ani | DN of B (DN of gateway appliance) |
| 4) | EgressSubscriberID | extension of B |
| 5) | ingressOriginalDestinationID: | B |
| 6) | ingressDestinationID | C |
| 7) | egressOriginalDestinationID | B |
| 8) | egressDestinationID | C (offnet number) |
| 9) | ingressFeature: | L |
| 10) | egressFeature: | L (since call cannot be forwarded to another extension this value will be always L) |
| 11) | ingressSignal type | WAN |
| 12) | egressSignal type | WAN |
| 13) | supplementary service | call forwarding |

Example Case 2

| | | |
|---|---|---|
| 1) | ingressAni | DN of A (DN of gateway appliance) |
| 2) | ingressSubscriberID | Extension of A |
| 3) | egress Ani | DN of B |
| 4) | egressSubscriberID | Extension of B |
| 5) | ingressOriginalDestinationID: | B |
| 6) | ingressDestinationID | C (offnet number) |
| 7) | egressOriginalDestinationID | B |
| 8) | egressDestinationID | C |
| 9) | ingressFeature: | R |
| 10) | egressFeature: | L (since call cannot be forwarded to another extension this value will be always L) |
| 11) | ingressSignal type | WAN |
| 12) | egressSignal type | WAN |
| 13) | supplementary service | call forwarding |

Example Case 3

| | | |
|---|---|---|
| 1) | ingressAni | DN of A (DN of gateway appliance) |
| 2) | ingressSubscriberID | Extension of A |
| 3) | egress Ani | DN of B |
| 4) | egressSubscriberID | Extension of B |
| 5) | ingressOriginalDestinationID: | B |
| 6) | ingressDestinationID | C (offnet number) |
| 7) | egressOriginalDestinationID | B |
| 8) | egressDestinationID | C |
| 9) | ingressFeature: | R |
| 10) | egressFeature: | L (since call cannot be forwarded to another extension this value will be always L) |
| 11) | ingressSignal type | WAN |
| 12) | egressSignal type | WAN |
| 13) | supplementary service | call forwarding |

Call Forwarding Scenarios for the Outbound Call

For the outbound call, the following example cases 1)-5) are considered. All the egress information will be that of the B→C call leg.

| Cases | A party | B party | C party |
|---|---|---|---|
| 1 | In-house | In-house | Off-net |
| 2 | In-house | Off-net | Off-net |
| 3 | In-house | Off-net | In-house |
| 4 | In-house | Off-net | roaming |
| 5 | In-house | Roaming | Off-net |

Example Case 1

| | | |
|---|---|---|
| 1) | ingressAni | DN of A (DN of gateway appliance) |
| 2) | ingressSubscriberID | extension of A |
| 3) | egress Ani | DN of C |
| 4) | egressSubscriberID | Empty |
| 5) | ingressOriginalDestinationID: | Extension of B |
| 6) | ingressDestinationID | C (offnet number) |
| 7) | egressOriginalDestinationID | C |
| 8) | egressDestinationID | C |
| 9) | ingressFeature: | E |
| 10) | egressFeature: | L (since call cannot be forwarded to another extension this value will be always L) |
| 11) | ingressSignal type | LAN |
| 12) | egressSignal type | WAN |
| 13) | supplementary service | call forwarding |

Example Case 2

The gateway appliance actually has no knowledge of the B→C call. So the CDR will be populated with the A→B call leg values.

| | | |
|---|---|---|
| 1) | ingressAni | DN of A (DN of gateway appliance) |
| 2) | ingressSubscriberID | Extension of A |
| 3) | egress Ani | DN of A (DN of gateway appliance) |
| 4) | egressSubscriberID | Extension of A |
| 5) | ingressOriginalDestinationID: | DN of B (offnet number) |
| 6) | ingressDestinationID | DN of B (offnet number) |
| 7) | egressOriginalDestinationID | DN of B (offnet number) |
| 8) | egressDestinationID | DN of B (offnet number) |
| 9) | ingressFeature: | E |
| 10) | egressFeature: | L |
| 11) | ingressSignal type | LAN |
| 12) | egressSignal type | WAN |
| 13) | supplementary service | empty |

Example Case 3

This scenario is considered as 2 independent calls and hence 2 CDRs are created, one for AB call leg and the other for BC call leg. AB call leg will be an outbound call and BC call leg will be an inbound call.

AB Call Leg CDR:

| | | |
|---|---|---|
| 1) | ingressAni | DN of A (DN of gateway appliance) |
| 2) | IngressSubscriberID | Extension of A |
| 3) | Egress Ani | DN of A (DN of gateway appliance) |
| 4) | EgressSubscriberID | Extension of A |
| 5) | ingressOriginalDestinationID: | DN of B (offnet number) |
| 6) | ingressDestinationID | DN of B (offnet number) |
| 7) | egressOriginalDestinationID | DN of B (offnet number) |
| 8) | egressDestinationID | DN of B (offnet number) |
| 9) | ingressFeature: | E |
| 10) | egressFeature: | L |
| 11) | ingressSignal type | LAN |
| 12) | egressSignal type | WAN |
| 13) | supplementary service | empty |

BC Call Leg CDR:

| | | |
|---|---|---|
| 1) | ingressAni | DN of B (DN of gateway appliance) |
| 2) | IngressSubscriberID | empty |
| 3) | Egress Ani | DN of B (DN of gateway appliance) |
| 4) | EgressSubscriberID | empty |
| 5) | ingressOriginalDestinationID: | DN of C (DN of gateway appliance) |
| 6) | ingressDestinationID | DN of C (DN of gateway appliance) |
| 7) | egressOriginalDestinationID | DN of C (DN of gateway appliance) |
| 8) | egressDestinationID | DN of C (DN of gateway appliance) |
| 9) | ingressFeature: | L |
| 10) | egressFeature: | E |
| 11) | ingressSignal type | WAN |
| 12) | egressSignal type | LAN |
| 13) | supplementary service | empty |

Example Case 4

This will be considered as 2 independent calls and hence 2 CDRs will be created, one for AB call leg and the other for BC call leg. AB call leg will be an outbound call and BC call leg will be an inbound call.

AB Call Leg CDR:

| | | |
|---|---|---|
| 1) | ingressAni | DN of A (DN of gateway appliance) |
| 2) | IngressSubscriberID | Extension of A |
| 3) | Egress Ani | DN of A (DN of gateway appliance) |

-continued

| | | |
|---|---|---|
| 4) | EgressSubscriberID | Extension of A |
| 5) | ingressOriginalDestinationID: | DN of B (offnet number) |
| 6) | ingressDestinationID | DN of B (offnet number) |
| 7) | egressOriginalDestinationID | DN of B (offnet number) |
| 8) | egressDestinationID | DN of B (offnet number) |
| 9) | ingressFeature: | E |
| 10) | egressFeature: | L |
| 11) | ingressSignal type | LAN |
| 12) | egressSignal type | WAN |
| 13) | supplementary service | empty |

BC Call Leg CDR:

| | | |
|---|---|---|
| 1) | ingressAni | DN of B (DN of gateway appliance) |
| 2) | IngressSubscriberID | Empty |
| 3) | Egress Ani | DN of B (DN of gateway appliance) |
| 4) | EgressSubscriberID | Empty |
| 5) | ingressOriginalDestinationID: | DN of C (DN of gateway appliance) |
| 6) | ingressDestinationID | DN of C (DN of gateway appliance) |
| 7) | egressOriginalDestinationID | DN of C (DN of gateway appliance) |
| 8) | egressDestinationID | DN of C (DN of gateway appliance) |
| 9) | ingressFeature: | L |
| 10) | egressFeature: | R |
| 11) | ingressSignal type | WAN |
| 12) | egressSignal type | WAN |
| 13) | supplementary service | Empty |

Example Case 5

The ingress CDR includes the information of the AB call leg and the egress CDR contains the information of the BC call leg.

| | | |
|---|---|---|
| 1) | ingressAni | DN of A (DN of gateway appliance) |
| 2) | ingressSubscriberID | Extension of A |
| 3) | egress Ani | DN of B |
| 4) | egressSubscriberID | Extension of B |
| 5) | ingressOriginalDestinationID: | Extension of B |
| 6) | ingressDestinationID | C (offnet number) |
| 7) | egressOriginalDestinationID | Extension of B |
| 8) | egressDestinationID | C (offnet number) |
| 9) | ingressFeature: | E |
| 10) | egressFeature: | L (since call cannot be forwarded to another extension this value will be always L) |
| 11) | ingressSignal type | LAN |
| 12) | egressSignal type | WAN |
| 13) | supplementary service | call forwarding |

It is desirable to provide systems and methods that enable enhanced managed services while supporting and managing the emerging digital home. It is a feature of the present invention to include a system, such as the gateway appliance thoroughly described herein, that can offer enhanced managed services to its users via incorporation of causation and correlation engine abilities. A causation and correlation engine can be personalized and enable broader services for system/gateway users. The enhanced features can be referred to as being provided by a Personal Causation and Correlation Engine (or "PCCE). Areas where a PCCE can be used include establishing objectives, tracking performance, and influencing behavior and conformance in the areas of financial, health medical objectives, exercise, nutrition, advertising, home security, purchasing, and energy conservation, etc.

The PCCE enables users and others to establish objectives and preferences in regards to various aspects of a users' condition and behavior and the PCCE correlates events and data and determines messaging, communication, special offers, rewards, and other incentives to cause the user to comply with certain behavior or actions. Users, coaches, recognized authorities or others may establish objectives. Based upon a vast array of real-time or near real-time events, stored dynamic data, profile information, and records of the previous effectiveness of prior causation actions, the PCCE identifies appropriate opportunities and methods of personalized communication to influence causation actions. This communication can be tailored for each user based upon user preferences and what can be known about the user and their environment. The PCCE may also leverage information regarding the user's social media contacts to establish influence and can also enlist the support of social media contacts to influence the user. The user's social media contacts may be incented to provide influence by sending messages and other communication to the user; these incentives for contacts and friends are personalized and tailored based upon what can be known about each specific social media contact. Information reflecting the correlated data and instigating event(s) are submitted to expert rules-driven applications and personalized messaging and events are created which cause the user to make decisions and perform actions, which are complementary to the user's personalized objectives. Some rules driven applications (such as home automation) can be controlled partially or exclusively by the user, while others, such as e-health, can be controlled by experts or other $3^{rd}$ parties. The PCCE can interact with both an advertising server and one or more rules-based applications to formulate causation actions and messaging.

High Level Processing with PCCE

When the PCCE determines there is an opportunity or need for communication based upon real-time and near-real time instigating events, the PCCE will determine, based upon prioritization and objectives, the attributes of the desired communication, the method of communication and the type of communication as expressed by the user and/or determined by the PCCE, and can formulate or update an encoded token, which represents the opportunity, the type and method of desired communication. These token segments can be stored and maintained (that is updated based upon events) for each individual in the home and the home in general. The encoded token can be passed to the appropriate rules-based application component. The messaging component can be an application specific messaging component with rules that are controlled by medical professionals and behavioral scientists such as seen in an e-health app or the intelligent ads server, which can interoperate with another $3^{rd}$ party component such as a rules-based advertising platform.

Based upon the attributes expressed in the PCCE token, the messaging component can return data indicating the messaging identifiers, content, and other messaging attributes. The PCCE agent will process this information and invoke the communication and direct the communication to the "best" user interface(s) using the "best" (best-rated as most effective) method for that interface and based upon what is known about the user (and an attribute indicating if the message should be displayed in public (TV, etc.) or private interface). The PCCE can also determine that a social media contact may be enlisted in the causation (these contacts may be selected and prioritized by the user or other coaches), and the PCCE may express this in the token that can be sent to the messaging components. The messaging component can respond back with data that enables the PCCE agent to invoke communication to the social media contact to cause and incent the social media contact to communicate with the user to influence their behavior. The PCCE can also dynamically store and correlate the metadata of responsiveness of the user to prior messaging; these metrics and rankings can be used for subsequent causation decision-making and can be submitted to the rules based applications.

The PCCE can also integrate messaging and advertising and incentive messaging to provide enhanced encouragements for users and providing compelling incentives for positive actions. The PCCE can also support two or more users as groups with common objectives and enable sharing of events and actions among the groups. The real-time events, dynamic data, profile information, and other user data from each domain is stored and indexed as domain-specific metadata. This metadata is processed by the correlation component to create token segments, which are then passed to the causation component. The correlation component may interact with service applications to establish thresholds for specific metrics (e.g. weight, energy usage, spending levels/month) and request to be informed of when these thresholds are met or exceeded. The PCCE may also detect and incorporate information about the location and presence of other family member users or their location when formulating a causation event.

The PCCE can enable users and others to establish preferences regarding application/domain specific items (e.g., preferred food types, types of exercise, timing of exercise, sedentary durations, shopping preferences, etc.). Attributes, meta-data, and token information may be kept private using a data encryption unit 162 and/or other application-level encryption. The user's identity may or may not be exposed to the messaging and advertising components. Messaging and interaction can be directed towards one or more endpoints and may also invoke actions within other applications such as the home and energy management applications.

In some cases, the PCCE may enable messaging and interaction on one endpoint, such as a TV or mobile device (smart phone, tablet, etc.), and the user may be prompted to enable supplemental interaction on another endpoint such as a mobile device or TV. The PCCE stores records/logs of the initial interaction and correlates the subsequent interaction events on the second screen with the initial interaction and user. Records of screen specific interaction can be stored for a configurable period of time, or for a configurable number of interaction events. Upon initialization, initial token in the form as metadata "documents" instances are formulated by the correlation component. The correlation component stores a copy of current token instances and retrieves these documents upon subsequent restart.

The configuration of metadata indexes, which form the token documents to be stored, can be under control of the service management center and based upon the service applications 130 provisioned via the service management and support center 50. After the tracking indexes are established, the PCCE requests data from each service application and/or API, and also registers to be informed of events and data changes within each service and platform application. Depending upon configuration options controlled by the service management center 50, the user may be able to delete the personal data and metadata and "opt" out of the causation processing. The user may also be able to export the data to a personal device or storage area.

PCCE Component Descriptions:

Real-time and near real-time events—These events are generated by various components and applications such as calendar, weather & forecast, home automation, energy management, e-health, location and proximity, social media, music/media services, and other applications. Dynamic Data and Trends—These data types can access and acquire data related to home, health, and financial, etc., conditions. The value of a (meta) data element may trigger an event, also complex datasets and content may be processed down to metadata and stored as key value pairs of meta-data. This metadata is stored, prioritized, and indexed (by the app or the PCCE) and subsequently processed by the correlation component, which will formulate personalized token segments.

Profile—These data types are generally more static and less dynamic than the real time events or dynamic data. The profile information includes data that is stored on the gateway or can be acquired via web service calls (and cached) or other types of remote access. As the profile data is processed, meta-data is generated and stored and this meta-data is used by the correlation component, which will formulate personalized token segments. User/Expert Objectives—These data types are meta-data which represent the domain-specific objectives, which could be established by the user or domain specific objectives. The correlation engine accesses this data and personalized token segments.

Historical Responsiveness—metadata that the PCCE uses to express previous effectiveness at causation can be used by the PCCE in token formulation and also accessed by $3^{rd}$ parties (analytics, etc.) to track and measure effectiveness. Correlations Component—formulates (and can maintain) token segments based upon access to all metadata (events, dynamic data, profile, objectives, etc.). Correlations Component—formulates and maintains token segments based upon access to all metadata, receives triggering events, updates the metadata token segments, and passes triggering event and token segments to causation (events, dynamic data, profile, objectives, etc.).

Causation Component—receives triggering event and metadata token, determines which rules/apps platforms to submit to, constructs and encodes token based upon target rules/apps platforms, and passes to causation agent. Causation Agent—receives encoded token, encrypts and routes to rules/apps platforms, receives response from rules/apps, and formulates API service calls to application interfaces based upon the response from the rules platforms.

Figure 8:
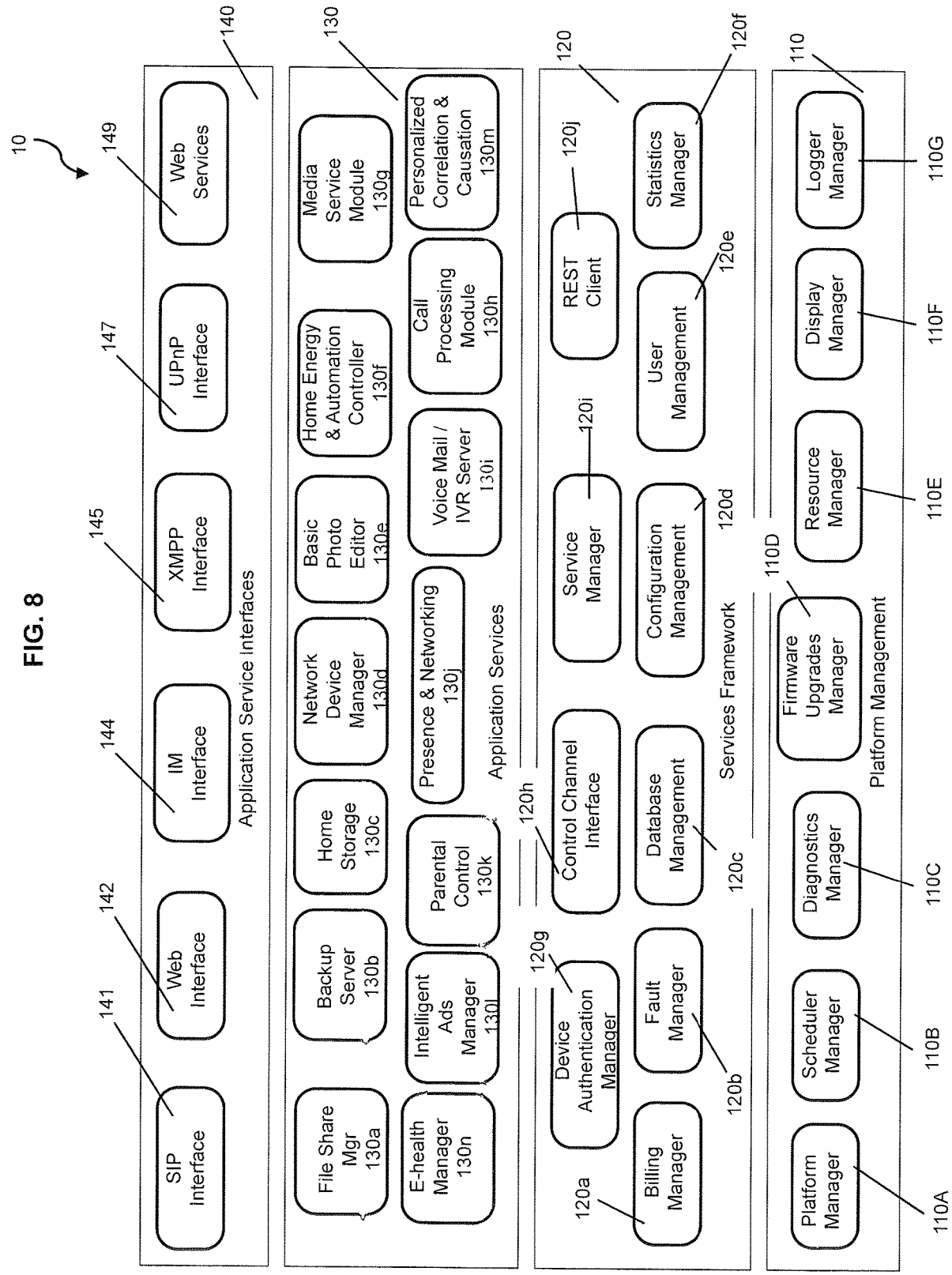
FIG. 8 illustrates high-level block diagram of PCCE module, which can be associated with the services layer within the application gateway.

Referring to FIG. 8, the drawing depicts a high-level view of PCCE module 2201, which is associated with the services layer 130 within the application gateway. Application services interfaces 140 operating as part of the PCCE interacts with internal components such as the Intelligent Ad Server 130*l*. Other layers associated with the PCCE are the Platform management layer 110, service Framework layer 120 and the services layer 130. Applicant Service interfaces 140 can include: SIP interface 141, Web interface 142, IM interface 144, XMPP Interface 145, UPnP Interface 147 and Web Services 149. The services layer 130 can include the following modules: File Share manager 130*a*, Backup Server 130*b*, Home Storage 130*c*, Network Device Manager 130*d*, Basic Photo Editor 130*e*, Home energy & Automation Controller 130*f*, Media Service Module 130*g*, E-health Manager 130*n*, Intelligent Ads Manager 130*l*, Parental Control 130*k*, Presence & Networking 130*j*, Voice Mail/IVR Server 130*i*, Call Processing Module 130*h*, Personalized Correlation & Causation 130m. Services Framework 120 can include the following modules: Billing manager 120a, Fault manager 120b, Database Management 120c, configuration Management 120d, User Management 120e, Statistics manager 1120f, Device Authentication Manger 120g, Control Channel Interface 120h, Service Manager 120i, REST Client 120j. Platform Management 110 can include the following management modules: Platform Manager 110A, Scheduler Manager 110B, Diagnostic Manager 10C, Firmware Upgrades Manager 110D, Resources Manager 110E, Display manger 110F, and Logger manager 110G.

Figure 9:
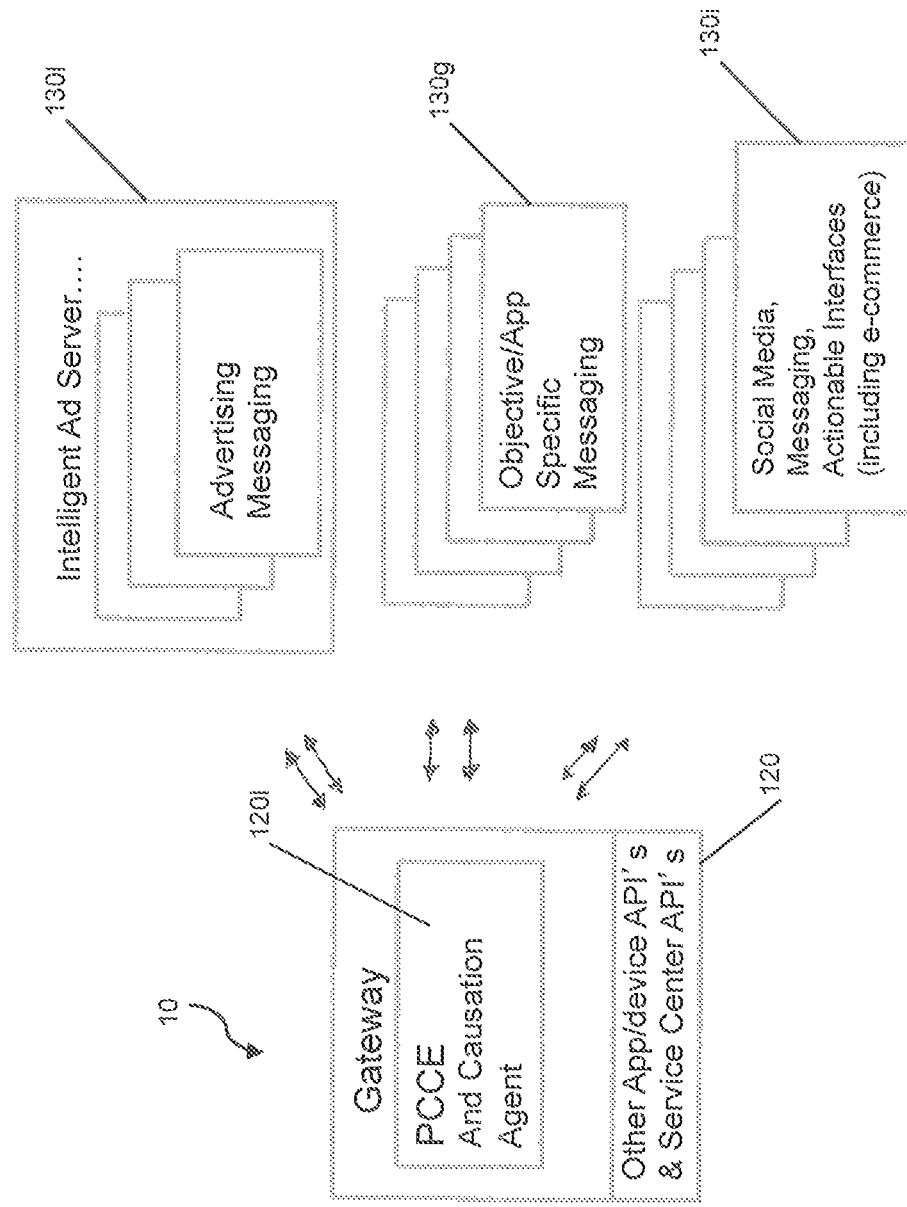
FIG. 9 illustrates an expanded view of drawing 2C depicting the PCCE module within the software architecture of the application gateway.

FIG. 9 provides an expanded view of drawing 21 depicting the PCCE 2201 module within the software architecture of the application gateway 10. Utilizing the framework and interfaces previously described in FIG. 2C, the PCCE can communicate with other internal and external components including, but not limited to, application service interfaces 140, application services 130, services framework modules 120, and platform management components 110.

Figure 10:
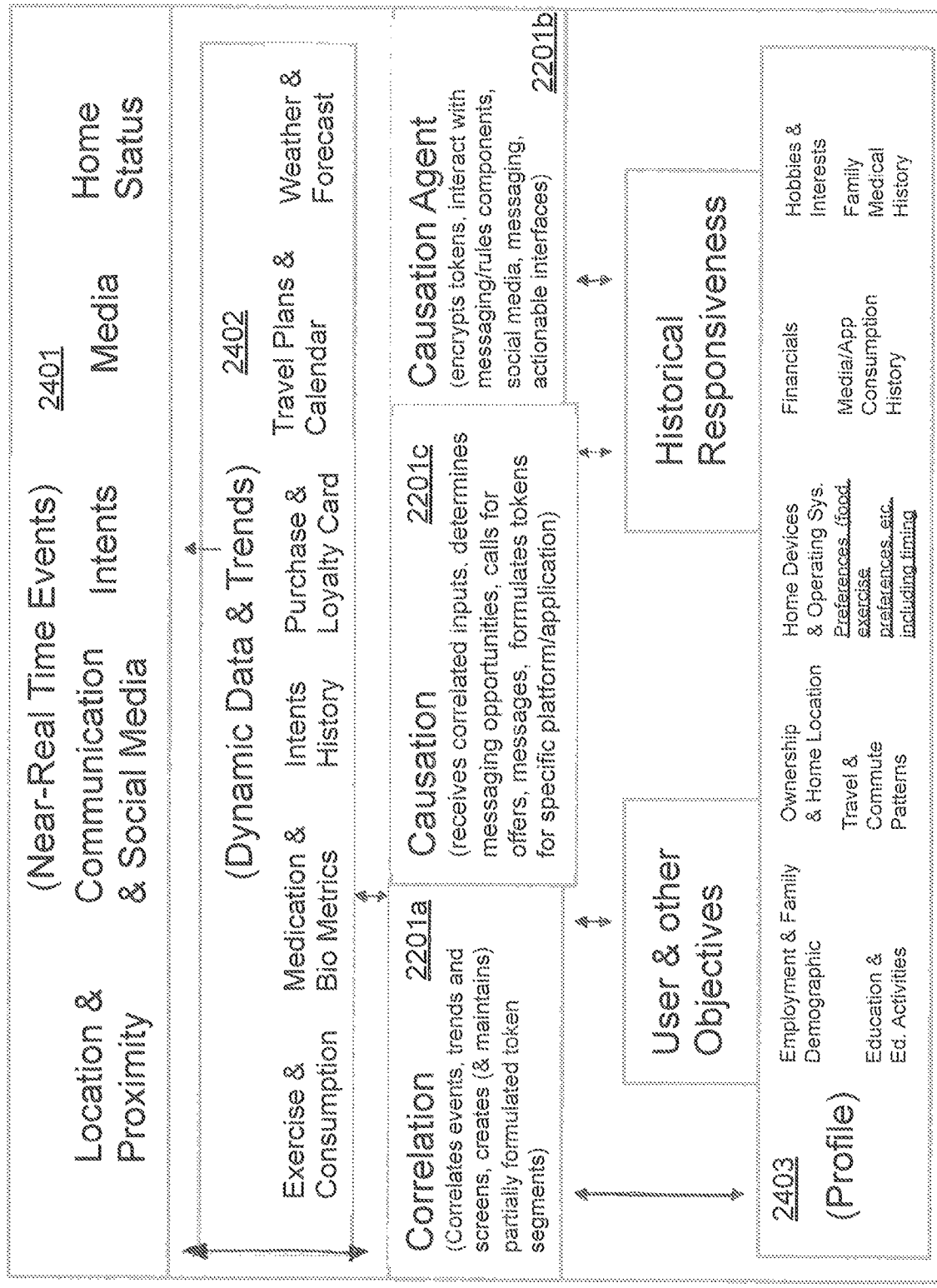
FIG. 10 illustrates a detailed view of the PCCE, PCCE sub-module components, and a logical view of the exemplary sources of data and events acquired and utilized by the PCCE.

FIG. 10 provides a detailed view of the PCCE 2201, the PCCE sub-module components, and a logical view of the exemplary sources of data and events acquired and utilized by the PCCE 2201. The PCCE 2201 is comprised of three sub-modules, the correlation 2201a module, the causation sub-module 2201b, and the causation agent sub-module 2201c. Together, these three sub-modules access data, receive events, and interact with internal and external application services and expert-driven rules platforms to deliver user messaging and coaching, invoke application actions, present incentives, and influence user behavior. The logical view of the data and events depicted in FIG. 10 can include real-time events 2401, dynamic data and trends 2402, and profile data 2403. Real-time events 2401 are events that are communicated from devices and applications such as, but not limited to, the home energy and automation controller and sensor devices that can be deployed throughout a venue or environment, automatically controlled lighting or lamp units, and laptop/mobile devices connecting as clients to the gateway 10. Dynamic data and trend data 2402 represent changing data such as, but not limited to, weather forecasts, stock portfolio information, and e-health monitoring statistics. When this type of data reaches a configurable threshold, a message indication is routed to the PCCE correlation sub module 2201a. Profile data 2403 is data that is generally more static, less dynamic data such as, but not limited to, user preferences, demographic information, family medical history data, application usage statistics, and the like. Real-time events 2401 are events communicated via internal or external messaging from other applications, the service management center or the application gateway itself. The PCCE can poll the internal and external sources of data and events at configurable interval; the PCCE can also register or subscribe to be informed of application events or data changes.

Now turning to the PCCE 2201 and sub-modules, the 2201a correlation sub-module establishes meta-data indexes based upon application gateway 10 configuration data that is provisioned by the service management center and the configuration data is based upon the application services, which the user subscribes to. These metadata indexes, which can be stored as xml, text string formats, or relational data formats, can contain a category such as "shopping", and a primary sub-category such as "women's apparel", then a secondary sub-category such as "shoes", then a specific value such as "running shoes". These xml, text string data, or relational data are stored in persistent storage and maintained as an in-memory document and are updated as new events and evented data are received. As another example of the type of data that is stored in the meta-data indexes, the correlation sub-module may have meta data related to e-health such as "e-health", "medication taken=cholesterol", "brand=xyx", "quantity=20" "unit=mg", "frequency=once per day". The event data can be stored with time stamps and an indicator indicating the type of event. A meta-data document instance may be maintained for each user registered within the premise and another meta-data document instance may be maintained for the home or user premise itself. The meta-data document instance may also contain data relating to a user's social media contacts and their preferences. Depending upon the type of event received, the correlation sub-module 2201a may determine that a token may need to be formulated from one or more of the meta-data instances with an event indicator and one or more instances of meta-data for a user and or for the home. The correlation sub-module 2201a will formulate the token and pass this token to the causation sub-module 2201b. The causation sub-module 2201b will receive the token and determine what screens may be available for messaging, what rules-based platforms and social networks should be engaged, and passes this information to the causation agent 2201c along with information on what platforms should be engaged and what screens should be subsequently addressed with messaging that will be received from the rules-based platforms. It should be noted that in order to increase performance, the token may be further compressed and passed as an index with the format of the index being known by the internal or external rules-based platforms. With this method, the events and attributes of the user may be passed to the rules-based and/or advertising platforms, but the actual identity of the user may not be exposed to the third party platform. This method is a significant departure from the well-known internet browser-based "cookie" method of tracking users and supplying advertising and other services. In the "cookie method", a string of data is stored within the user's browser, which identifies the user. All attributes and preferences are stored on back-office systems and the user often has limited knowledge of or control of the data. With the present attribute-based token method, the back-office systems are presented with attributes and the back office systems determine responses based upon the attributes presented, not necessarily upon the identity of the user. The causation agent sub-module 2201c receives the token from the causation sub-module 2201b and based upon the attributes of the token and the routing meta-data, optionally encrypts the token and routes the token to the rules-based platforms via the application services interfaces 140 and awaits a response. Note that the causation agent may send and receive more than one token to more than one rules-based platform per instigating event. Upon receiving a response(s) from the rules-based platform(s), the causation agent 2201c encapsulates the response and routes the response to all applicable local or remote devices (30a), media adapter element 35b, set top boxes 35a, TVs and screens as shown in FIG. 1a, and application services 130. The PCCE may also cache messaging and advertisements, including videos, which may be presented to the user at a later time or when the screen becomes active.

The PCCE 2201 may also subsequently receive information regarding the subsequent user responses to the message or advertisement. This user response information is stored and can be used as meta-data in the index document indicating the success rate of different types of messaging. With this method, the historical record of a user's compliance or responsiveness can be subsequently presented to rules-based platforms and can be used when formulating subsequent communications. This user response information may also be retrieved by the service management center, which can aggregate and summarize the relative success of specific messaging and this summary may also be distributed to other application service gateways 10 and the rules-based platforms.

Figure 11:
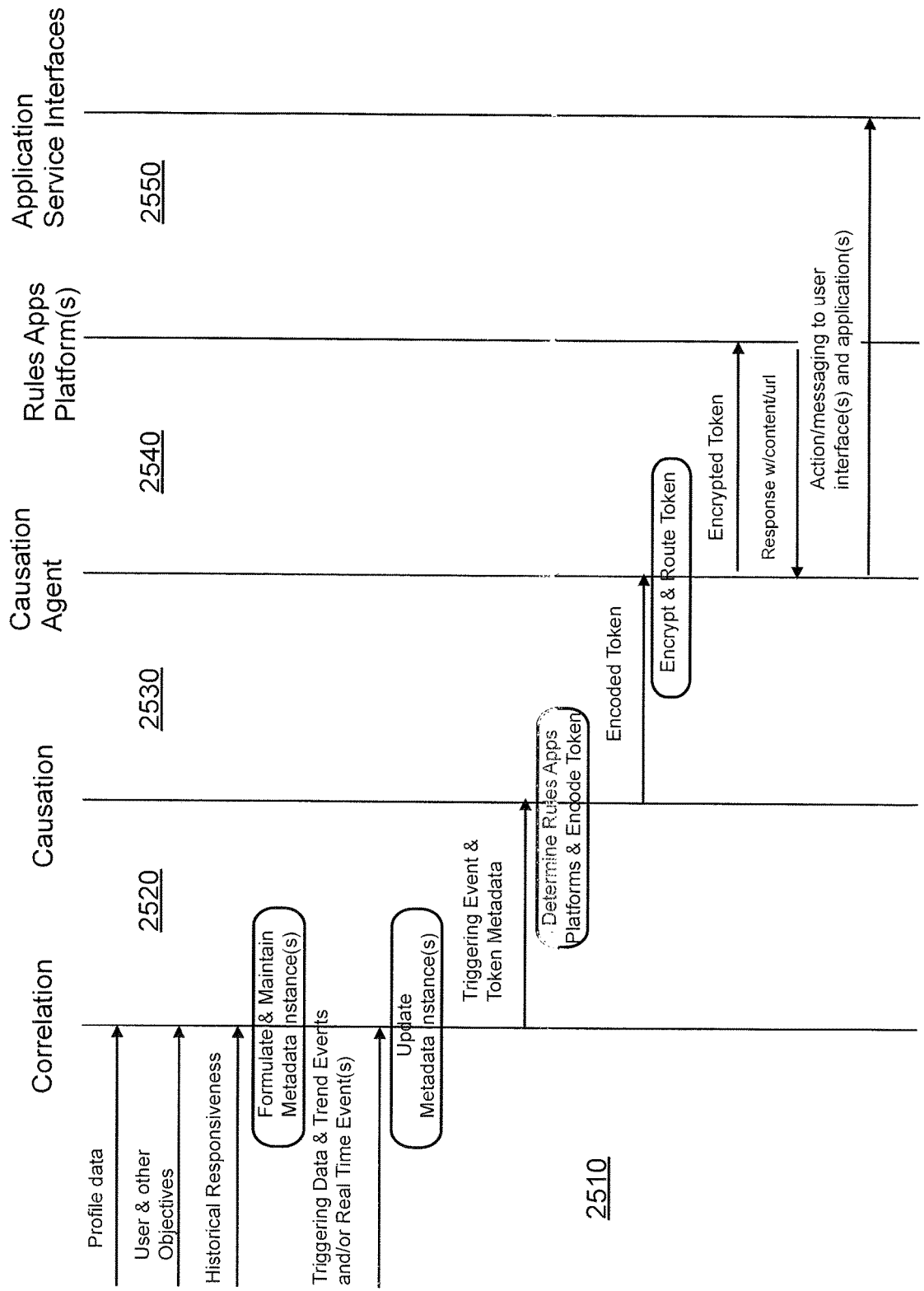
FIG. 11 illustrates an example of meta-data collection and event processing as carried out by the PCCE, appliance, and system of the present invention in one embodiment.

FIG. 11 illustrates an example of meta-data collection and event processing as carried out by the PCCE 2201 appliance and system of the present invention in one embodiment. Step 2510 performs data collection and the formulation and maintenance of the meta-data document instantiation(s), including setting the values of the meta-data indices. At step 2520, the correlation sub-module 2201*a* receives a triggering or instigating event and updates the meta-data token and determines if the event requires the correlation sub-module 2201*a* to notify the causation sub-module 2201*b*. This notification criteria is configurable and under the control of the service management center 50. The correlation sub-module 2201*a* updates the meta-data token and the triggering events and if the triggering event is found in the event table lookup, the correlation sub-module 2201*a* prepares this token instance to send to the causation sub-module 2201*b*. At step 2530, the causation sub-module 2201*a* receives the events, and based upon the triggering event ID and the meta-data token value, the causation sub-module 2201*b* determines what rules-based platforms the token should be directed towards. This determination of which platform(s) to engage is achieved by means of a local table look-up as configured by the service management center. After the causation sub-module processes the token and optionally further compresses the token and determines if the users identity should be hidden, based upon configuration data received from the service management center, the causation sub-module 2201*b* passes the token and platform meta-data, including platform IDs, to the causation agent sub-module 2201*b*. In step 2540, the causation agent receives the token event and, based upon the platform ID(s) meta-data which contains one or more internal or external rules-based platform identifiers, optionally encrypts the token, routes the token to the application services interface(s) 140, and awaits a response. In step 2550, the causation agent receives a response from the rules-based platform(s) 2204 and, based upon the response from the rules-based platforms 2204 and the current local or remote devices (30*a*), media adapter element 35*b*, set top boxes 35*a*, TVs and screens, and application services 130 that are in use and available, routes the message and/or uniform location resource address to the appropriate devices, screens, applications, and the like.

Note that although the steps shown in FIG. 11 all represent positive processing and responses, error handling, and time-out logic is supported in all the sub-modules and interfaces.

The PCCE can provide users access to many services and information sources including:

- Ownership/purchasing (e.g., cars, real estate, music, movies, consumer products, electronic products)
- Loyalty Card purchase information
- Employment, Occupation, Employment History, Salary, Benefits, Type of Insurance
- Location information (e.g., location now, micro-location now, location patterns, businesses frequented, commuting methods)
- Travel Plans, Travel History, Device presence and status
- Hobbies & Community Activities
- Hobbies, Interest Groups, Church Groups, Continuing Ed classes, Volunteer Activities
- Communications (e.g., phone calls, texts, email, web-based, IM and IM status, twitter interests, etc.)
- Financial (e.g., stock/bond portfolio, and stock bond performance, checking/savings, bills and obligations, medical bills)
- Intents (e.g., search information, browsing history, app usage, travel itinerary, schedule/appointments calendar, "To-Dos")
- Education Activities
- History and Present
- Home/office Status (e.g., devices offline and devices online, heating/AC status, alarm system status, presence, lights, garage doors, locks, motion detectors, cameras, etc.)
- Purchase Information
- Musical Interests
- Social Media/Network (e.g., social network contacts, interests and intents, social media groups, Twitter followings, focused social media, contacts and their interest and intents)
- Exercise & Sleep (e.g., status, history and patterns, performance, user goals, personal coach goals exercise & sleep, (weekly, daily activity level, etc.))
- Medical Info Status and History (e.g., prescription info/bills, user responsiveness history, user causation preferences, user goals, medical coach goals, injuries, diseases, medical conditions and ailments, medications, providers and visits, schedule, medication status, current medical metrics (BP, weight, glucose, etc.) and trends)
- Commerce (e.g., advertising goals, purchase information, media, media interest, music, video, movies, games, books, articles, real time consumption status)

The following are exemplary usage scenarios for the PCCE:

- Blood Pressure Check—Results High, alert personal coach
- Weight Check—Results Low—Celebration action and/or alert personal/medical coach and/or cause device or home automation action such as flashing of lights.
- Medication Reminder Event
- Medication Reminder not acknowledged—Alert Professional Coach or Personal Coach
- Blood Pressure Check—Results good, offer reward for user and their personal coach, or direct reward to favorite charity
- Location alert, at restaurant, send incentive to coach or contact to in turn send recommendation to user for "smart food" choice, or alert user to "better" restaurant choice based upon location, consumption objectives, profile preferences, advertiser objectives, etc.
- Location alert, at store, based upon previous purchase of product such as coffee maker, provide incentive for purchasing additional coffee, etc.
- Travel itinerary includes air flight, notify user of low impact exercises to try on the plane
- Media Search Event—present recommendation based upon previous viewing or social contacts current or previous viewing
- Screen based Call for advertising—present ad based upon recent intents (intents=searches, phone calls meta-data, profile data, user exercise or medical objectives)
- Micro Location event—user is in living room, medication not acknowledged, send reminder to TV
- Acceptable Sedentary Duration Exceeded, suggestions/reminder sent to run errands, perform other tasks on "to-do" lists, etc. (after the movie is over, of course), could also be reminders from incented friends, contacts, etc.

Calendar alert, user traveling in 3 hours, send reminder to leave for airport in 1.5 hours (based upon location) and remind/confirm user packed medication Call for advertising from screen, request ad based upon user's travel itinerary, objectives, interests and search history Reminder—Garage door open, call for ad (based upon token) and send with notification.

Location—Near Home Depot and calendar open (25 mins before picking up kids), suggest buying AC filter which needs replacing or offer to order online and ship directly to house.

Unexpected Expense, offer money-specific saving suggestions and offers to control expenses during the month.

Weather forecast=rain/snow/ice, adjust travel schedule to airport and confirm flight schedules Examples of identity detection: Login use ID, Voice Detection, Face Recognition, Facial Expression Recognition, Micro presence detection, Macro presence detection (and correlated to schedule), Activity or Sedentary detection, Typing/tapping pattern detection (detect based upon typing/taping habits)

E-commerce: track purchases, maintain profile information, billing info, cache relevant ads, recommendation based on profile Home automation: manage mix of devices with automated control or controlled by the user, rules-based processing to trigger action based on sensor/event (e.g., thermostat, alarm sensor, door bell) and communication out to user or $3^{rd}$ party.

The PCCE can monitor/track user responsiveness history and user causation preferences. It can help determine what the users respond to and what types of stimuli motivate to desired results (e.g., friend prompts, authoritarian prompts, positive prompts, negative prompts, special offers, special offers and rewards to friends or causes, frequent reminders, and infrequent reminders, etc.). It can include configurable notification and causation and can be based upon user goals: financial, consumer, media, medical, physical, safety and security, home maintenance, energy consumption, intents, and informational goals. It can also be based upon other entity goals: personal coach goals, medical coach goals, advertiser goals, and service provider goals.

The present invention has been described with reference to diagrams of methods, apparatus (systems), and computer program products according to embodiments of the invention. It will be understood that each diagram can be implemented by computer program instructions. These computer program instructions may be provided to a processor of a general purpose computer, special purpose computer, embedded processor or other programmable data processing apparatus to produce a machine such that the instructions, which execute via the processor of the computer or other programmable data processing apparatus, create means for implementing the functions specified herein.

These computer program instructions may also be stored in a computer-readable memory that can direct a computer or other programmable data processing apparatus to function in a particular manner such that the instructions stored in the computer-readable memory produce an article of manufacture including instruction means which implement the function specified herein.

The computer program instructions may also be loaded onto a computer-readable or other programmable data processing apparatus to cause a series of operational steps to be performed on the computer or other programmable apparatus to produce a computer implemented process such that the instructions which execute on the computer or other programmable apparatus provide steps for implementing the functions specified herein.

While the invention has been particularly shown and described with respect to illustrative and preformed embodiments thereof, it will be understood by those skilled in the art that the foregoing and other changes in form and details may be made therein without departing from the spirit and scope of the invention which should be limited only by the scope of the appended claims.

What is claimed is:

1. An IoT system with cloud storage access, comprising:
one or more processors;
at least one WiFi interface configured for enabling access to a wide area network and/or a local area network that is at a user premises; and
one or more memories locally storing instructions that, when executed by the one or more processors, cause the IoT system to:
enable a first user to remotely control, via a web-enabled application, content captured by the IoT system,
wherein the web-enabled application enables the first user to:
selectively invite one or more individuals to access the content upon successful authentication, and
control secured access, by the invited one or more individuals that have been authenticated, to the content, wherein the first user is capable of revoking authentication credentials of at least one of the invited one or more individuals and disallow access to the content.

2. The IoT system of claim 1, wherein execution of the locally stored instructions further enables the first user to locally store content at the user premises and to access the locally stored content.

3. The IoT system of claim 1, wherein the remote control includes setting one or more triggers for controlling operation of the IoT system based on at least one event detected using content obtained at the user premises.

4. The IoT system of claim 1, wherein execution of the locally stored instructions further enables the IoT system to encrypt content and subsequently decrypt content based upon positive authentication of the invited one or more individuals and based upon associated valid authentication credentials.

5. The IoT system of claim 1, wherein the first user is able to modify an amount of the content accessible to the invited one or more individuals.

6. The IoT system of claim 1, further including a first application hub that contains at least a portion of the content at the user premises and is accessible via a second application hub that is located remote from the first application hub.

7. The IoT system of claim 1, wherein
the first user is capable of controlling secured access by revoking authentication credentials and/or modifying an amount of the content accessible to the invited one or more individuals, and
the content includes personal e-health information and/or medical information.

8. The IoT system of claim 1, wherein the IoT system enables the invited one or more individuals to place tags and/or comments on the content.

9. The IoT system of claim 1, wherein the invited one or more individuals is notified of content updates automatically as they occur if a change in the content is detected.

10. The IoT system of claim 1, wherein the IoT system locally stores content in a memory storage element, a hard drive, or disk memory storage.

11. The IoT system of claim 1, wherein execution of the locally stored instructions causes storage of trigger actions, sensor data, and/or event data, wherein one or more cameras capture the content.

12. The IoT system of claim 1, wherein the content includes video and/or media content.

13. The IoT system of claim 1, further comprising a management center and at least one device with the one or more processors, the at least one WiFi interface, and the one or more memories.

14. The IoT system of claim 1, wherein the IoT system enables streaming of at least portion of the content to a display device.

15. The IoT system of claim 1, wherein the IoT system enables the first user to control access to (a) locally stored content and/or (b) content stored remotely from the user premise.

16. A method for managing content, the method comprising:
enabling a first user to remotely control, via a web-enabled application, operations of an IoT system to capture content, wherein the IoT system is at a user premises and is communicatively connected to the web-enabled application via (1) a wide area network and/or (2) a local area network that is at the user premises;
enabling the first user to selectively invite one or more individuals to access the content; and
enabling the first user to control secured access, by the invited one or more individuals that have been authenticated, to the content, wherein the first user is capable of revoking authentication credentials of at least one of the invited one or more individuals and disallow access to the content.

17. The method of claim 16, further comprising encrypting locally stored content and subsequently decrypting locally stored content based upon positive authentication of authentication credentials.

18. The method of claim 16, further comprising enabling the first user to modify an amount of the content accessible to the invited one or more individuals.

19. The method of claim 16, further comprising allowing an electronic device that is located remote from user premises to access the content.

20. The method of claim 16, wherein the content includes video, still images, personal e-health information, and/or medical information.

21. The method of claim 16, further comprising associating tags and comments from the first user with the content.

22. The method of claim 16, further comprising notifying the invited one or more individuals of automatic updates as they occur when an automatic update causes a change of the content.

23. The method of claim 16, further comprising disallowing access to the content by any invited one or more individuals with revoked authentication credentials.

24. The method of claim 16, further comprising locally storing content in a memory storage element, disk memory storage, or a hard drive.

25. The method of claim 16, further comprising sending the content for streaming to the invited one or more individuals and/or the first user.

26. A non-transitory computer-readable storage medium storing instructions that, when executed by a system, cause the system to perform operations comprising:
enabling a first user to remotely control, via a web-enabled application, operations of an IoT system at a user premises to capture and store content, wherein the web-enabled application is communicatively coupled to the IoT system via (1) a wide area network and/or (2) a local area network that is at the user premises;
enabling the first user to selectively invite one or more individuals to access the content; and
enabling the first user to control secured access, by the invited one or more individuals that have been authenticated, to the content, wherein the first user is capable of revoking authentication credentials of at least one of the invited one or more individuals and disallow access to the content.

27. The non-transitory computer-readable storage medium of claim 26, wherein the operations further comprise encrypting the content and subsequently decrypting the content based upon positive authentication of authentication credentials.

28. The non-transitory computer-readable storage medium of claim 26, wherein the operations further comprise enabling the first user to modify an amount of the content accessible to the first user and/or invited one or more individuals.

29. The non-transitory computer-readable storage medium of claim 26, wherein operations further comprise allowing a first hub device that is located remote from second hub device to access content stored by the second hub device.

30. The non-transitory computer-readable storage medium of claim 26, wherein the content includes personal e-health information and/or medical information.

31. The non-transitory computer-readable storage medium of claim 26, wherein the invited and authenticated of the one or more individuals can place tags and comments on accessible content from the user premises.

32. The non-transitory computer-readable storage medium of claim 26, wherein the operations further comprise notifying the invited one or more individuals of automatic updates to the content.

33. The non-transitory computer-readable storage medium of claim 26, further comprising:
locally storing content at the user premises, and
sending at least a portion of the locally stored content for remote viewing, via the web-enabled application, by the invited one or more individuals.

* * * * *